United States Patent
Denham et al.

(10) Patent No.: US 9,271,713 B2
(45) Date of Patent: Mar. 1, 2016

(54) METHOD AND APPARATUS FOR TENSIONING A SUTURE

(75) Inventors: Gregory J. Denham, Warsaw, IN (US);
Kevin T. Stone, Winona Lake, IN (US);
Michael A. Wack, Warsaw, IN (US)

(73) Assignee: BIOMET SPORTS MEDICINE, LLC, Warsaw, IN (US)

( * ) Notice: Subject to any disclaimer, the term of this patent is extended or adjusted under 35 U.S.C. 154(b) by 1143 days.

(21) Appl. No.: 13/295,126

(22) Filed: Nov. 14, 2011

(65) Prior Publication Data

US 2012/0059418 A1    Mar. 8, 2012

Related U.S. Application Data

(60) Continuation-in-part of application No. 12/938,902, filed on Nov. 3, 2010, now Pat. No. 8,597,327, which is a continuation-in-part of application No. 12/915,962, filed on Oct. 29, 2010, now Pat. No.

(Continued)

(51) Int. Cl.
*A61B 17/04* (2006.01)
*A61B 17/82* (2006.01)
(Continued)

(52) U.S. Cl.
CPC ............ *A61B 17/04* (2013.01); *A61B 17/0401* (2013.01); *A61B 17/823* (2013.01);
(Continued)

(58) Field of Classification Search
CPC ............... A61B 17/04; A61B 17/0401; A61B 17/0487; A61B 17/08869; A61B 17/8866; A61B 17/823; A61B 17/688; A61B 17/885; A61B 17/8861; A61B 17/0642; A61B 17/82; A61B 17/842; A61B 17/8076; A61B 17/683; A61B 17/0483; A61B 2017/0446; A61B 2017/0456; A61B 2017/0496; A61B 2017/0404; A61B 2017/00858; A61B 2017/06185; A61B 2017/0417

See application file for complete search history.

(56) References Cited

U.S. PATENT DOCUMENTS 65,499 A    6/1867   Miller
126,366 A   4/1872   Wills
(Continued)

FOREIGN PATENT DOCUMENTS

AU    4957264    3/1966
AU    440266     10/1967
(Continued)

OTHER PUBLICATIONS

"JuggerKnot™ Soft Anchor: Arthroscopic and Mini-Open Rotator Cuff Repair Using JuggerKnot™ Soft Anchor—2.9mm with ALLthread™ Knotless Anchor Surgical Technique" brochure, Biomet® Sports Medicine. (2013) 16 pages.

(Continued)

*Primary Examiner* — Dianne Dornbusch
(74) *Attorney, Agent, or Firm* — Schwegman Lundberg & Woessner, P.A.

(57) ABSTRACT

An apparatus can include a tensioning member having a body defining a first bone engaging surface, a second opposite suture receiving surface, and an outer perimeter. First and second suture attachment members can be positioned relative to the second surface and spaced apart from each other, and can be configured to be coupled to a suture. First and second suture engaging members can extend from the second surface and can be positioned in spaced relation to the first and second suture attachment members. Rotation of the tensioning member in a first direction can selectively engage the first and second suture receiving members with the suture, thereby forming a non-linear path of travel of the suture relative to the first and second suture attachment members and suture engaging members and increasing the tension in the suture.

31 Claims, 28 Drawing Sheets

Related U.S. Application Data 8,562,647, which is a continuation-in-part of application No. 12/719,337, filed on Mar. 8, 2010, now Pat. No. 9,078,644, which is a continuation-in-part of application No. 12/489,168, filed on Jun. 22, 2009, now Pat. No. 8,361,113, which is a continuation-in-part of application No. 12/474,802, filed on May 29, 2009, now Pat. No. 8,088,130, which is a continuation-in-part of application No. 12/196,405, filed on Aug. 22, 2008, now Pat. No. 8,128,658, and a continuation-in-part of application No. 12/196,407, filed on Aug. 22, 2008, now Pat. No. 8,137,382, and a continuation-in-part of application No. 12/196,410, filed on Aug. 22, 2008, now Pat. No. 8,118,836, and a continuation-in-part of application No. 11/541,506, filed on Sep. 29, 2006, now Pat. No. 7,601,165, application No. 13/295,126, which is a continuation-in-part of application No. 12/570,854, filed on Sep. 30, 2009, now Pat. No. 8,303,604, which is a continuation-in-part of application No. 12/014,399, filed on Jan. 15, 2008, now Pat. No. 7,909,851, which is a continuation-in-part of application No. 11/347,661, filed on Feb. 3, 2006, now Pat. No. 7,749,250, application No. 13/295,126, which is a continuation-in-part of application No. 12/029,861, filed on Feb. 12, 2008, now Pat. No. 8,251,998, which is a continuation-in-part of application No. 11/504,882, filed on Aug. 16, 2006, now Pat. No. 8,998,949, which is a continuation-in-part of application No. 11/408,282, filed on Apr. 20, 2006, now abandoned, application No. 13/295,126, which is a continuation-in-part of application No. 12/702,067, filed on Feb. 8, 2010, now Pat. No. 8,672,968, which is a continuation of application No. 11/541,505, filed on Sep. 29, 2006, now Pat. No. 7,658,751, application No. 13/295,126, which is a continuation-in-part of application No. 13/102,182, filed on May 6, 2011, now Pat. No. 8,231,654, which is a division of application No. 12/196,398, filed on Aug. 22, 2008, now Pat. No. 7,959,650, which is a continuation-in-part of application No. 11/784,821, filed on Apr. 10, 2007, now Pat. No. 9,017,381.

(51) Int. Cl.
*A61B 17/84* (2006.01)
*A61B 17/88* (2006.01)
*A61B 17/68* (2006.01)
*A61B 17/80* (2006.01)
*A61B 17/00* (2006.01)
*A61B 17/06* (2006.01)

(52) U.S. Cl.
CPC ............ *A61B17/842* (2013.01); *A61B 17/8869* (2013.01); *A61B 17/0483* (2013.01); *A61B 17/0487* (2013.01); *A61B 17/683* (2013.01); *A61B 17/809* (2013.01); *A61B 17/8076* (2013.01); *A61B 2017/00858* (2013.01); *A61B 2017/0404* (2013.01); *A61B 2017/0417* (2013.01); *A61B 2017/0496* (2013.01); *A61B 2017/06185* (2013.01)

(56) References Cited

U.S. PATENT DOCUMENTS

| | | |
|---|---|---|
| 233,475 A | 10/1880 | Cook et al. |
| 261,501 A | 7/1882 | Vandermark |
| 268,407 A | 12/1882 | Hughes |
| 394,739 A | 12/1888 | Toulmin |
| 417,805 A | 12/1889 | Beaman |
| 487,304 A | 12/1892 | Todd |
| 762,710 A | 6/1901 | Hall |
| 837,767 A | 12/1906 | Aims |
| 838,203 A | 12/1906 | Neil |
| 1,059,631 A | 4/1913 | Popovics |
| 1,131,155 A | 3/1915 | Murphy |
| 1,153,450 A | 9/1915 | Schaff |
| 1,346,940 A | 7/1920 | Collins |
| 1,635,066 A | 7/1927 | Wells |
| 401,677 A | 11/1933 | Roeder |
| 1,950,799 A | 3/1934 | Jones |
| 2,065,659 A | 12/1936 | Cullen |
| 2,108,206 A | 2/1938 | Meeker |
| 2,121,193 A | 6/1938 | Hanicke |
| 2,242,003 A | 5/1941 | Lorenzo |
| 2,267,925 A | 12/1941 | Johnston |
| 2,302,986 A | 11/1942 | Vollrath |
| 2,329,398 A | 9/1943 | Duffy |
| 2,397,216 A | 3/1946 | Stellin |
| RE22,857 E | 3/1947 | Ogburn |
| 2,526,959 A | 10/1950 | Lorenzo |
| 2,528,456 A | 10/1950 | Stevenson |
| 2,562,419 A | 7/1951 | Ferris |
| 2,581,564 A | 1/1952 | Villegas |
| 2,600,395 A | 6/1952 | Domoj et al. |
| 2,610,631 A | 9/1952 | Calicchio |
| 2,665,597 A | 1/1954 | Hill |
| 2,669,774 A | 2/1954 | Mitchell |
| 2,698,986 A | 1/1955 | Brown |
| 2,760,488 A | 8/1956 | Pierce |
| 2,833,284 A | 5/1958 | Springer |
| 2,846,712 A | 8/1958 | Markman |
| 2,860,393 A | 11/1958 | Brock |
| 2,880,728 A | 4/1959 | Rights |
| 2,881,762 A | 4/1959 | Lowrie |
| 2,883,096 A | 4/1959 | Dawson |
| 2,913,042 A | 11/1959 | Taylor |
| 3,000,009 A | 9/1961 | Selstad |
| 3,003,155 A | 10/1961 | Mielzynski et al. |
| 3,013,559 A | 12/1961 | Thomas |
| 3,037,619 A | 6/1962 | Stevans |
| 3,039,460 A | 6/1962 | Chandler |
| 3,081,781 A | 3/1963 | Stermer |
| 3,090,386 A | 5/1963 | Curtis |
| 3,103,666 A | 9/1963 | Bone |
| 3,123,077 A | 3/1964 | Alcamo |
| 3,125,095 A | 3/1964 | Kaufman et al. |
| 3,209,422 A | 10/1965 | Dritz |
| 3,234,938 A | 2/1966 | Robinson |
| 3,240,379 A | 3/1966 | Bremer et al. |
| 3,250,271 A | 5/1966 | Lippes |
| 3,399,432 A | 9/1968 | Merser |
| 3,409,014 A | 11/1968 | Shannon |
| RE26,501 E | 12/1968 | Kendrick et al. |
| 3,435,475 A | 4/1969 | Bisk |
| 3,467,089 A | 9/1969 | Hasson |
| 3,470,834 A | 10/1969 | Bone |
| 3,470,875 A | 10/1969 | Johnson |
| 3,500,820 A | 3/1970 | Almen |
| 3,507,274 A | 4/1970 | Soichet |
| 3,513,484 A | 5/1970 | Hausner |
| 3,515,132 A | 6/1970 | McKnight |
| 3,522,803 A | 8/1970 | Majzlin |
| 3,527,223 A | 9/1970 | Shein |
| 3,533,406 A | 10/1970 | Hutterer et al. |
| 3,541,591 A | 11/1970 | Hoegerman |
| 3,547,389 A | 12/1970 | Mitchell |
| 3,579,831 A | 5/1971 | Stevens et al. |
| 3,590,616 A | 7/1971 | Schussler et al. |
| 3,608,095 A | 9/1971 | Barry |
| 3,618,447 A | 11/1971 | Goins |
| 3,628,530 A | 12/1971 | Schwartz |
| 3,643,649 A | 2/1972 | Amato |
| 3,648,705 A | 3/1972 | Lary |
| 3,650,274 A * | 3/1972 | Edwards et al. ............ 606/233 |
| 3,656,483 A | 4/1972 | Rudel |
| 3,659,597 A | 5/1972 | Wolfers |

(56) References Cited

U.S. PATENT DOCUMENTS

| | | | |
|---|---|---|---|
| 3,664,345 | A | 5/1972 | Dabbs et al. |
| 3,665,560 | A | 5/1972 | Bennett et al. |
| 3,675,639 | A | 7/1972 | Cimber |
| 3,683,422 | A | 8/1972 | Stemmer et al. |
| 3,692,022 | A | 9/1972 | Ewing |
| 3,695,271 | A | 10/1972 | Chodorow |
| 3,699,969 | A | 10/1972 | Allen |
| 3,716,058 | A | 2/1973 | Tanner, Jr. |
| 3,744,488 | A | 7/1973 | Cox |
| 3,752,516 | A | 8/1973 | Mumma |
| 3,757,629 | A | 9/1973 | Schneider |
| 3,763,856 | A | 10/1973 | Blomberg |
| 3,771,520 | A | 11/1973 | Lerner |
| 3,777,748 | A | 12/1973 | Abramson |
| 3,807,407 | A | 4/1974 | Schweizer |
| 3,810,456 | A | 5/1974 | Karman |
| 3,825,010 | A | 7/1974 | McDonald |
| 3,840,017 | A | 10/1974 | Violante et al. |
| 3,842,824 | A | 10/1974 | Neufeld |
| 3,842,840 | A | 10/1974 | Schweizer |
| 3,845,772 | A | 11/1974 | Smith |
| 3,867,933 | A | 2/1975 | Kitrilakis |
| 3,867,944 | A | 2/1975 | Samuels |
| 3,871,368 | A | 3/1975 | Johnson et al. |
| 3,871,379 | A | 3/1975 | Clarke |
| 3,874,388 | A | 4/1975 | King et al. |
| 3,875,648 | A | 4/1975 | Bone |
| 3,877,570 | A | 4/1975 | Barry |
| 3,880,156 | A | 4/1975 | Hoff |
| 3,881,475 | A | 5/1975 | Gordon et al. |
| 3,889,666 | A | 6/1975 | Lerner |
| 3,892,240 | A | 7/1975 | Park |
| 3,896,500 | A | 7/1975 | Rambert et al. |
| 3,907,442 | A | 9/1975 | Reid |
| 3,910,281 | A | 10/1975 | Kletschka et al. |
| 3,918,444 | A | 11/1975 | Hoff et al. |
| 3,918,455 | A | 11/1975 | Coplan |
| 3,927,666 | A | 12/1975 | Hoff |
| 3,931,667 | A | 1/1976 | Merser et al. |
| 3,933,153 | A | 1/1976 | Csatary et al. |
| 3,937,217 | A | 2/1976 | Kosonen et al. |
| 3,943,932 | A | 3/1976 | Woo |
| 3,946,446 | A | 3/1976 | Schofield |
| 3,946,728 | A | 3/1976 | Bettex et al. |
| 3,946,740 | A | 3/1976 | Bassett |
| 3,953,896 | A | 5/1976 | Treace |
| 3,954,103 | A | 5/1976 | Garcia-Roel et al. |
| 3,961,632 | A | 6/1976 | Moossun |
| 3,973,560 | A | 8/1976 | Emmett et al. |
| 3,976,079 | A | 8/1976 | Samuels et al. |
| 3,977,050 | A | 8/1976 | Perez et al. |
| 3,979,799 | A | 9/1976 | Merser et al. |
| 3,985,138 | A | 10/1976 | Jarvik |
| 3,990,619 | A | 11/1976 | Russell |
| 4,005,707 | A | 2/1977 | Moulding, Jr. |
| 4,006,747 | A | 2/1977 | Kronenthal et al. |
| 4,007,743 | A | 2/1977 | Blake |
| 4,013,071 | A | 3/1977 | Rosenberg et al. |
| 4,026,281 | A | 5/1977 | Mayberry et al. |
| 4,036,101 | A | 7/1977 | Burnett |
| 4,050,100 | A | 9/1977 | Barry |
| 4,054,954 | A | 10/1977 | Nakayama et al. |
| 4,084,478 | A | 4/1978 | Simmons |
| 4,085,466 | A | 4/1978 | Goodfellow et al. |
| 4,094,313 | A | 6/1978 | Komamura et al. |
| 4,099,750 | A | 7/1978 | McGrew |
| 4,103,690 | A | 8/1978 | Harris |
| RE29,819 | E | 10/1978 | Bone |
| 4,121,487 | A | 10/1978 | Bone |
| 4,143,656 | A | 3/1979 | Holmes et al. |
| 4,144,876 | A | 3/1979 | DeLeo |
| 4,146,022 | A | 3/1979 | Johnson et al. |
| 4,149,277 | A | 4/1979 | Bokros |
| 4,157,714 | A | 6/1979 | Foltz et al. |
| 4,158,250 | A | 6/1979 | Ringwald |
| 4,160,453 | A | 7/1979 | Miller |
| 4,164,225 | A | 8/1979 | Johnson et al. |
| 4,172,458 | A | 10/1979 | Pereyra |
| 4,175,555 | A | 11/1979 | Herbert et al. |
| 4,185,636 | A | 1/1980 | Gabbay et al. |
| 4,196,883 | A | 4/1980 | Einhorn et al. |
| 4,210,148 | A | 7/1980 | Stivala |
| 4,235,161 | A | 11/1980 | Kunreuther |
| 4,235,238 | A | 11/1980 | Ogiu et al. |
| 4,237,779 | A | 12/1980 | Kunreuther |
| 4,243,037 | A | 1/1981 | Smith |
| 4,249,525 | A | 2/1981 | Krzeminski |
| 4,263,913 | A | 4/1981 | Malmin |
| 4,265,246 | A | 5/1981 | Barry |
| 4,273,117 | A | 6/1981 | Neuhauser et al. |
| 4,275,490 | A | 6/1981 | Bivins |
| 4,275,717 | A | 6/1981 | Bolesky |
| 4,287,807 | A | 9/1981 | Pacharis et al. |
| 4,291,698 | A | 9/1981 | Fuchs et al. |
| 4,301,551 | A | 11/1981 | Dore et al. |
| 4,307,723 | A | 12/1981 | Finney |
| 4,312,337 | A | 1/1982 | Donohue |
| 4,316,469 | A | 2/1982 | Kapitanov et al. |
| 4,326,531 | A | 4/1982 | Shimonaka et al. |
| 4,345,601 | A | 8/1982 | Fukuda |
| 4,349,027 | A | 9/1982 | DiFrancesco |
| 4,388,921 | A | 6/1983 | Sutter et al. |
| 4,400,833 | A | 8/1983 | Kurland |
| 4,402,445 | A | 9/1983 | Green |
| 4,409,974 | A | 10/1983 | Freedland |
| 4,438,769 | A | 3/1984 | Pratt et al. |
| 4,441,489 | A | 4/1984 | Evans et al. |
| 4,454,875 | A | 6/1984 | Pratt et al. |
| 4,462,395 | A | 7/1984 | Johnson |
| 4,463,753 | A | 8/1984 | Gustilo |
| 4,473,102 | A | 9/1984 | Ohman et al. |
| 4,484,570 | A | 11/1984 | Sutter et al. |
| 4,489,446 | A | 12/1984 | Reed |
| 4,489,464 | A | 12/1984 | Massari et al. |
| 4,493,323 | A | 1/1985 | Albright et al. |
| 4,496,468 | A | 1/1985 | House et al. |
| 4,505,274 | A | 3/1985 | Speelman |
| 4,509,516 | A | 4/1985 | Richmond |
| 4,531,522 | A | 7/1985 | Bedi et al. |
| 4,532,926 | A | 8/1985 | O'Holla |
| 4,534,350 | A | 8/1985 | Golden et al. |
| 4,535,764 | A | 8/1985 | Ebert |
| 4,537,185 | A | 8/1985 | Stednitz |
| 4,549,545 | A | 10/1985 | Levy |
| 4,549,652 | A | 10/1985 | Free |
| 4,561,432 | A | 12/1985 | Mazor |
| 4,564,007 | A | 1/1986 | Coombs et al. |
| 4,570,623 | A | 2/1986 | Ellison et al. |
| 4,573,844 | A | 3/1986 | Smith |
| 4,576,608 | A | 3/1986 | Homsy |
| 4,584,722 | A | 4/1986 | Levy et al. |
| 4,587,963 | A | 5/1986 | Leibinger et al. |
| 4,590,928 | A | 5/1986 | Hunt et al. |
| 4,595,007 | A | 6/1986 | Mericle |
| 4,596,249 | A | 6/1986 | Freda et al. |
| 4,602,635 | A | 7/1986 | Mulhollan et al. |
| 4,602,636 | A | 7/1986 | Noiles |
| 4,604,997 | A | 8/1986 | De Bastiani et al. |
| 4,605,414 | A | 8/1986 | Czajka |
| 4,616,650 | A | 10/1986 | Green et al. |
| 4,621,640 | A | 11/1986 | Mulhollan et al. |
| 4,624,254 | A | 11/1986 | McGarry et al. |
| 4,632,100 | A | 12/1986 | Somers et al. |
| 4,635,637 | A | 1/1987 | Schreiber |
| 4,636,121 | A | 1/1987 | Miller |
| 4,641,652 | A | 2/1987 | Hutterer et al. |
| 4,649,952 | A | 3/1987 | Jobe |
| 4,653,486 | A | 3/1987 | Coker |
| 4,653,487 | A | 3/1987 | Maale |
| 4,653,489 | A | 3/1987 | Tronzo |
| 4,655,777 | A | 4/1987 | Dunn et al. |
| 4,662,068 | A | 5/1987 | Polonsky |
| 4,667,662 | A | 5/1987 | Titone et al. |
| 4,667,675 | A | 5/1987 | Davis |

(56) References Cited

U.S. PATENT DOCUMENTS

| | | |
|---|---|---|
| 4,669,473 A | 6/1987 | Richards et al. |
| 4,683,895 A | 8/1987 | Pohndorf |
| 4,688,561 A | 8/1987 | Reese |
| 4,690,169 A | 9/1987 | Jobe |
| 4,696,300 A | 9/1987 | Anderson |
| 4,705,040 A | 11/1987 | Mueller et al. |
| 4,708,132 A | 11/1987 | Silvestrini |
| 4,714,475 A | 12/1987 | Grundei et al. |
| 4,716,893 A | 1/1988 | Fischer et al. |
| 4,719,671 A | 1/1988 | Ito et al. |
| 4,719,917 A | 1/1988 | Barrows et al. |
| 4,723,540 A | 2/1988 | Gilmer, Jr. |
| 4,724,839 A | 2/1988 | Bedi et al. |
| 4,728,332 A | 3/1988 | Albrektsson |
| 4,738,255 A | 4/1988 | Goble et al. |
| 4,741,330 A | 5/1988 | Hayhurst |
| 4,741,336 A | 5/1988 | Failla et al. |
| 4,744,353 A | 5/1988 | McFarland |
| 4,744,793 A | 5/1988 | Parr et al. |
| 4,750,492 A | 6/1988 | Jacobs |
| 4,760,843 A | 8/1988 | Fischer et al. |
| 4,760,844 A | 8/1988 | Kyle |
| 4,760,848 A | 8/1988 | Hasson |
| 4,770,663 A | 9/1988 | Hanslik et al. |
| 4,772,261 A | 9/1988 | Von Hoff et al. |
| 4,772,286 A | 9/1988 | Goble et al. |
| 4,773,910 A | 9/1988 | Chen et al. |
| 4,775,380 A | 10/1988 | Seedhom et al. |
| 4,776,328 A | 10/1988 | Frey et al. |
| 4,781,190 A | 11/1988 | Lee et al. |
| 4,784,126 A | 11/1988 | Hourahane et al. |
| 4,787,882 A | 11/1988 | Claren et al. |
| 4,790,297 A | 12/1988 | Luque et al. |
| 4,793,363 A | 12/1988 | Ausherman et al. |
| 4,809,695 A | 3/1989 | Gwathmey et al. |
| 4,813,406 A | 3/1989 | Ogle, II |
| 4,823,794 A | 4/1989 | Pierce |
| 4,828,562 A | 5/1989 | Kenna |
| 4,832,026 A | 5/1989 | Jones |
| 4,834,098 A | 5/1989 | Jones |
| 4,838,282 A | 6/1989 | Strasser et al. |
| 4,841,960 A | 6/1989 | Garner |
| 4,851,005 A | 7/1989 | Hunt et al. |
| 4,858,608 A | 8/1989 | McQuilkin et al. |
| 4,860,513 A | 8/1989 | Whitman |
| 4,863,383 A | 9/1989 | Grafelmann et al. |
| 4,870,957 A | 10/1989 | Goble et al. |
| 4,873,976 A | 10/1989 | Schreiber |
| 4,887,601 A | 12/1989 | Richards |
| 4,889,110 A | 12/1989 | Galline et al. |
| 4,890,615 A | 1/1990 | Caspari et al. |
| 4,893,619 A | 1/1990 | Dale et al. |
| 4,893,974 A | 1/1990 | Fischer et al. |
| 4,895,148 A | 1/1990 | Bays et al. |
| 4,896,668 A | 1/1990 | Popoff et al. |
| 4,898,156 A | 2/1990 | Gatturna et al. |
| 4,899,743 A | 2/1990 | Nicholson et al. |
| 4,901,721 A | 2/1990 | Hakki |
| 4,923,461 A | 5/1990 | Caspari et al. |
| 4,927,421 A | 5/1990 | Goble et al. |
| 4,946,377 A | 8/1990 | Kovach |
| 4,946,468 A | 8/1990 | Li |
| 4,950,270 A | 8/1990 | Bowman et al. |
| 4,950,285 A | 8/1990 | Wilk |
| 4,960,381 A | 10/1990 | Niznick |
| 4,961,741 A | 10/1990 | Hayhurst |
| 4,968,315 A | 11/1990 | Gatturna |
| 4,968,317 A | 11/1990 | Tormala et al. |
| 4,969,886 A | 11/1990 | Cziffer et al. |
| 4,976,736 A | 12/1990 | White et al. |
| 4,978,350 A | 12/1990 | Wagenknecht et al. |
| 4,979,956 A | 12/1990 | Silvestrini |
| 4,983,176 A | 1/1991 | Cushman et al. |
| 4,988,351 A | 1/1991 | Paulos et al. |
| 4,994,074 A | 2/1991 | Bezwada et al. |
| 4,997,433 A | 3/1991 | Goble et al. |
| 5,002,550 A | 3/1991 | Li |
| 5,002,562 A | 3/1991 | Oberlander |
| 5,007,921 A | 4/1991 | Brown |
| 5,030,224 A | 7/1991 | Wright et al. |
| 5,030,235 A | 7/1991 | Campbell, Jr. |
| 5,037,422 A | 8/1991 | Hayhurst et al. |
| 5,041,129 A | 8/1991 | Hayhurst et al. |
| 5,046,513 A | 9/1991 | Gatturna et al. |
| 5,047,030 A | 9/1991 | Draenert et al. |
| 5,053,046 A | 10/1991 | Janese |
| 5,053,047 A | 10/1991 | Yoon |
| 5,059,201 A | 10/1991 | Asnis |
| 5,059,206 A | 10/1991 | Winters |
| 5,061,277 A | 10/1991 | Carpentier et al. |
| 5,062,344 A | 11/1991 | Gerker |
| 5,062,843 A | 11/1991 | Mahony, III |
| 5,064,431 A | 11/1991 | Gilbertson et al. |
| 5,074,874 A | 12/1991 | Yoon et al. |
| 5,078,731 A | 1/1992 | Hayhurst |
| 5,078,843 A | 1/1992 | Pratt |
| 5,084,050 A | 1/1992 | Draenert |
| 5,084,058 A | 1/1992 | Li |
| 5,085,661 A | 2/1992 | Moss |
| 5,087,263 A | 2/1992 | Li |
| 5,089,012 A | 2/1992 | Prou |
| 5,092,866 A | 3/1992 | Breard et al. |
| 5,098,435 A | 3/1992 | Stednitz et al. |
| 5,100,415 A | 3/1992 | Hayhurst |
| 5,100,417 A | 3/1992 | Cerier et al. |
| 5,108,433 A * | 4/1992 | May et al. .................. 623/13.13 |
| 5,116,337 A | 5/1992 | Johnson |
| 5,116,373 A | 5/1992 | Jakob et al. |
| 5,116,375 A | 5/1992 | Hofmann |
| 5,123,913 A | 6/1992 | Wilk et al. |
| 5,123,914 A | 6/1992 | Cope |
| 5,127,785 A | 7/1992 | Faucher et al. |
| 5,129,901 A | 7/1992 | Decoste |
| 5,129,902 A | 7/1992 | Goble et al. |
| 5,129,904 A | 7/1992 | Illi et al. |
| 5,129,906 A | 7/1992 | Ross et al. |
| 5,139,498 A | 8/1992 | Astudillo Ley |
| 5,139,499 A | 8/1992 | Small et al. |
| 5,139,520 A | 8/1992 | Rosenberg |
| 5,143,498 A | 9/1992 | Whitman |
| 5,147,362 A | 9/1992 | Goble |
| 5,149,329 A | 9/1992 | Richardson |
| 5,151,104 A | 9/1992 | Kenna |
| 5,152,790 A | 10/1992 | Rosenberg et al. |
| 5,154,189 A | 10/1992 | Oberlander |
| 5,156,616 A | 10/1992 | Meadows et al. |
| 5,163,960 A | 11/1992 | Bonutti |
| D331,626 S | 12/1992 | Hayhurst et al. |
| 5,169,400 A | 12/1992 | Muhling et al. |
| 5,176,682 A | 1/1993 | Chow |
| 5,178,629 A | 1/1993 | Kammerer |
| 5,183,458 A | 2/1993 | Marx |
| 5,190,545 A | 3/1993 | Corsi et al. |
| 5,192,282 A | 3/1993 | Draenert et al. |
| 5,197,987 A | 3/1993 | Koch et al. |
| 5,199,135 A | 4/1993 | Gold |
| 5,203,784 A | 4/1993 | Ross et al. |
| 5,203,787 A | 4/1993 | Noblitt et al. |
| 5,207,679 A | 5/1993 | Li |
| 5,209,753 A | 5/1993 | Biedermann et al. |
| 5,209,805 A | 5/1993 | Spraggins |
| 5,211,647 A | 5/1993 | Schmieding |
| 5,211,650 A | 5/1993 | Noda |
| 5,214,987 A | 6/1993 | Fenton, Sr. |
| 5,219,359 A | 6/1993 | McQuilkin et al. |
| 5,222,976 A | 6/1993 | Yoon |
| 5,224,946 A | 7/1993 | Hayhurst et al. |
| 5,230,699 A | 7/1993 | Grasinger |
| 5,232,436 A | 8/1993 | Janevski |
| 5,234,435 A | 8/1993 | Seagrave, Jr. |
| 5,235,238 A | 8/1993 | Nomura et al. |
| 5,236,445 A | 8/1993 | Hayhurst et al. |
| 5,236,461 A | 8/1993 | Forte |
| 5,242,447 A | 9/1993 | Borzone |

(56) References Cited

U.S. PATENT DOCUMENTS

| | | |
|---|---|---|
| 5,246,441 A | 9/1993 | Ross et al. |
| 5,249,899 A | 10/1993 | Wilson |
| 5,250,053 A | 10/1993 | Snyder |
| 5,258,015 A | 11/1993 | Li et al. |
| 5,258,016 A | 11/1993 | DiPoto et al. |
| 5,258,040 A | 11/1993 | Bruchman et al. |
| 5,261,908 A | 11/1993 | Campbell, Jr. |
| 5,268,001 A | 12/1993 | Nicholson et al. |
| 5,269,160 A | 12/1993 | Wood |
| 5,269,783 A | 12/1993 | Sander |
| 5,269,806 A | 12/1993 | Sardelis et al. |
| 5,269,809 A | 12/1993 | Hayhurst et al. |
| 5,279,311 A | 1/1994 | Snyder |
| 5,281,422 A | 1/1994 | Badylak et al. |
| 5,282,809 A | 2/1994 | Kammerer et al. |
| 5,282,832 A | 2/1994 | Toso et al. |
| 5,282,867 A | 2/1994 | Mikhail |
| 5,285,040 A | 2/1994 | Brandberg et al. |
| 5,290,217 A | 3/1994 | Campos |
| 5,290,243 A | 3/1994 | Chodorow et al. |
| 5,306,301 A | 4/1994 | Graf et al. |
| 5,312,422 A | 5/1994 | Trott |
| 5,312,438 A | 5/1994 | Johnson |
| 5,318,566 A | 6/1994 | Miller |
| 5,318,575 A | 6/1994 | Chesterfield et al. |
| 5,318,577 A | 6/1994 | Li |
| 5,318,578 A | 6/1994 | Hasson |
| 5,320,115 A | 6/1994 | Kenna |
| 5,320,626 A | 6/1994 | Schmieding |
| 5,320,633 A | 6/1994 | Allen et al. |
| 5,324,308 A | 6/1994 | Pierce |
| 5,330,489 A | 7/1994 | Green et al. |
| 5,333,625 A | 8/1994 | Klein |
| 5,334,204 A | 8/1994 | Clewett et al. |
| 5,336,229 A | 8/1994 | Noda |
| 5,336,231 A | 8/1994 | Adair |
| 5,336,240 A | 8/1994 | Metzler et al. |
| 5,339,870 A | 8/1994 | Green et al. |
| 5,342,369 A | 8/1994 | Harryman, II |
| 5,346,462 A | 9/1994 | Barber |
| 5,354,292 A | 10/1994 | Braeuer et al. |
| 5,354,298 A | 10/1994 | Lee et al. |
| 5,356,412 A | 10/1994 | Golds et al. |
| 5,356,413 A | 10/1994 | Martins et al. |
| 5,356,417 A | 10/1994 | Golds |
| 5,358,511 A | 10/1994 | Gatturna et al. |
| 5,360,431 A | 11/1994 | Puno et al. |
| 5,362,294 A | 11/1994 | Seitzinger |
| 5,364,400 A | 11/1994 | Rego, Jr. et al. |
| 5,366,461 A | 11/1994 | Blasnik |
| 5,368,599 A | 11/1994 | Hirsch et al. |
| 5,370,661 A | 12/1994 | Branch |
| 5,370,662 A | 12/1994 | Stone et al. |
| 5,372,146 A | 12/1994 | Branch |
| 5,372,604 A | 12/1994 | Trott |
| 5,372,821 A | 12/1994 | Badylak et al. |
| 5,374,268 A | 12/1994 | Sander |
| 5,379,492 A | 1/1995 | Glesser |
| 5,383,878 A | 1/1995 | Roger et al. |
| 5,383,904 A | 1/1995 | Totakura et al. |
| 5,391,171 A | 2/1995 | Schmieding |
| 5,391,176 A | 2/1995 | de la Torre |
| 5,391,182 A | 2/1995 | Chin |
| 5,393,302 A | 2/1995 | Clark et al. |
| RE34,871 E | 3/1995 | McGuire et al. |
| 5,395,374 A | 3/1995 | Miller et al. |
| 5,397,356 A | 3/1995 | Goble et al. |
| 5,403,328 A | 4/1995 | Shallman |
| 5,403,329 A | 4/1995 | Hinchliffe |
| 5,403,348 A | 4/1995 | Bonutti |
| 5,405,359 A | 4/1995 | Pierce |
| 5,411,550 A | 5/1995 | Herweck et al. |
| 5,415,658 A | 5/1995 | Kilpela et al. |
| 5,417,690 A | 5/1995 | Sennett et al. |
| 5,417,691 A | 5/1995 | Hayhurst |
| 5,417,698 A | 5/1995 | Green et al. |
| 5,417,712 A | 5/1995 | Whittaker et al. |
| 5,423,819 A | 6/1995 | Small et al. |
| 5,423,821 A | 6/1995 | Pasque |
| 5,423,823 A | 6/1995 | Schmieding |
| 5,423,860 A | 6/1995 | Lizardi et al. |
| 5,425,733 A | 6/1995 | Schmieding |
| 5,425,766 A | 6/1995 | Bowald et al. |
| 5,433,751 A | 7/1995 | Christel et al. |
| 5,437,680 A | 8/1995 | Yoon |
| 5,437,685 A | 8/1995 | Blasnik |
| 5,439,684 A | 8/1995 | Prewett et al. |
| 5,441,508 A | 8/1995 | Gazielly et al. |
| 5,443,468 A | 8/1995 | Johnson |
| 5,443,482 A | 8/1995 | Stone et al. |
| 5,443,483 A | 8/1995 | Kirsch et al. |
| 5,443,509 A | 8/1995 | Boucher et al. |
| 5,445,833 A | 8/1995 | Badylak et al. |
| 5,447,512 A | 9/1995 | Wilson et al. |
| 5,449,361 A | 9/1995 | Preissman |
| 5,451,203 A | 9/1995 | Lamb |
| 5,454,811 A | 10/1995 | Huebner |
| 5,454,821 A | 10/1995 | Harm et al. |
| 5,456,685 A | 10/1995 | Huebner |
| 5,456,722 A | 10/1995 | McLeod et al. |
| 5,458,601 A | 10/1995 | Young, Jr. et al. |
| 5,458,604 A | 10/1995 | Schmieding |
| 5,462,542 A | 10/1995 | Alesi, Jr. |
| 5,462,560 A | 10/1995 | Stevens |
| 5,464,426 A | 11/1995 | Bonutti |
| 5,464,427 A | 11/1995 | Curtis et al. |
| 5,464,440 A | 11/1995 | Johansson et al. |
| 5,466,237 A | 11/1995 | Byrd, III et al. |
| 5,467,786 A | 11/1995 | Allen et al. |
| 5,470,334 A | 11/1995 | Ross et al. |
| 5,470,337 A | 11/1995 | Moss |
| 5,470,338 A | 11/1995 | Whitfield et al. |
| 5,472,452 A | 12/1995 | Trott |
| 5,474,565 A | 12/1995 | Trott |
| 5,474,568 A | 12/1995 | Scott |
| 5,474,572 A | 12/1995 | Hayhurst |
| 5,476,465 A | 12/1995 | Preissman |
| 5,478,344 A | 12/1995 | Stone et al. |
| 5,478,345 A | 12/1995 | Stone et al. |
| 5,480,403 A | 1/1996 | Lee et al. |
| 5,480,406 A | 1/1996 | Nolan et al. |
| 5,484,442 A | 1/1996 | Melker et al. |
| 5,486,197 A | 1/1996 | Le et al. |
| 5,490,750 A | 2/1996 | Gundy |
| 5,496,331 A | 3/1996 | Xu et al. |
| 5,496,348 A | 3/1996 | Bonutti |
| 5,500,000 A | 3/1996 | Feagin et al. |
| 5,505,736 A | 4/1996 | Reimels et al. |
| 5,507,754 A | 4/1996 | Green et al. |
| 5,520,691 A | 5/1996 | Branch |
| 5,520,700 A | 5/1996 | Beyar et al. |
| 5,520,702 A | 5/1996 | Sauer et al. |
| 5,522,817 A | 6/1996 | Sander et al. |
| 5,522,820 A | 6/1996 | Caspari et al. |
| 5,522,844 A | 6/1996 | Johnson |
| 5,522,845 A | 6/1996 | Wenstrom, Jr. |
| 5,522,846 A | 6/1996 | Bonutti |
| 5,524,946 A | 6/1996 | Thompson |
| 5,527,321 A | 6/1996 | Hinchliffe |
| 5,527,342 A | 6/1996 | Pietrzak et al. |
| 5,527,343 A | 6/1996 | Bonutti |
| 5,534,012 A | 7/1996 | Bonutti |
| 5,536,270 A | 7/1996 | Songer et al. |
| 5,540,698 A | 7/1996 | Preissman |
| 5,540,703 A | 7/1996 | Barker, Jr. et al. |
| 5,540,718 A | 7/1996 | Bartlett |
| 5,545,168 A | 8/1996 | Burke |
| 5,545,178 A | 8/1996 | Kensey et al. |
| 5,545,180 A | 8/1996 | Le et al. |
| 5,545,228 A | 8/1996 | Kambin |
| 5,549,613 A | 8/1996 | Goble et al. |
| 5,549,617 A | 8/1996 | Green et al. |
| 5,549,619 A | 8/1996 | Peters et al. |
| 5,549,630 A | 8/1996 | Bonutti |

(56) References Cited

U.S. PATENT DOCUMENTS

| | | |
|---|---|---|
| 5,549,631 A | 8/1996 | Bonutti |
| 5,562,683 A | 10/1996 | Chan |
| 5,562,685 A | 10/1996 | Mollenauer et al. |
| 5,562,686 A | 10/1996 | Sauer et al. |
| 5,569,269 A | 10/1996 | Hart et al. |
| 5,569,305 A | 10/1996 | Bonutti |
| 5,571,090 A | 11/1996 | Sherts |
| 5,571,139 A | 11/1996 | Jenkins, Jr. |
| 5,572,655 A | 11/1996 | Tuljapurkar et al. |
| 5,573,286 A | 11/1996 | Rogozinski |
| 5,573,542 A | 11/1996 | Stevens |
| 5,573,548 A | 11/1996 | Nazre et al. |
| 5,577,299 A | 11/1996 | Thompson et al. |
| 5,578,057 A | 11/1996 | Wenstrom, Jr. |
| 5,584,695 A | 12/1996 | Lal Sachdeva et al. |
| 5,584,835 A | 12/1996 | Greenfield |
| 5,584,836 A | 12/1996 | Ballintyn et al. |
| 5,584,862 A | 12/1996 | Bonutti |
| 5,586,986 A | 12/1996 | Hinchliffe |
| 5,588,575 A | 12/1996 | Davignon |
| 5,591,180 A | 1/1997 | Hinchliffe |
| 5,591,181 A | 1/1997 | Stone et al. |
| 5,591,207 A | 1/1997 | Coleman |
| 5,593,407 A | 1/1997 | Reis et al. |
| 5,593,425 A | 1/1997 | Bonutti et al. |
| 5,601,557 A | 2/1997 | Hayhurst |
| 5,601,559 A | 2/1997 | Melker et al. |
| 5,601,571 A | 2/1997 | Moss |
| 5,603,716 A | 2/1997 | Morgan et al. |
| 5,607,429 A | 3/1997 | Hayano et al. |
| 5,607,430 A | 3/1997 | Bailey |
| 5,618,290 A | 4/1997 | Toy et al. |
| 5,626,611 A | 5/1997 | Liu et al. |
| 5,626,614 A | 5/1997 | Hart |
| 5,628,756 A | 5/1997 | Barker, Jr. et al. |
| 5,628,766 A | 5/1997 | Johnson |
| 5,630,824 A | 5/1997 | Hart |
| 5,632,748 A | 5/1997 | Beck, Jr. et al. |
| 5,641,256 A | 6/1997 | Gundy |
| 5,643,266 A | 7/1997 | Li |
| 5,643,269 A | 7/1997 | Harle et al. |
| 5,643,295 A | 7/1997 | Yoon |
| 5,643,319 A | 7/1997 | Green et al. |
| 5,643,320 A | 7/1997 | Lower et al. |
| 5,643,321 A | 7/1997 | McDevitt |
| 5,645,546 A | 7/1997 | Fard |
| 5,645,547 A | 7/1997 | Coleman |
| 5,645,568 A | 7/1997 | Chervitz et al. |
| 5,645,588 A | 7/1997 | Graf et al. |
| 5,647,874 A | 7/1997 | Hayhurst |
| 5,649,959 A | 7/1997 | Hannam et al. |
| 5,649,960 A * | 7/1997 | Pavletic ............... 606/216 |
| 5,649,963 A | 7/1997 | McDevitt |
| 5,658,289 A | 8/1997 | Boucher et al. |
| 5,658,299 A | 8/1997 | Hart |
| 5,658,313 A | 8/1997 | Thal |
| 5,662,658 A | 9/1997 | Wenstrom, Jr. |
| 5,662,663 A | 9/1997 | Shallman |
| 5,662,681 A | 9/1997 | Nash et al. |
| 5,665,112 A | 9/1997 | Thal |
| 5,667,513 A | 9/1997 | Torrie et al. |
| 5,671,695 A | 9/1997 | Schroeder |
| 5,674,224 A | 10/1997 | Howell et al. |
| 5,679,723 A | 10/1997 | Cooper et al. |
| 5,681,334 A | 10/1997 | Evans et al. |
| 5,681,352 A | 10/1997 | Clancy, III et al. |
| 5,683,404 A | 11/1997 | Johnson |
| 5,683,419 A | 11/1997 | Thal |
| 5,688,285 A | 11/1997 | Yamada et al. |
| 5,690,676 A | 11/1997 | DiPoto et al. |
| 5,690,678 A | 11/1997 | Johnson |
| 5,693,046 A | 12/1997 | Songer et al. |
| 5,695,497 A | 12/1997 | Stahelin et al. |
| 5,697,929 A | 12/1997 | Mellinger |
| 5,699,657 A | 12/1997 | Paulson |
| 5,702,397 A | 12/1997 | Goble et al. |
| 5,702,422 A | 12/1997 | Stone |
| 5,702,462 A | 12/1997 | Oberlander |
| 5,707,373 A | 1/1998 | Sevrain et al. |
| 5,709,708 A | 1/1998 | Thal |
| 5,711,969 A | 1/1998 | Patel et al. |
| 5,713,005 A | 1/1998 | Proebsting |
| 5,713,904 A | 2/1998 | Errico et al. |
| 5,713,905 A | 2/1998 | Goble et al. |
| 5,713,921 A | 2/1998 | Bonutti |
| 5,715,578 A | 2/1998 | Knudson |
| 5,716,359 A | 2/1998 | Ojima et al. |
| 5,716,397 A | 2/1998 | Myers |
| 5,718,717 A | 2/1998 | Bonutti |
| 5,720,747 A | 2/1998 | Burke |
| 5,720,765 A | 2/1998 | Thal |
| 5,720,766 A | 2/1998 | Zang et al. |
| 5,722,976 A | 3/1998 | Brown |
| 5,725,529 A | 3/1998 | Nicholson et al. |
| 5,725,549 A | 3/1998 | Lam |
| 5,725,556 A | 3/1998 | Moser et al. |
| 5,725,581 A | 3/1998 | Brånemark et al. |
| 5,725,582 A | 3/1998 | Bevan et al. |
| 5,726,722 A | 3/1998 | Uehara et al. |
| 5,728,107 A | 3/1998 | Zlock et al. |
| 5,728,109 A | 3/1998 | Schulze et al. |
| 5,728,136 A | 3/1998 | Thal |
| 5,733,293 A | 3/1998 | Scirica et al. |
| 5,733,306 A | 3/1998 | Bonutti |
| 5,733,307 A | 3/1998 | Dinsdale |
| 5,735,875 A | 4/1998 | Bonutti et al. |
| 5,741,259 A | 4/1998 | Chan |
| 5,741,260 A | 4/1998 | Songer et al. |
| 5,741,281 A | 4/1998 | Martin et al. |
| 5,743,912 A | 4/1998 | Lahille et al. |
| 5,746,751 A | 5/1998 | Sherts |
| 5,746,752 A | 5/1998 | Burkhart |
| 5,746,754 A | 5/1998 | Chan |
| 5,749,898 A | 5/1998 | Schulze et al. |
| 5,755,729 A | 5/1998 | de la Torre et al. |
| 5,755,791 A | 5/1998 | Whitson et al. |
| 5,766,176 A | 6/1998 | Duncan |
| 5,766,218 A | 6/1998 | Arnott |
| 5,766,250 A | 6/1998 | Chervitz et al. |
| 5,769,894 A | 6/1998 | Ferragamo |
| 5,769,899 A | 6/1998 | Schwartz et al. |
| 5,772,673 A | 6/1998 | Cuny et al. |
| 5,776,196 A | 7/1998 | Matsuzaki et al. |
| 5,782,845 A | 7/1998 | Shewchuk |
| 5,782,862 A | 7/1998 | Bonutti |
| 5,782,864 A | 7/1998 | Lizardi |
| 5,782,866 A | 7/1998 | Wenstrom, Jr. |
| 5,785,714 A | 7/1998 | Morgan et al. |
| 5,792,142 A | 8/1998 | Galitzer |
| 5,792,149 A | 8/1998 | Sherts et al. |
| 5,796,127 A | 8/1998 | Hayafuji et al. |
| 5,797,913 A | 8/1998 | Dambreville et al. |
| 5,797,915 A | 8/1998 | Pierson, III et al. |
| 5,797,916 A | 8/1998 | McDowell |
| 5,797,928 A | 8/1998 | Kogasaka |
| 5,800,407 A | 9/1998 | Eldor et al. |
| 5,810,824 A | 9/1998 | Chan |
| 5,810,848 A | 9/1998 | Hayhurst |
| 5,814,069 A | 9/1998 | Schulze et al. |
| 5,814,070 A | 9/1998 | Borzone et al. |
| 5,814,072 A | 9/1998 | Bonutti |
| 5,814,073 A | 9/1998 | Bonutti |
| 5,823,980 A | 10/1998 | Kopfer |
| 5,824,011 A | 10/1998 | Stone et al. |
| 5,830,234 A | 11/1998 | Wojciechowicz et al. |
| 5,843,084 A | 12/1998 | Hart et al. |
| 5,845,645 A | 12/1998 | Bonutti |
| 5,846,254 A | 12/1998 | Schulze et al. |
| 5,848,983 A | 12/1998 | Basaj et al. |
| 5,849,012 A | 12/1998 | Abboudi |
| 5,860,973 A | 1/1999 | Michelson |
| 5,868,740 A | 2/1999 | LeVeen et al. |
| 5,868,748 A | 2/1999 | Burke |
| 5,868,789 A | 2/1999 | Huebner |

(56) References Cited

U.S. PATENT DOCUMENTS

| | | |
|---|---|---|
| 5,871,484 A | 2/1999 | Spievack et al. |
| 5,871,486 A | 2/1999 | Huebner et al. |
| 5,871,490 A | 2/1999 | Schulze et al. |
| 5,885,294 A | 3/1999 | Pedlick et al. |
| 5,891,168 A | 4/1999 | Thal |
| 5,893,592 A | 4/1999 | Schulze et al. |
| 5,895,395 A | 4/1999 | Yeung |
| 5,897,564 A | 4/1999 | Schulze et al. |
| 5,897,574 A | 4/1999 | Bonutti |
| 5,899,902 A | 5/1999 | Brown et al. |
| 5,899,938 A | 5/1999 | Sklar et al. |
| 5,908,421 A | 6/1999 | Beger et al. |
| 5,908,436 A | 6/1999 | Cuschieri et al. |
| 5,910,148 A | 6/1999 | Reimels et al. |
| 5,911,721 A | 6/1999 | Nicholson et al. |
| 5,918,604 A | 7/1999 | Whelan |
| 5,921,986 A | 7/1999 | Bonutti |
| 5,925,008 A | 7/1999 | Douglas |
| 5,928,231 A | 7/1999 | Klein et al. |
| 5,928,267 A | 7/1999 | Bonutti et al. |
| RE36,289 E | 8/1999 | Le et al. |
| 5,931,838 A | 8/1999 | Vito |
| 5,931,844 A | 8/1999 | Thompson et al. |
| 5,931,869 A | 8/1999 | Boucher et al. |
| 5,935,119 A | 8/1999 | Guy et al. |
| 5,935,133 A | 8/1999 | Wagner et al. |
| 5,935,149 A | 8/1999 | Ek |
| 5,938,668 A | 8/1999 | Scirica et al. |
| 5,941,439 A | 8/1999 | Kammerer et al. |
| 5,941,900 A | 8/1999 | Bonutti |
| 5,944,739 A | 8/1999 | Zlock et al. |
| 5,946,783 A | 9/1999 | Plociennik et al. |
| 5,947,915 A | 9/1999 | Thibodo, Jr. |
| 5,947,982 A | 9/1999 | Duran |
| 5,947,999 A | 9/1999 | Groiso |
| 5,948,002 A | 9/1999 | Bonutti |
| 5,951,559 A | 9/1999 | Burkhart |
| 5,951,560 A | 9/1999 | Simon et al. |
| 5,954,747 A | 9/1999 | Clark |
| 5,957,953 A | 9/1999 | DiPoto et al. |
| 5,961,521 A | 10/1999 | Roger et al. |
| 5,961,524 A | 10/1999 | Crombie |
| 5,964,764 A | 10/1999 | West, Jr. et al. |
| 5,964,767 A | 10/1999 | Tapia et al. |
| 5,964,769 A | 10/1999 | Wagner et al. |
| 5,964,783 A | 10/1999 | Grafton et al. |
| 5,968,045 A | 10/1999 | Frazier |
| 5,968,047 A | 10/1999 | Reed |
| 5,968,077 A | 10/1999 | Wojciechowicz et al. |
| 5,972,006 A | 10/1999 | Sciaino, Jr. |
| 5,976,125 A | 11/1999 | Graham |
| 5,976,127 A | 11/1999 | Lax |
| 5,980,524 A | 11/1999 | Justin et al. |
| 5,980,539 A | 11/1999 | Kontos |
| 5,980,558 A | 11/1999 | Wiley |
| 5,980,559 A | 11/1999 | Bonutti |
| 5,989,252 A | 11/1999 | Fumex |
| 5,989,256 A | 11/1999 | Kuslich et al. |
| 5,989,282 A | 11/1999 | Bonutti |
| 5,993,452 A | 11/1999 | Vandewalle |
| 5,993,476 A | 11/1999 | Groiso |
| 5,997,542 A | 12/1999 | Burke |
| 5,997,552 A | 12/1999 | Person et al. |
| 5,997,575 A | 12/1999 | Whitson et al. |
| 6,001,100 A | 12/1999 | Sherman et al. |
| 6,007,538 A | 12/1999 | Levin |
| 6,007,567 A | 12/1999 | Bonutti |
| 6,010,525 A | 1/2000 | Bonutti et al. |
| 6,016,727 A | 1/2000 | Morgan |
| 6,022,352 A | 2/2000 | Vandewalle |
| 6,022,373 A | 2/2000 | Li |
| 6,024,758 A | 2/2000 | Thal |
| 6,027,523 A | 2/2000 | Schmieding |
| 6,030,410 A | 2/2000 | Zurbrugg |
| 6,033,429 A | 3/2000 | Magovern |
| 6,033,430 A | 3/2000 | Bonutti |
| 6,039,753 A | 3/2000 | Meislin |
| 6,041,485 A | 3/2000 | Pedlick et al. |
| 6,042,601 A | 3/2000 | Smith |
| 6,045,551 A | 4/2000 | Bonutti |
| 6,045,571 A | 4/2000 | Hill et al. |
| 6,045,572 A | 4/2000 | Johnson et al. |
| 6,045,573 A | 4/2000 | Wenstrom, Jr. et al. |
| 6,045,574 A | 4/2000 | Thal |
| 6,047,826 A | 4/2000 | Kalinski et al. |
| 6,048,343 A | 4/2000 | Mathis et al. |
| 6,051,006 A | 4/2000 | Shluzas et al. |
| 6,051,007 A | 4/2000 | Hogendijk et al. |
| 6,053,916 A | 4/2000 | Moore |
| 6,053,921 A | 4/2000 | Wagner et al. |
| 6,056,752 A | 5/2000 | Roger |
| 6,056,772 A | 5/2000 | Bonutti |
| 6,056,773 A | 5/2000 | Bonutti |
| 6,059,817 A | 5/2000 | Bonutti et al. |
| 6,059,818 A | 5/2000 | Johnson et al. |
| 6,062,344 A | 5/2000 | Okabe et al. |
| 6,068,648 A | 5/2000 | Cole et al. |
| 6,071,305 A | 6/2000 | Brown et al. |
| 6,074,403 A | 6/2000 | Nord |
| 6,077,277 A | 6/2000 | Mollenauer et al. |
| 6,077,292 A | 6/2000 | Bonutti |
| 6,080,185 A | 6/2000 | Johnson et al. |
| 6,086,591 A | 7/2000 | Bojarski |
| 6,086,592 A | 7/2000 | Rosenberg et al. |
| 6,086,608 A | 7/2000 | Ek et al. |
| 6,093,200 A | 7/2000 | Liu et al. |
| 6,096,060 A | 8/2000 | Fitts et al. |
| 6,099,527 A | 8/2000 | Hochschuler et al. |
| 6,099,530 A | 8/2000 | Simonian et al. |
| 6,099,568 A | 8/2000 | Simonian et al. |
| 6,106,545 A | 8/2000 | Egan |
| 6,110,128 A | 8/2000 | Andelin et al. |
| 6,117,160 A | 9/2000 | Bonutti |
| 6,117,162 A | 9/2000 | Schmieding et al. |
| 6,123,710 A | 9/2000 | Pinczewski et al. |
| 6,132,433 A | 10/2000 | Whelan |
| 6,132,437 A | 10/2000 | Omurtag et al. |
| 6,139,565 A | 10/2000 | Stone et al. |
| RE36,974 E | 11/2000 | Bonutti |
| 6,143,017 A | 11/2000 | Thal |
| 6,146,406 A | 11/2000 | Shluzas et al. |
| 6,146,408 A | 11/2000 | Bartlett |
| 6,149,653 A | 11/2000 | Deslauriers |
| 6,149,669 A * | 11/2000 | Li .................. 606/232 |
| 6,152,928 A | 11/2000 | Wenstrom, Jr. |
| 6,152,934 A | 11/2000 | Harper et al. |
| 6,152,936 A | 11/2000 | Christy et al. |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,165,203 A | 12/2000 | Krebs |
| 6,168,598 B1 | 1/2001 | Martello |
| 6,168,628 B1 | 1/2001 | Huebner |
| 6,171,310 B1 | 1/2001 | Giordano et al. |
| 6,179,840 B1 | 1/2001 | Bowman |
| 6,183,461 B1 | 2/2001 | Matsuura et al. |
| 6,187,025 B1 | 2/2001 | Machek |
| 6,190,401 B1 | 2/2001 | Green et al. |
| 6,190,411 B1 | 2/2001 | Lo et al. |
| 6,193,754 B1 | 2/2001 | Seedhom |
| 6,200,318 B1 | 3/2001 | Har-Shai et al. |
| 6,200,329 B1 | 3/2001 | Fung et al. |
| 6,200,330 B1 | 3/2001 | Benderev et al. |
| 6,203,556 B1 | 3/2001 | Evans et al. |
| 6,203,565 B1 | 3/2001 | Bonutti et al. |
| 6,203,572 B1 | 3/2001 | Johnson et al. |
| 6,206,883 B1 | 3/2001 | Tunc |
| 6,210,376 B1 | 4/2001 | Grayson |
| 6,214,012 B1 | 4/2001 | Karpman et al. |
| 6,217,580 B1 | 4/2001 | Levin |
| 6,221,107 B1 | 4/2001 | Steiner et al. |
| 6,228,096 B1 | 5/2001 | Marchand |
| 6,231,592 B1 | 5/2001 | Bonutti et al. |

(56) References Cited

U.S. PATENT DOCUMENTS

| | | |
|---|---|---|
| 6,235,057 B1 | 5/2001 | Roger et al. |
| 6,238,395 B1 | 5/2001 | Bonutti |
| 6,241,734 B1 | 6/2001 | Scribner et al. |
| 6,241,747 B1 | 6/2001 | Ruff |
| 6,241,771 B1 | 6/2001 | Gresser et al. |
| 6,245,081 B1 | 6/2001 | Bowman et al. |
| 6,258,091 B1 | 7/2001 | Sevrain et al. |
| 6,267,766 B1 | 7/2001 | Burkhart |
| 6,269,716 B1 | 8/2001 | Amis |
| 6,270,518 B1 | 8/2001 | Pedlick et al. |
| 6,273,890 B1 | 8/2001 | Frazier |
| 6,280,474 B1 | 8/2001 | Cassidy et al. |
| 6,283,973 B1 | 9/2001 | Hubbard et al. |
| 6,283,996 B1 | 9/2001 | Chervitz et al. |
| 6,287,307 B1 | 9/2001 | Abboudi |
| 6,287,325 B1 | 9/2001 | Bonutti |
| 6,293,961 B2 | 9/2001 | Schwartz et al. |
| 6,296,659 B1 | 10/2001 | Foerster |
| 6,299,615 B1 | 10/2001 | Huebner |
| 6,302,888 B1 | 10/2001 | Mellinger et al. |
| 6,302,899 B1 | 10/2001 | Johnson et al. |
| 6,303,158 B1 | 10/2001 | Odgaard et al. |
| 6,306,156 B1 | 10/2001 | Clark |
| 6,306,158 B1 | 10/2001 | Bartlett |
| 6,306,159 B1 | 10/2001 | Schwartz et al. |
| 6,309,405 B1 | 10/2001 | Bonutti |
| 6,312,448 B1 | 11/2001 | Bonutti |
| 6,315,788 B1 | 11/2001 | Roby |
| 6,319,271 B1 | 11/2001 | Schwartz et al. |
| 6,328,758 B1 | 12/2001 | Tornier et al. |
| 6,342,060 B1 | 1/2002 | Adams |
| 6,343,531 B2 | 2/2002 | Amis |
| 6,358,270 B1 | 3/2002 | Lemer |
| 6,364,897 B1 | 4/2002 | Bonutti |
| 6,368,322 B1 | 4/2002 | Luks et al. |
| 6,368,326 B1 | 4/2002 | Dakin et al. |
| 6,368,343 B1 | 4/2002 | Bonutti et al. |
| 6,371,124 B1 | 4/2002 | Whelan |
| 6,379,361 B1 | 4/2002 | Beck, Jr. et al. |
| 6,383,190 B1 | 5/2002 | Preissman |
| 6,383,199 B2 | 5/2002 | Carter et al. |
| 6,387,113 B1 | 5/2002 | Hawkins et al. |
| 6,387,129 B2 | 5/2002 | Rieser et al. |
| 6,391,030 B1 | 5/2002 | Wagner et al. |
| 6,398,785 B2 | 6/2002 | Carchidi et al. |
| 6,406,479 B1 | 6/2002 | Justin et al. |
| 6,409,743 B1 | 6/2002 | Fenton, Jr. |
| 6,413,260 B1 | 7/2002 | Berrevoets et al. |
| 6,423,088 B1 | 7/2002 | Fenton, Jr. |
| 6,428,562 B2 | 8/2002 | Bonutti |
| 6,432,123 B2 | 8/2002 | Schwartz et al. |
| 6,436,123 B1 | 8/2002 | Magovern |
| 6,436,124 B1 | 8/2002 | Anderson et al. |
| 6,440,134 B1 | 8/2002 | Zaccherotti et al. |
| 6,440,136 B1 | 8/2002 | Gambale et al. |
| 6,447,516 B1 | 9/2002 | Bonutti |
| 6,451,030 B2 | 9/2002 | Li et al. |
| 6,454,768 B1 | 9/2002 | Jackson |
| 6,458,134 B1 | 10/2002 | Songer et al. |
| 6,461,373 B2 | 10/2002 | Wyman et al. |
| 6,464,690 B1 | 10/2002 | Castaneda et al. |
| 6,464,713 B2 | 10/2002 | Bonutti |
| 6,468,293 B2 | 10/2002 | Bonutti et al. |
| 6,471,707 B1 | 10/2002 | Miller et al. |
| 6,475,230 B1 | 11/2002 | Bonutti et al. |
| 6,482,210 B1 | 11/2002 | Skiba et al. |
| 6,485,504 B1 | 11/2002 | Johnson et al. |
| 6,491,714 B1 | 12/2002 | Bennett |
| 6,497,901 B1 | 12/2002 | Royer |
| 6,500,184 B1 | 12/2002 | Chan et al. |
| 6,500,195 B2 | 12/2002 | Bonutti |
| RE37,963 E | 1/2003 | Thal |
| 6,503,267 B2 | 1/2003 | Bonutti et al. |
| 6,506,190 B1 | 1/2003 | Walshe |
| 6,508,820 B2 | 1/2003 | Bales |
| 6,508,821 B1 | 1/2003 | Schwartz et al. |
| 6,508,830 B2 | 1/2003 | Steiner |
| 6,511,498 B1 | 1/2003 | Fumex |
| 6,511,499 B2 | 1/2003 | Schmieding et al. |
| 6,517,542 B1 | 2/2003 | Papay et al. |
| 6,517,552 B1 | 2/2003 | Nord et al. |
| 6,517,578 B2 | 2/2003 | Hein |
| 6,517,579 B1 | 2/2003 | Paulos et al. |
| 6,520,964 B2 | 2/2003 | Tallarida et al. |
| 6,520,980 B1 | 2/2003 | Foerster |
| 6,524,317 B1 | 2/2003 | Ritchart et al. |
| 6,527,777 B2 | 3/2003 | Justin |
| 6,527,794 B1 | 3/2003 | McDevitt et al. |
| 6,527,795 B1 | 3/2003 | Lizardi |
| 6,533,795 B1 | 3/2003 | Tran et al. |
| 6,533,802 B2 | 3/2003 | Bojarski et al. |
| 6,537,319 B2 | 3/2003 | Whelan |
| 6,540,750 B2 | 4/2003 | Burkhart |
| 6,540,769 B1 | 4/2003 | Miller, III |
| 6,540,770 B1 | 4/2003 | Tornier et al. |
| 6,543,094 B2 | 4/2003 | D'Addario |
| 6,544,281 B2 | 4/2003 | ElAttrache et al. |
| 6,547,564 B1 | 4/2003 | Hansson et al. |
| 6,547,778 B1 | 4/2003 | Sklar et al. |
| 6,547,800 B2 | 4/2003 | Foerster et al. |
| 6,551,330 B1 | 4/2003 | Bain et al. |
| 6,551,343 B1 | 4/2003 | Tormala et al. |
| 6,553,802 B1 | 4/2003 | Jacob et al. |
| 6,554,830 B1 | 4/2003 | Chappius |
| 6,554,852 B1 | 4/2003 | Oberlander |
| 6,554,862 B2 | 4/2003 | Hays et al. |
| 6,562,071 B2 | 5/2003 | Jarvinen et al. |
| 6,565,572 B2 | 5/2003 | Chappius |
| 6,565,573 B1 | 5/2003 | Ferrante et al. |
| 6,569,186 B1 | 5/2003 | Winters et al. |
| 6,569,187 B1 | 5/2003 | Bonutti et al. |
| 6,572,635 B1 | 6/2003 | Bonutti |
| 6,575,925 B1 | 6/2003 | Noble |
| 6,579,295 B1 | 6/2003 | Supinski |
| 6,582,453 B1 | 6/2003 | Tran et al. |
| 6,585,730 B1 | 7/2003 | Foerster |
| 6,585,740 B2 | 7/2003 | Schlapfer et al. |
| 6,585,750 B2 | 7/2003 | Bonutti et al. |
| 6,589,245 B1 | 7/2003 | Weiler et al. |
| 6,589,246 B1 | 7/2003 | Hack et al. |
| 6,592,609 B1 | 7/2003 | Bonutti |
| 6,595,911 B2 | 7/2003 | LoVuolo |
| 6,599,289 B1 | 7/2003 | Bojarski et al. |
| 6,605,096 B1 | 8/2003 | Ritchart |
| 6,607,548 B2 | 8/2003 | Pohjonen et al. |
| 6,610,079 B1 | 8/2003 | Li et al. |
| 6,613,018 B2 | 9/2003 | Bagga et al. |
| 6,616,694 B1 | 9/2003 | Hart |
| 6,620,166 B1 | 9/2003 | Wenstrom, Jr. et al. |
| 6,620,185 B1 | 9/2003 | Harvie et al. |
| 6,620,195 B2 | 9/2003 | Goble et al. |
| 6,620,329 B2 | 9/2003 | Rosen et al. |
| 6,620,349 B1 | 9/2003 | Lopez |
| 6,623,492 B1 | 9/2003 | Berube et al. |
| 6,623,524 B2 | 9/2003 | Schmieding |
| 6,626,910 B1 | 9/2003 | Hugues et al. |
| 6,626,919 B1 | 9/2003 | Swanstrom |
| 6,629,977 B1 | 10/2003 | Wolf |
| 6,635,073 B2 | 10/2003 | Bonutti |
| 6,638,279 B2 | 10/2003 | Bonutti |
| 6,638,312 B2 | 10/2003 | Plouhar et al. |
| 6,641,596 B1 | 11/2003 | Lizardi |
| 6,641,597 B2 | 11/2003 | Burkhart et al. |
| 6,645,211 B2 | 11/2003 | Magana |
| 6,645,227 B2 | 11/2003 | Fallin et al. |
| 6,652,450 B2 | 11/2003 | Neisz et al. |
| 6,652,562 B2 | 11/2003 | Collier et al. |
| 6,652,563 B2 | 11/2003 | Dreyfuss |
| 6,656,182 B1 | 12/2003 | Hayhurst |
| 6,656,183 B2 | 12/2003 | Colleran et al. |
| 6,658,182 B1 | 12/2003 | Gonthier et al. |
| 6,660,008 B1 | 12/2003 | Foerster et al. |
| 6,660,022 B1 | 12/2003 | Li et al. |
| 6,663,634 B2 | 12/2003 | Ahrens et al. |

(56) References Cited

U.S. PATENT DOCUMENTS

| | | |
|---|---|---|
| 6,663,656 B2 | 12/2003 | Schmieding et al. |
| 6,666,868 B2 | 12/2003 | Fallin |
| 6,682,533 B1 | 1/2004 | Dinsdale et al. |
| 6,682,549 B2 | 1/2004 | Bartlett |
| 6,685,728 B2 | 2/2004 | Sinnott et al. |
| 6,689,137 B2 | 2/2004 | Reed |
| 6,689,153 B1 | 2/2004 | Skiba |
| 6,689,154 B2 | 2/2004 | Bartlett |
| 6,692,499 B2 | 2/2004 | Tormala et al. |
| 6,692,516 B2 | 2/2004 | West, Jr. et al. |
| 6,695,852 B2 | 2/2004 | Gleason |
| 6,712,849 B2 | 3/2004 | Re et al. |
| 6,716,224 B2 | 4/2004 | Singhatat |
| 6,716,957 B2 | 4/2004 | Tunc |
| 6,730,092 B2 | 5/2004 | Songer |
| 6,730,124 B2 | 5/2004 | Steiner |
| 6,736,799 B1 | 5/2004 | Erbe et al. |
| 6,737,053 B1 | 5/2004 | Goh et al. |
| 6,746,483 B1 | 6/2004 | Bojarski et al. |
| 6,752,810 B1 | 6/2004 | Gao et al. |
| 6,752,831 B2 | 6/2004 | Sybert et al. |
| 6,755,836 B1 | 6/2004 | Lewis |
| 6,761,739 B2 | 7/2004 | Shepard |
| 6,767,037 B2 | 7/2004 | Wenstrom, Jr. |
| 6,770,076 B2 | 8/2004 | Foerster |
| 6,770,084 B1 | 8/2004 | Bain et al. |
| 6,773,450 B2 | 8/2004 | Leung et al. |
| 6,779,701 B2 | 8/2004 | Bailly et al. |
| 6,780,190 B2 | 8/2004 | Maroney |
| 6,780,198 B1 | 8/2004 | Gregoire et al. |
| 6,793,595 B1 | 9/2004 | Monnet |
| 6,802,862 B1 | 10/2004 | Roger et al. |
| 6,808,502 B2 | 10/2004 | Nguyen et al. |
| 6,808,526 B1 | 10/2004 | Magerl et al. |
| 6,814,741 B2 | 11/2004 | Bowman et al. |
| 6,830,572 B2 | 12/2004 | McDevitt et al. |
| 6,833,005 B1 | 12/2004 | Mantas et al. |
| 6,840,953 B2 | 1/2005 | Martinek |
| 6,860,885 B2 | 3/2005 | Bonutti |
| 6,863,671 B1 | 3/2005 | Strobel et al. |
| 6,872,040 B2 | 3/2005 | Deeg et al. |
| 6,872,210 B2 | 3/2005 | Hearn |
| 6,875,216 B2 | 4/2005 | Wolf |
| 6,884,249 B2 | 4/2005 | May et al. |
| 6,887,259 B2 | 5/2005 | Lizardi |
| 6,890,354 B2 | 5/2005 | Steiner et al. |
| 6,893,448 B2 | 5/2005 | O'Quinn et al. |
| 6,896,686 B2 | 5/2005 | Weber |
| 6,899,722 B2 | 5/2005 | Bonutti |
| 6,902,573 B2 | 6/2005 | Strobel et al. |
| 6,905,513 B1 | 6/2005 | Metzger |
| 6,908,466 B1 | 6/2005 | Bonutti et al. |
| 6,916,292 B2 | 7/2005 | Morawski et al. |
| 6,916,321 B2 | 7/2005 | TenHuisen et al. |
| 6,921,402 B2 | 7/2005 | Contiliano et al. |
| 6,923,823 B1 | 8/2005 | Bartlett et al. |
| 6,923,824 B2 | 8/2005 | Morgan et al. |
| 6,951,565 B2 | 10/2005 | Keane et al. |
| 6,966,887 B1 | 11/2005 | Chin |
| 6,966,916 B2 | 11/2005 | Kumar |
| 6,969,391 B1 | 11/2005 | Gazzani |
| 6,969,398 B2 | 11/2005 | Stevens et al. |
| 6,972,027 B2 | 12/2005 | Fallin et al. |
| 6,980,903 B2 | 12/2005 | Daniels et al. |
| 6,984,237 B2 | 1/2006 | Hatch et al. |
| 6,986,781 B2 | 1/2006 | Smith |
| 6,989,034 B2 | 1/2006 | Hammer et al. |
| 6,994,719 B2 | 2/2006 | Grafton |
| 7,001,429 B2 | 2/2006 | Ferguson |
| 7,004,959 B2 | 2/2006 | Bonutti |
| 7,048,754 B2 | 5/2006 | Martin et al. |
| 7,052,499 B2 | 5/2006 | Steger et al. |
| 7,066,942 B2 | 6/2006 | Treace |
| 7,066,944 B2 | 6/2006 | Laufer et al. |
| 7,081,126 B2 | 7/2006 | McDevitt et al. |
| 7,087,064 B1 | 8/2006 | Hyde |
| 7,105,010 B2 | 9/2006 | Hart et al. |
| 7,112,221 B2 | 9/2006 | Harris et al. |
| 7,118,583 B2 | 10/2006 | O'Quinn et al. |
| 7,131,467 B2 | 11/2006 | Gao et al. |
| 7,137,996 B2 | 11/2006 | Steiner et al. |
| 7,141,066 B2 | 11/2006 | Steiner et al. |
| 7,144,414 B2 | 12/2006 | Harvie et al. |
| 7,153,127 B2 | 12/2006 | Struble et al. |
| 7,153,307 B2 | 12/2006 | Scribner et al. |
| 7,153,312 B1 | 12/2006 | Torrie et al. |
| 7,153,327 B1 | 12/2006 | Metzger |
| 7,160,333 B2 | 1/2007 | Plouhar et al. |
| 7,201,722 B2 | 4/2007 | Krueger |
| 7,207,993 B1 | 4/2007 | Baldwin et al. |
| 7,255,675 B2 | 8/2007 | Gertner et al. |
| 7,255,715 B2 | 8/2007 | Metzger |
| 7,261,716 B2 | 8/2007 | Strobel et al. |
| 7,264,634 B2 | 9/2007 | Schmieding |
| 7,279,008 B2 | 10/2007 | Brown et al. |
| 7,285,124 B2 | 10/2007 | Foerster |
| 7,303,577 B1 | 12/2007 | Dean |
| 7,306,417 B2 | 12/2007 | Dorstewitz |
| 7,326,222 B2 | 2/2008 | Dreyfuss et al. |
| 7,329,272 B2 | 2/2008 | Burkhart et al. |
| 7,361,179 B2 | 4/2008 | Rousseau et al. |
| 7,377,845 B2 | 5/2008 | Stewart et al. |
| 7,390,329 B2 | 6/2008 | Westra et al. |
| 7,390,332 B2 | 6/2008 | Selvitelli et al. |
| 7,399,018 B1 | 7/2008 | Khachaturian |
| 7,442,210 B2 | 10/2008 | Segal et al. |
| 7,465,308 B2 | 12/2008 | Sikora et al. |
| 7,494,506 B2 | 2/2009 | Brulez et al. |
| 7,500,983 B1 | 3/2009 | Kaiser et al. |
| 7,513,910 B2 | 4/2009 | Buskirk et al. |
| 7,578,825 B2 | 8/2009 | Huebner |
| 7,585,311 B2 | 9/2009 | Green et al. |
| 7,591,823 B2 | 9/2009 | Tipirneni |
| 7,601,165 B2 | 10/2009 | Stone |
| 7,608,092 B1 | 10/2009 | Schaffhausen |
| 7,608,098 B1 | 10/2009 | Stone et al. |
| 7,615,076 B2 | 11/2009 | Cauthen, III et al. |
| 7,632,287 B2 | 12/2009 | Baker et al. |
| 7,651,509 B2 | 1/2010 | Bojarski et al. |
| 7,658,750 B2 | 2/2010 | Li |
| 7,658,751 B2 | 2/2010 | Stone et al. |
| 7,670,279 B2 | 3/2010 | Gertner |
| 7,678,123 B2 | 3/2010 | Chanduszko |
| 7,695,493 B2 | 4/2010 | Saadat et al. |
| 7,695,503 B1 | 4/2010 | Kaiser et al. |
| 7,717,929 B2 | 5/2010 | Fallman |
| 7,736,364 B2 | 6/2010 | Stone |
| 7,736,379 B2 | 6/2010 | Ewers et al. |
| 7,749,250 B2 | 7/2010 | Stone et al. |
| 7,758,594 B2 | 7/2010 | Lamson et al. |
| 7,776,041 B1 | 8/2010 | Walters |
| 7,819,895 B2 | 10/2010 | Ginn et al. |
| 7,828,820 B2 | 11/2010 | Stone et al. |
| 7,856,698 B2 | 12/2010 | Hays |
| 7,857,830 B2 | 12/2010 | Stone et al. |
| 7,867,264 B2 | 1/2011 | McDevitt et al. |
| 7,875,058 B2 | 1/2011 | Holmes, Jr. |
| 7,878,058 B2 | 2/2011 | Blendinger et al. |
| 7,905,903 B2 | 3/2011 | Stone et al. |
| 7,905,904 B2 | 3/2011 | Stone et al. |
| 7,909,851 B2 | 3/2011 | Stone et al. |
| 7,938,847 B2 | 5/2011 | Fanton et al. |
| 7,959,650 B2 | 6/2011 | Kaiser et al. |
| 7,981,140 B2 | 7/2011 | Burkhart |
| 7,998,203 B2 | 8/2011 | Blum |
| 8,062,334 B2 | 11/2011 | Green et al. |
| 8,075,574 B2 | 12/2011 | May et al. |
| 8,088,130 B2 | 1/2012 | Kaiser et al. |
| 8,114,127 B2 | 2/2012 | West, Jr. |
| 8,114,128 B2 | 2/2012 | Cauldwell et al. |
| 8,118,836 B2 | 2/2012 | Denham et al. |
| 8,128,658 B2 | 3/2012 | Kaiser et al. |
| 8,137,354 B2 | 3/2012 | Stone |
| 8,137,382 B2 | 3/2012 | Denham et al. |

(56) References Cited

U.S. PATENT DOCUMENTS

| | | | |
|---|---|---|---|
| 8,167,906 B2 | 5/2012 | Cauldwell et al. |
| 8,202,318 B2 | 6/2012 | Willobee |
| 8,221,454 B2 | 7/2012 | Schaffhausen |
| 8,231,654 B2 | 7/2012 | Kaiser et al. |
| 8,251,998 B2 | 8/2012 | Hoeppner et al. |
| 8,273,106 B2 | 9/2012 | Stone et al. |
| 8,292,921 B2 | 10/2012 | Stone et al. |
| 8,298,284 B2 | 10/2012 | Cassani |
| 8,337,525 B2 | 12/2012 | Stone et al. |
| 8,343,155 B2 | 1/2013 | Fisher et al. |
| 8,343,227 B2 | 1/2013 | Metzger et al. |
| 8,361,113 B2 | 1/2013 | Stone et al. |
| 8,409,253 B2 | 4/2013 | Stone et al. |
| 8,486,114 B2 | 7/2013 | Gillard et al. |
| 8,500,818 B2 | 8/2013 | Metzger et al. |
| 8,506,597 B2 | 8/2013 | Kaiser et al. |
| 8,551,140 B2 | 10/2013 | Denham et al. |
| 8,562,645 B2 | 10/2013 | Stone et al. |
| 8,562,647 B2 | 10/2013 | Kaiser et al. |
| 8,597,327 B2 | 12/2013 | Stone et al. |
| 8,608,777 B2 | 12/2013 | Kaiser et al. |
| 8,632,566 B2 | 1/2014 | Olson |
| 8,632,569 B2 | 1/2014 | Stone et al. |
| 8,652,171 B2 | 2/2014 | Stone et al. |
| 8,652,172 B2 | 2/2014 | Denham et al. |
| 8,672,968 B2 | 3/2014 | Stone et al. |
| 8,672,969 B2 | 3/2014 | Stone et al. |
| 8,721,650 B2 | 5/2014 | Fanton et al. |
| 8,721,684 B2 | 5/2014 | Denham et al. |
| 8,771,316 B2 | 7/2014 | Denham et al. |
| 8,771,352 B2 | 7/2014 | Conner et al. |
| 8,777,956 B2 | 7/2014 | Hoeppner et al. |
| 8,801,783 B2 | 8/2014 | Stone et al. |
| 8,840,645 B2 | 9/2014 | Denham et al. |
| 8,900,314 B2 | 12/2014 | Metzger et al. |
| 8,932,331 B2 | 1/2015 | Kaiser et al. |
| 8,936,621 B2 | 1/2015 | Denham et al. |
| 8,968,364 B2 | 3/2015 | Berelsman et al. |
| 8,998,949 B2 | 4/2015 | Stone et al. |
| 9,005,287 B2 | 4/2015 | Stone |
| 9,017,381 B2 | 4/2015 | Kaiser et al. |
| 9,023,058 B2 * | 5/2015 | Jaramillo et al. ............. 606/103 |
| 2001/0010005 A1 | 7/2001 | Kammerer et al. |
| 2001/0014825 A1 | 8/2001 | Burke et al. |
| 2001/0019649 A1 | 9/2001 | Field et al. |
| 2001/0029387 A1 | 10/2001 | Wolf et al. |
| 2001/0037131 A1 | 11/2001 | Schmieding et al. |
| 2001/0037153 A1 | 11/2001 | Rockwood et al. |
| 2001/0041916 A1 | 11/2001 | Bonutti |
| 2001/0041937 A1 | 11/2001 | Rieser et al. |
| 2001/0041938 A1 | 11/2001 | Hein |
| 2001/0044639 A1 | 11/2001 | Levinson |
| 2001/0047206 A1 | 11/2001 | Sklar et al. |
| 2001/0051816 A1 | 12/2001 | Enzerink et al. |
| 2001/0053934 A1 | 12/2001 | Schmieding |
| 2002/0001964 A1 | 1/2002 | Choi |
| 2002/0004669 A1 | 1/2002 | Bartlett |
| 2002/0007182 A1 | 1/2002 | Kim |
| 2002/0010513 A1 | 1/2002 | Schmieding |
| 2002/0013607 A1 | 1/2002 | Lemer |
| 2002/0013608 A1 | 1/2002 | ElAttrache et al. |
| 2002/0019649 A1 | 2/2002 | Sikora et al. |
| 2002/0029066 A1 | 3/2002 | Foerster |
| 2002/0032465 A1 | 3/2002 | Lemer |
| 2002/0055780 A1 | 5/2002 | Sklar |
| 2002/0058966 A1 | 5/2002 | Tormala et al. |
| 2002/0068254 A1 | 6/2002 | Campbell |
| 2002/0077659 A1 | 6/2002 | Johnson et al. |
| 2002/0099411 A1 | 7/2002 | Bartlett |
| 2002/0111653 A1 | 8/2002 | Foerster |
| 2002/0120270 A1 | 8/2002 | Trieu et al. |
| 2002/0120292 A1 | 8/2002 | Morgan |
| 2002/0123752 A1 | 9/2002 | Schultheiss et al. |
| 2002/0128654 A1 | 9/2002 | Steger et al. |
| 2002/0128684 A1 | 9/2002 | Foerster |
| 2002/0129820 A1 | 9/2002 | Ryan et al. |
| 2002/0143336 A1 | 10/2002 | Hearn |
| 2002/0147463 A1 | 10/2002 | Martinek |
| 2002/0156475 A1 | 10/2002 | Lerch et al. |
| 2002/0161401 A1 | 10/2002 | Steiner |
| 2002/0161439 A1 | 10/2002 | Strobel et al. |
| 2002/0165548 A1 | 11/2002 | Jutley |
| 2002/0165611 A1 | 11/2002 | Enzerink et al. |
| 2002/0169452 A1 | 11/2002 | Tormala et al. |
| 2002/0169477 A1 | 11/2002 | Demopulos et al. |
| 2002/0169478 A1 | 11/2002 | Schwartz et al. |
| 2002/0173788 A1 | 11/2002 | Bojarski et al. |
| 2002/0177853 A1 | 11/2002 | Chervitz et al. |
| 2002/0188298 A1 | 12/2002 | Chan |
| 2002/0193830 A1 | 12/2002 | Bonutti |
| 2003/0009235 A1 | 1/2003 | Manrique et al. |
| 2003/0023268 A1 | 1/2003 | Lizardi |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0065391 A1 | 4/2003 | Re et al. |
| 2003/0065402 A1 | 4/2003 | Anderson et al. |
| 2003/0078585 A1 | 4/2003 | Johnson et al. |
| 2003/0078603 A1 | 4/2003 | Schaller et al. |
| 2003/0078617 A1 | 4/2003 | Schwartz et al. |
| 2003/0083662 A1 | 5/2003 | Middleton |
| 2003/0083694 A1 | 5/2003 | Miller |
| 2003/0088251 A1 | 5/2003 | Braun et al. |
| 2003/0088272 A1 | 5/2003 | Smith |
| 2003/0105477 A1 | 6/2003 | Schwartz et al. |
| 2003/0105489 A1 | 6/2003 | Eichhorn et al. |
| 2003/0120309 A1 | 6/2003 | Colleran et al. |
| 2003/0130670 A1 | 7/2003 | Anderson et al. |
| 2003/0130694 A1 | 7/2003 | Bojarski et al. |
| 2003/0130695 A1 | 7/2003 | McDevitt et al. |
| 2003/0135214 A1 | 7/2003 | Fetto et al. |
| 2003/0135239 A1 | 7/2003 | Gabriel et al. |
| 2003/0135963 A1 | 7/2003 | Holbrook et al. |
| 2003/0139775 A1 | 7/2003 | Grafton |
| 2003/0149448 A1 | 8/2003 | Foerster et al. |
| 2003/0152522 A1 | 8/2003 | Miller et al. |
| 2003/0153947 A1 | 8/2003 | Koseki |
| 2003/0167072 A1 | 9/2003 | Oberlander |
| 2003/0167090 A1 | 9/2003 | Chervitz et al. |
| 2003/0171811 A1 | 9/2003 | Steiner et al. |
| 2003/0176865 A1 | 9/2003 | Supinski |
| 2003/0176919 A1 | 9/2003 | Schmieding |
| 2003/0181925 A1 | 9/2003 | Bain et al. |
| 2003/0195528 A1 | 10/2003 | Ritchart |
| 2003/0195564 A1 | 10/2003 | Tran et al. |
| 2003/0208210 A1 * | 11/2003 | Dreyfuss et al. ............. 606/144 |
| 2003/0212456 A1 | 11/2003 | Lipchitz et al. |
| 2003/0216809 A1 | 11/2003 | Ferguson |
| 2003/0220660 A1 | 11/2003 | Kortenbach et al. |
| 2003/0225459 A1 | 12/2003 | Hammer et al. |
| 2003/0229361 A1 * | 12/2003 | Jackson ....................... 606/144 |
| 2004/0002734 A1 | 1/2004 | Fallin et al. |
| 2004/0006345 A1 | 1/2004 | Vlahos et al. |
| 2004/0006346 A1 | 1/2004 | Holmen et al. |
| 2004/0015171 A1 | 1/2004 | Bojarski et al. |
| 2004/0015172 A1 | 1/2004 | Biedermann et al. |
| 2004/0024456 A1 | 2/2004 | Brown et al. |
| 2004/0024457 A1 | 2/2004 | Boyce et al. |
| 2004/0044391 A1 | 3/2004 | Porter |
| 2004/0059357 A1 | 3/2004 | Koseki |
| 2004/0087981 A1 | 5/2004 | Berube et al. |
| 2004/0092936 A1 | 5/2004 | Miller et al. |
| 2004/0093032 A1 | 5/2004 | Sinnott et al. |
| 2004/0098051 A1 | 5/2004 | Fallin et al. |
| 2004/0098053 A1 | 5/2004 | Tran |
| 2004/0111117 A1 | 6/2004 | Colleran et al. |
| 2004/0122431 A1 | 6/2004 | Biedermann et al. |
| 2004/0127907 A1 * | 7/2004 | Dakin et al. ................... 606/72 |
| 2004/0133206 A1 | 7/2004 | Stevens et al. |
| 2004/0133211 A1 | 7/2004 | Raskin et al. |
| 2004/0138664 A1 | 7/2004 | Bowman |
| 2004/0138683 A1 | 7/2004 | Shelton et al. |

(56) References Cited

U.S. PATENT DOCUMENTS

| | | |
|---|---|---|
| 2004/0138704 A1 | 7/2004 | Gambale et al. |
| 2004/0138706 A1 | 7/2004 | Abrams et al. |
| 2004/0138747 A1 | 7/2004 | Kaladelfos |
| 2004/0143344 A1 | 7/2004 | Malaviya et al. |
| 2004/0147932 A1 | 7/2004 | Burkinshaw et al. |
| 2004/0147958 A1 | 7/2004 | Lam et al. |
| 2004/0153103 A1 | 8/2004 | Schwartz et al. |
| 2004/0153153 A1 | 8/2004 | Elson et al. |
| 2004/0162579 A1 | 8/2004 | Foerster |
| 2004/0166169 A1 | 8/2004 | Malaviya et al. |
| 2004/0181234 A1 | 9/2004 | McDevitt et al. |
| 2004/0182968 A1 | 9/2004 | Gentry |
| 2004/0187314 A1 | 9/2004 | Johnson |
| 2004/0193185 A1 | 9/2004 | McBrayer |
| 2004/0199169 A1 | 10/2004 | Koons et al. |
| 2004/0204722 A1 | 10/2004 | Sikora et al. |
| 2004/0220574 A1 | 11/2004 | Pelo et al. |
| 2004/0225183 A1 | 11/2004 | Michlitsch et al. |
| 2004/0225292 A1 | 11/2004 | Sasso et al. |
| 2004/0225305 A1 | 11/2004 | Ewers et al. |
| 2004/0236353 A1 | 11/2004 | Bain et al. |
| 2004/0236373 A1 | 11/2004 | Anspach |
| 2004/0243139 A1 | 12/2004 | Lewis et al. |
| 2004/0243178 A1 | 12/2004 | Haut et al. |
| 2004/0243180 A1 | 12/2004 | Donnelly et al. |
| 2004/0243235 A1 | 12/2004 | Goh et al. |
| 2004/0249394 A1 | 12/2004 | Morris et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267286 A1 | 12/2004 | Gao et al. |
| 2004/0267304 A1 | 12/2004 | Zannis et al. |
| 2004/0267309 A1 | 12/2004 | Garvin |
| 2004/0267362 A1 | 12/2004 | Hwang et al. |
| 2005/0021087 A1 | 1/2005 | Koseki |
| 2005/0027307 A1 | 2/2005 | Schwartz et al. |
| 2005/0033363 A1 | 2/2005 | Bojarski et al. |
| 2005/0038426 A1 | 2/2005 | Chan |
| 2005/0049598 A1* | 3/2005 | West et al. ............ 606/72 |
| 2005/0055027 A1 | 3/2005 | Yeung et al. |
| 2005/0055037 A1 | 3/2005 | Fathauer |
| 2005/0064042 A1 | 3/2005 | Vunjak-Novakovic et al. |
| 2005/0065521 A1 | 3/2005 | Steger et al. |
| 2005/0070928 A1 | 3/2005 | Heino et al. |
| 2005/0074495 A1 | 4/2005 | Schwartz et al. |
| 2005/0076478 A1 | 4/2005 | Miyazaki et al. |
| 2005/0085819 A1 | 4/2005 | Ellis et al. |
| 2005/0090827 A1* | 4/2005 | Gedebou ............ 606/72 |
| 2005/0090828 A1 | 4/2005 | Alford |
| 2005/0090862 A1 | 4/2005 | McDevitt et al. |
| 2005/0096696 A1 | 5/2005 | Forsberg |
| 2005/0096697 A1 | 5/2005 | Forsberg et al. |
| 2005/0096743 A1 | 5/2005 | Schmieding et al. |
| 2005/0101957 A1 | 5/2005 | Buskirk et al. |
| 2005/0107795 A1 | 5/2005 | Morris et al. |
| 2005/0107828 A1 | 5/2005 | Reese |
| 2005/0119531 A1 | 6/2005 | Sharratt |
| 2005/0119696 A1 | 6/2005 | Walters et al. |
| 2005/0124996 A1 | 6/2005 | Hearn |
| 2005/0125036 A1 | 6/2005 | Roby |
| 2005/0125073 A1 | 6/2005 | Orban et al. |
| 2005/0131413 A1 | 6/2005 | O'Driscoll et al. |
| 2005/0137600 A1 | 6/2005 | Jacobs et al. |
| 2005/0137624 A1 | 6/2005 | Fallman |
| 2005/0149033 A1 | 7/2005 | McGuire et al. |
| 2005/0149122 A1 | 7/2005 | McDevitt et al. |
| 2005/0149187 A1 | 7/2005 | Clark et al. |
| 2005/0159812 A1 | 7/2005 | Dinger et al. |
| 2005/0165416 A1 | 7/2005 | Bojarski et al. |
| 2005/0165482 A1 | 7/2005 | Goldhahn et al. |
| 2005/0171547 A1 | 8/2005 | Aram |
| 2005/0187565 A1 | 8/2005 | Baker et al. |
| 2005/0187577 A1 | 8/2005 | Selvitelli et al. |
| 2005/0187635 A1 | 8/2005 | Metzger |
| 2005/0203620 A1 | 9/2005 | Steiner et al. |
| 2005/0222618 A1 | 10/2005 | Dreyfuss et al. |
| 2005/0222619 A1 | 10/2005 | Dreyfuss et al. |
| 2005/0228448 A1 | 10/2005 | Li |
| 2005/0240198 A1 | 10/2005 | Albertson et al. |
| 2005/0251177 A1 | 11/2005 | Saadat et al. |
| 2005/0251208 A1 | 11/2005 | Elmer et al. |
| 2005/0251210 A1 | 11/2005 | Westra et al. |
| 2005/0267479 A1 | 12/2005 | Morgan et al. |
| 2005/0267533 A1 | 12/2005 | Gertner |
| 2005/0277939 A1 | 12/2005 | Miller |
| 2005/0277961 A1 | 12/2005 | Stone et al. |
| 2005/0283040 A1 | 12/2005 | Greenhalgh |
| 2005/0283156 A1 | 12/2005 | Schmieding et al. |
| 2005/0283158 A1 | 12/2005 | West |
| 2005/0283192 A1 | 12/2005 | Torrie et al. |
| 2006/0004410 A1 | 1/2006 | Nobis et al. |
| 2006/0015103 A1 | 1/2006 | Burke |
| 2006/0015106 A1 | 1/2006 | Lerch et al. |
| 2006/0030884 A1 | 2/2006 | Yeung et al. |
| 2006/0030948 A1 | 2/2006 | Manrique et al. |
| 2006/0036265 A1 | 2/2006 | Dant |
| 2006/0052818 A1 | 3/2006 | Drake et al. |
| 2006/0064125 A1 | 3/2006 | Henderson et al. |
| 2006/0064126 A1 | 3/2006 | Fallin et al. |
| 2006/0069334 A1 | 3/2006 | Moskowitz |
| 2006/0079904 A1 | 4/2006 | Thal |
| 2006/0084943 A1 | 4/2006 | Rosenman et al. |
| 2006/0085000 A1 | 4/2006 | Mohr et al. |
| 2006/0089672 A1 | 4/2006 | Martinek |
| 2006/0100627 A1 | 5/2006 | Stone et al. |
| 2006/0100637 A1 | 5/2006 | Rathbun et al. |
| 2006/0106423 A1 | 5/2006 | Weisel et al. |
| 2006/0111721 A1 | 5/2006 | Puricelli et al. |
| 2006/0116685 A1 | 6/2006 | Urbanski et al. |
| 2006/0121084 A1 | 6/2006 | Borden et al. |
| 2006/0122608 A1 | 6/2006 | Fallin et al. |
| 2006/0122611 A1 | 6/2006 | Morales et al. |
| 2006/0135958 A1 | 6/2006 | Marissen et al. |
| 2006/0149266 A1 | 7/2006 | Cordasco |
| 2006/0155328 A1 | 7/2006 | Foerster |
| 2006/0161161 A1 | 7/2006 | Shifrin et al. |
| 2006/0167458 A1 | 7/2006 | Gabele |
| 2006/0167481 A1 | 7/2006 | Baker et al. |
| 2006/0167482 A1 | 7/2006 | Swain et al. |
| 2006/0178680 A1 | 8/2006 | Nelson et al. |
| 2006/0189993 A1 | 8/2006 | Stone |
| 2006/0190042 A1 | 8/2006 | Stone et al. |
| 2006/0195101 A1 | 8/2006 | Stevens |
| 2006/0200235 A1 | 9/2006 | Bianchi et al. |
| 2006/0229671 A1 | 10/2006 | Steiner et al. |
| 2006/0229676 A1* | 10/2006 | Doll et al. ............ 606/233 |
| 2006/0235407 A1 | 10/2006 | Wang et al. |
| 2006/0235413 A1 | 10/2006 | Denham et al. |
| 2006/0241624 A1 | 10/2006 | Kizuka et al. |
| 2006/0247642 A1 | 11/2006 | Stone et al. |
| 2006/0253130 A1 | 11/2006 | Wolniewicz |
| 2006/0259048 A1 | 11/2006 | Koseki |
| 2006/0271192 A1 | 11/2006 | Olsen et al. |
| 2006/0276793 A1 | 12/2006 | Berry |
| 2006/0276809 A1 | 12/2006 | Oliveira |
| 2006/0276841 A1 | 12/2006 | Barbieri et al. |
| 2006/0276896 A1 | 12/2006 | Fallin et al. |
| 2006/0280768 A1 | 12/2006 | Hwang et al. |
| 2006/0282082 A1 | 12/2006 | Fanton et al. |
| 2006/0282085 A1 | 12/2006 | Stone et al. |
| 2006/0293709 A1 | 12/2006 | Bojarski et al. |
| 2007/0005068 A1* | 1/2007 | Sklar ............ 606/72 |
| 2007/0005080 A1 | 1/2007 | Wolniewicz et al. |
| 2007/0016305 A1 | 1/2007 | Chudik |
| 2007/0021779 A1 | 1/2007 | Garvin et al. |
| 2007/0027476 A1 | 2/2007 | Harris et al. |
| 2007/0032800 A1 | 2/2007 | Ortiz et al. |
| 2007/0038218 A1 | 2/2007 | Grevious |
| 2007/0043371 A1* | 2/2007 | Teague et al. ............ 606/71 |
| 2007/0055249 A1 | 3/2007 | Jensen et al. |
| 2007/0055251 A1 | 3/2007 | Huebner et al. |
| 2007/0055255 A1 | 3/2007 | Siegel |

(56) References Cited

U.S. PATENT DOCUMENTS

| | | | | |
|---|---|---|---|---|
| 2007/0060922 | A1 | 3/2007 | Dreyfuss | |
| 2007/0067025 | A1 | 3/2007 | Schwartz | |
| 2007/0073307 | A1 | 3/2007 | Scribner et al. | |
| 2007/0073319 | A1 | 3/2007 | Mikkaichi et al. | |
| 2007/0073322 | A1 | 3/2007 | Mikkaichi et al. | |
| 2007/0078435 | A1 | 4/2007 | Stone et al. | |
| 2007/0083236 | A1 | 4/2007 | Sikora et al. | |
| 2007/0093847 | A1 | 4/2007 | Scribner et al. | |
| 2007/0100350 | A1 | 5/2007 | Deffenbaugh et al. | |
| 2007/0112384 | A1 | 5/2007 | Conlon et al. | |
| 2007/0118217 | A1 | 5/2007 | Brulez et al. | |
| 2007/0123883 | A1 | 5/2007 | Ellis et al. | |
| 2007/0142838 | A1 | 6/2007 | Jordan | |
| 2007/0156174 | A1 | 7/2007 | Kaiser et al. | |
| 2007/0162018 | A1 | 7/2007 | Jensen et al. | |
| 2007/0185488 | A1 | 8/2007 | Pohjonen et al. | |
| 2007/0185532 | A1 | 8/2007 | Stone et al. | |
| 2007/0185568 | A1 | 8/2007 | Schwartz | |
| 2007/0191849 | A1 | 8/2007 | ElAttrache et al. | |
| 2007/0191853 | A1 | 8/2007 | Stone | |
| 2007/0219558 | A1* | 9/2007 | Deutsch | 606/72 |
| 2007/0225719 | A1 | 9/2007 | Stone et al. | |
| 2007/0233241 | A1 | 10/2007 | Graf et al. | |
| 2007/0239209 | A1 | 10/2007 | Fallman | |
| 2007/0239275 | A1 | 10/2007 | Willobee | |
| 2007/0250059 | A1 | 10/2007 | Weisshaupt et al. | |
| 2007/0250163 | A1 | 10/2007 | Cassani | |
| 2007/0260251 | A1 | 11/2007 | Weier et al. | |
| 2007/0260279 | A1 | 11/2007 | Hotter et al. | |
| 2007/0270856 | A1 | 11/2007 | Morales et al. | |
| 2007/0270878 | A1 | 11/2007 | Leisinger | |
| 2007/0276387 | A1 | 11/2007 | Morales et al. | |
| 2007/0288023 | A1* | 12/2007 | Pellegrino et al. | 606/72 |
| 2008/0027440 | A1* | 1/2008 | Marissen et al. | 606/72 |
| 2008/0027446 | A1 | 1/2008 | Stone et al. | |
| 2008/0046009 | A1 | 2/2008 | Albertorio et al. | |
| 2008/0051836 | A1 | 2/2008 | Foerster et al. | |
| 2008/0065114 | A1 | 3/2008 | Stone et al. | |
| 2008/0071299 | A1 | 3/2008 | Allinniemi et al. | |
| 2008/0082101 | A1 | 4/2008 | Reisberg | |
| 2008/0082127 | A1 | 4/2008 | Stone et al. | |
| 2008/0082128 | A1 | 4/2008 | Stone | |
| 2008/0114460 | A1 | 5/2008 | Willobee et al. | |
| 2008/0119892 | A1 | 5/2008 | Brailovski et al. | |
| 2008/0132753 | A1 | 6/2008 | Goddard | |
| 2008/0132932 | A1 | 6/2008 | Hoeppner et al. | |
| 2008/0132948 | A1 | 6/2008 | Surti et al. | |
| 2008/0140092 | A1 | 6/2008 | Stone et al. | |
| 2008/0140093 | A1 | 6/2008 | Stone et al. | |
| 2008/0140128 | A1 | 6/2008 | Smisson et al. | |
| 2008/0161852 | A1 | 7/2008 | Kaiser et al. | |
| 2008/0161861 | A1 | 7/2008 | Huebner | |
| 2008/0172097 | A1 | 7/2008 | Lerch et al. | |
| 2008/0188933 | A1 | 8/2008 | Koob et al. | |
| 2008/0188936 | A1 | 8/2008 | Ball et al. | |
| 2008/0221527 | A1 | 9/2008 | Bradley et al. | |
| 2008/0221578 | A1 | 9/2008 | Zeitani | |
| 2008/0255613 | A1 | 10/2008 | Kaiser et al. | |
| 2008/0257363 | A1 | 10/2008 | Schoenefeld et al. | |
| 2008/0262544 | A1 | 10/2008 | Burkhart | |
| 2008/0268064 | A1 | 10/2008 | Woodell-May | |
| 2008/0269674 | A1 | 10/2008 | Stone | |
| 2008/0275477 | A1 | 11/2008 | Sterrett et al. | |
| 2008/0300611 | A1 | 12/2008 | Houser et al. | |
| 2008/0312689 | A1 | 12/2008 | Denham et al. | |
| 2009/0018589 | A1 | 1/2009 | Smisson, III et al. | |
| 2009/0018655 | A1 | 1/2009 | Brunelle et al. | |
| 2009/0054928 | A1 | 2/2009 | Denham et al. | |
| 2009/0062854 | A1 | 3/2009 | Kaiser et al. | |
| 2009/0082790 | A1* | 3/2009 | Shad et al. | 606/148 |
| 2009/0082805 | A1 | 3/2009 | Kaiser et al. | |
| 2009/0099598 | A1 | 4/2009 | McDevitt et al. | |
| 2009/0105717 | A1 | 4/2009 | Bluechel | |
| 2009/0105754 | A1 | 4/2009 | Sethi | |
| 2009/0118774 | A1 | 5/2009 | Miller, III | |
| 2009/0118775 | A1 | 5/2009 | Burke | |
| 2009/0125073 | A1 | 5/2009 | Rehm | |
| 2009/0138002 | A1 | 5/2009 | Fenton | |
| 2009/0138054 | A1 | 5/2009 | Teague et al. | |
| 2009/0156997 | A1 | 6/2009 | Trenhaile | |
| 2009/0163949 | A1 | 6/2009 | Rolnick et al. | |
| 2009/0177233 | A1 | 7/2009 | Malek | |
| 2009/0192468 | A1 | 7/2009 | Stone | |
| 2009/0198277 | A1 | 8/2009 | Gordon et al. | |
| 2009/0204146 | A1 | 8/2009 | Kaiser et al. | |
| 2009/0228042 | A1 | 9/2009 | Koogle, Jr. et al. | |
| 2009/0234357 | A1 | 9/2009 | Morales et al. | |
| 2009/0234358 | A1 | 9/2009 | Morales et al. | |
| 2009/0240251 | A1 | 9/2009 | Gabele | |
| 2009/0248091 | A1 | 10/2009 | Teague et al. | |
| 2009/0265014 | A1 | 10/2009 | May et al. | |
| 2009/0287215 | A1 | 11/2009 | Fisher et al. | |
| 2009/0306711 | A1 | 12/2009 | Stone et al. | |
| 2009/0312776 | A1 | 12/2009 | Kaiser et al. | |
| 2009/0312793 | A1* | 12/2009 | Huxel et al. | 606/232 |
| 2009/0318960 | A1 | 12/2009 | Burkhart | |
| 2009/0318961 | A1 | 12/2009 | Stone et al. | |
| 2010/0042114 | A1 | 2/2010 | Schaffhausen | |
| 2010/0087857 | A1 | 4/2010 | Stone et al. | |
| 2010/0094355 | A1* | 4/2010 | Trenhaile | 606/304 |
| 2010/0121348 | A1* | 5/2010 | van der Burg et al. | 606/139 |
| 2010/0145384 | A1 | 6/2010 | Stone et al. | |
| 2010/0191342 | A1 | 7/2010 | Byrd et al. | |
| 2010/0211071 | A1 | 8/2010 | Lettmann et al. | |
| 2010/0211075 | A1 | 8/2010 | Stone | |
| 2010/0256677 | A1 | 10/2010 | Albertorio et al. | |
| 2010/0268273 | A1 | 10/2010 | Albertorio et al. | |
| 2010/0268275 | A1 | 10/2010 | Stone et al. | |
| 2010/0270306 | A1 | 10/2010 | Shiffer | |
| 2010/0292792 | A1 | 11/2010 | Stone et al. | |
| 2010/0305698 | A1 | 12/2010 | Metzger et al. | |
| 2010/0305709 | A1 | 12/2010 | Metzger et al. | |
| 2010/0312341 | A1 | 12/2010 | Kaiser et al. | |
| 2011/0009885 | A1 | 1/2011 | Graf et al. | |
| 2011/0022083 | A1 | 1/2011 | DiMatteo et al. | |
| 2011/0026141 | A1 | 2/2011 | Barrows | |
| 2011/0046733 | A1 | 2/2011 | Eggli | |
| 2011/0087225 | A1* | 4/2011 | Fritzinger | 606/53 |
| 2011/0087284 | A1 | 4/2011 | Stone et al. | |
| 2011/0098727 | A1 | 4/2011 | Kaiser et al. | |
| 2011/0106153 | A1 | 5/2011 | Stone et al. | |
| 2011/0112537 | A1 | 5/2011 | Bernstein et al. | |
| 2011/0112538 | A1 | 5/2011 | Dell'Oca | |
| 2011/0160767 | A1 | 6/2011 | Stone et al. | |
| 2011/0160768 | A1 | 6/2011 | Stone et al. | |
| 2011/0208239 | A1 | 8/2011 | Stone et al. | |
| 2011/0208240 | A1 | 8/2011 | Stone et al. | |
| 2011/0213416 | A1 | 9/2011 | Kaiser | |
| 2011/0218625 | A1 | 9/2011 | Berelsman et al. | |
| 2011/0224799 | A1 | 9/2011 | Stone | |
| 2011/0245868 | A1 | 10/2011 | Teeslink et al. | |
| 2011/0264141 | A1 | 10/2011 | Denham et al. | |
| 2011/0270278 | A1 | 11/2011 | Overes et al. | |
| 2011/0270306 | A1 | 11/2011 | Denham et al. | |
| 2012/0004669 | A1 | 1/2012 | Overes et al. | |
| 2012/0041485 | A1 | 2/2012 | Kaiser et al. | |
| 2012/0041486 | A1 | 2/2012 | Stone et al. | |
| 2012/0046693 | A1 | 2/2012 | Denham et al. | |
| 2012/0053630 | A1 | 3/2012 | Denham et al. | |
| 2012/0059417 | A1 | 3/2012 | Norton et al. | |
| 2012/0059418 | A1 | 3/2012 | Denham et al. | |
| 2012/0095470 | A1 | 4/2012 | Kaiser et al. | |
| 2012/0109156 | A1 | 5/2012 | Overes et al. | |
| 2012/0116409 | A1 | 5/2012 | Stone | |
| 2012/0116450 | A1 | 5/2012 | McDevitt et al. | |
| 2012/0116452 | A1 | 5/2012 | Stone et al. | |
| 2012/0123447 | A1 | 5/2012 | Corrao et al. | |
| 2012/0123474 | A1 | 5/2012 | Zajac et al. | |
| 2012/0123541 | A1 | 5/2012 | Albertorio et al. | |
| 2012/0143215 | A1 | 6/2012 | Corrao et al. | |
| 2012/0150223 | A1 | 6/2012 | Manos et al. | |
| 2012/0150297 | A1 | 6/2012 | Denham et al. | |
| 2012/0165866 | A1 | 6/2012 | Kaiser et al. | |
| 2012/0165867 | A1 | 6/2012 | Denham et al. | |

(56) References Cited

U.S. PATENT DOCUMENTS

| | | | |
|---|---|---|---|
| 2012/0165938 A1 | 6/2012 | Denham et al. |
| 2012/0197271 A1 | 8/2012 | Astorino et al. |
| 2012/0215257 A1 | 8/2012 | McDevitt et al. |
| 2012/0290004 A1 | 11/2012 | Lombardo et al. |
| 2012/0310245 A1 | 12/2012 | Hoeppner et al. |
| 2013/0018375 A1 | 1/2013 | Dell'Oca |
| 2013/0018416 A1 | 1/2013 | Lombardo et al. |
| 2013/0023928 A1 | 1/2013 | Dreyfuss |
| 2013/0023929 A1 | 1/2013 | Sullivan et al. |
| 2013/0023930 A1 | 1/2013 | Stone et al. |
| 2013/0035698 A1 | 2/2013 | Stone et al. |
| 2013/0035722 A1 | 2/2013 | McDevitt et al. |
| 2013/0046341 A1 | 2/2013 | Stone et al. |
| 2013/0103082 A1 | 4/2013 | Kaiser et al. |
| 2013/0110165 A1 | 5/2013 | Burkhart et al. |
| 2013/0110251 A1 | 5/2013 | Metzger et al. |
| 2013/0116730 A1 | 5/2013 | Denham et al. |
| 2013/0123810 A1 | 5/2013 | Brown et al. |
| 2013/0123813 A1 | 5/2013 | Stone et al. |
| 2013/0131722 A1 | 5/2013 | Marchand et al. |
| 2013/0138123 A1 | 5/2013 | Stone et al. |
| 2013/0144337 A1 | 6/2013 | Stone et al. |
| 2013/0144338 A1 | 6/2013 | Stone et al. |
| 2013/0158601 A1 | 6/2013 | Stone et al. |
| 2013/0190818 A1 | 7/2013 | Norton |
| 2013/0190819 A1 | 7/2013 | Norton |
| 2013/0204276 A1 | 8/2013 | Stone et al. |
| 2013/0211452 A1 | 8/2013 | Stone et al. |
| 2013/0237997 A1 | 9/2013 | Arai et al. |
| 2013/0245761 A1 | 9/2013 | Conner et al. |
| 2013/0274812 A1 | 10/2013 | Dell'Oca |
| 2013/0289564 A1 | 10/2013 | Bernstein et al. |
| 2013/0317621 A1 | 11/2013 | Metzger et al. |
| 2013/0331848 A1 | 12/2013 | Kaiser et al. |
| 2014/0046367 A1 | 2/2014 | Stone et al. |
| 2014/0046368 A1 | 2/2014 | Kaiser et al. |
| 2014/0067081 A1 | 3/2014 | Stone |
| 2014/0088655 A1 | 3/2014 | Stone et al. |
| 2014/0094913 A1 | 4/2014 | Berelsman et al. |
| 2014/0135835 A1 | 5/2014 | Stone et al. |
| 2014/0163613 A1 | 6/2014 | Stone et al. |
| 2014/0163614 A1 | 6/2014 | Denham et al. |
| 2014/0194927 A1 | 7/2014 | Kaiser et al. |
| 2014/0200583 A1 | 7/2014 | Stone et al. |
| 2014/0257378 A1 | 9/2014 | Norton et al. |
| 2014/0276992 A1 | 9/2014 | Stone et al. |
| 2014/0277447 A1 | 9/2014 | Berelsman et al. |
| 2014/0324101 A1 | 10/2014 | Denham et al. |
| 2014/0330311 A1 | 11/2014 | Denham et al. |
| 2014/0350674 A1 | 11/2014 | Stone et al. |
| 2015/0012094 A1 | 1/2015 | Denham et al. |
| 2015/0057757 A1 | 2/2015 | Metzger et al. |

FOREIGN PATENT DOCUMENTS

| | | |
|---|---|---|
| AU | 5850469 | 1/1971 |
| AU | 5963869 | 2/1971 |
| AU | 1505470 | 11/1971 |
| AU | 2223767 | 5/1973 |
| AU | 3615171 | 5/1973 |
| AU | 5028569 | 9/1973 |
| AU | 7110887 | 10/1987 |
| AU | 639410 | 11/1989 |
| AU | 651929 | 8/1994 |
| DE | 2529669 | 3/1976 |
| DE | 2747312 | 4/1979 |
| DE | 2818254 | 10/1979 |
| DE | 2919009 | 11/1979 |
| DE | 3027138 | 12/1981 |
| DE | 3225620 | 2/1983 |
| DE | 3136083 | 3/1983 |
| DE | 233303 | 2/1986 |
| DE | 4127550 | 2/1993 |
| DE | 4302397 | 7/1993 |
| DE | 29621340 | 5/1998 |
| DE | 19841252 | 3/2000 |
| DE | 20207781 U1 | 8/2002 |
| EP | 19062 A1 | 11/1980 |
| EP | 0108912 | 5/1984 |
| EP | 0129442 | 12/1984 |
| EP | 0172130 | 2/1986 |
| EP | 0241240 | 10/1987 |
| EP | 0241792 | 10/1987 |
| EP | 0260970 | 3/1988 |
| EP | 0270704 | 6/1988 |
| EP | 0282789 | 9/1988 |
| EP | 0315371 | 5/1989 |
| EP | 0317406 | 5/1989 |
| EP | 0340159 | 11/1989 |
| EP | 0346183 | 12/1989 |
| EP | 0349173 | 1/1990 |
| EP | 0374088 | 6/1990 |
| EP | 0409364 | 1/1991 |
| EP | 0415915 | 3/1991 |
| EP | 0440991 | 8/1991 |
| EP | 0441065 | 8/1991 |
| EP | 0451932 | 10/1991 |
| EP | 0464480 | 1/1992 |
| EP | 0497079 | 8/1992 |
| EP | 0502509 | 9/1992 |
| EP | 0502698 | 9/1992 |
| EP | 520177 | 12/1992 |
| EP | 0546726 | 6/1993 |
| EP | 0574707 | 12/1993 |
| EP | 0582514 | 2/1994 |
| EP | 0591991 | 4/1994 |
| EP | 0598219 | 5/1994 |
| EP | 0611551 A1 | 8/1994 |
| EP | 0627203 | 12/1994 |
| EP | 0651979 | 5/1995 |
| EP | 0669110 | 8/1995 |
| EP | 0686373 | 12/1995 |
| EP | 0702933 | 3/1996 |
| EP | 0775473 | 5/1997 |
| EP | 0913123 | 5/1999 |
| EP | 0913131 | 5/1999 |
| EP | 99121106 | 10/1999 |
| EP | 991210527 | 10/1999 |
| EP | 0995409 | 4/2000 |
| EP | 1013229 | 6/2000 |
| EP | 1093773 | 4/2001 |
| EP | 1093774 | 4/2001 |
| EP | 1555945 | 7/2005 |
| EP | 2238944 A2 | 10/2010 |
| EP | 2544607 A1 | 1/2013 |
| EP | 2709557 A1 | 3/2014 |
| FR | 2622790 | 5/1989 |
| FR | 2655840 | 6/1991 |
| FR | 2682867 | 4/1993 |
| FR | 2687911 | 9/1993 |
| FR | 2688689 | 9/1993 |
| FR | 2704140 | 10/1994 |
| FR | 2717070 | 9/1995 |
| FR | 2723528 | 2/1996 |
| FR | 2744010 | 8/1997 |
| FR | 2745999 | 9/1997 |
| FR | 2770764 | 5/1999 |
| GB | 401677 | 11/1933 |
| GB | 1413477 | 11/1975 |
| GB | 1485681 | 9/1977 |
| GB | 2083751 | 3/1982 |
| GB | 2118474 | 11/1983 |
| GB | 2227175 | 7/1990 |
| GB | 2253147 A | 9/1992 |
| GB | 2312376 | 10/1997 |
| GB | 2403416 A | 1/2005 |
| JP | 5362911 | 5/1978 |
| JP | 5362912 | 5/1978 |
| JP | 5374942 | 6/1978 |
| JP | 5378230 | 6/1978 |
| JP | 62159647 | 7/1987 |
| JP | 62295657 | 12/1987 |
| JP | 5269160 | 10/1993 |

(56) References Cited

FOREIGN PATENT DOCUMENTS

| | | |
|---|---|---|
| JP | 5300917 | 11/1993 |
| JP | 751292 | 2/1995 |
| JP | 10211213 | 8/1998 |
| WO | WO-8300615 | 3/1983 |
| WO | WO-8603666 | 7/1986 |
| WO | WO-8701270 | 3/1987 |
| WO | WO-8901767 | 3/1989 |
| WO | WO-8909030 | 10/1989 |
| WO | WO-8910096 | 11/1989 |
| WO | WO-9008510 | 8/1990 |
| WO | WO-9203980 | 3/1992 |
| WO | WO-9314705 | 8/1993 |
| WO | WO-9315694 | 8/1993 |
| WO | WO-9502373 | 1/1995 |
| WO | WO-9503003 | 2/1995 |
| WO | WO-9529637 | 11/1995 |
| WO | WO-9532670 | 12/1995 |
| WO | WO-9629029 | 9/1996 |
| WO | WO-9737603 | 10/1997 |
| WO | WO-9812991 | 4/1998 |
| WO | WO-9812992 | 4/1998 |
| WO | WO-9822047 | 5/1998 |
| WO | WO-9822048 | 5/1998 |
| WO | WO-9901084 | 1/1999 |
| WO | WO-9912480 | 3/1999 |
| WO | WO-9944544 | 9/1999 |
| WO | WO-0040159 | 7/2000 |
| WO | WO-0139671 | 6/2001 |
| WO | WO-0236020 | 5/2002 |
| WO | WO-03005914 A1 | 1/2003 |
| WO | WO-03071962 | 9/2003 |
| WO | WO-03077772 | 9/2003 |
| WO | WO-2004091412 A1 | 10/2004 |
| WO | WO-2005104992 A1 | 11/2005 |
| WO | WO-2005122954 A1 | 12/2005 |
| WO | WO-2007103562 A2 | 9/2007 |
| WO | WO-2008002550 A2 | 1/2008 |
| WO | WO-2009012021 A1 | 1/2009 |
| WO | WO-2011112371 A1 | 9/2011 |
| WO | WO-2011150238 A1 | 12/2011 |
| WO | WO-2013066974 A1 | 5/2013 |
| WO | WO-2013074525 A1 | 5/2013 |
| WO | WO-2014/100109 A1 | 6/2014 |
| WO | WO-2014151766 A1 | 9/2014 |

OTHER PUBLICATIONS

International Preliminary Report on Patentability and Written Opinion mailed Nov. 28, 2013 for PCT/US2012/037703, which claims benefit of U.S. Appl. No. 13/109,672, filed May 17, 2011,and U.S. Appl. No. 13/109,667, filed May 17, 2011.
"Arthroscopic Meniscal Repair using the Meniscal Cinch™", Surgical Technique brochure. (2008) Arthrex® 6 sheets.
Pioneer® Sternal Cable System (2010).
Rapid Sternal Closure (2006) KLS Martin L.P. http://www.rapidsternalclosure.com/medical/demo.php Web accessed Sep. 8, 2008.
Saxena, Pankaj, MCh, DNB et al., "Use of Double Wires in Sternal Closure, a Useful Technique," Texas Heart® Institute. Journal List>Tex Heart Inst J > v.33(4); (2006).
Zeitani, Jacob, M.D., "A New Sternal Reinforcement Device to Prevent and Treat Sternal Dehiscence," CTSNet.org (Jun. 30, 2008).
International Search Report and Written Opinion mailed Mar. 6, 2014 for PCT/US2013/075989 which claims benefit of U.S. Appl. No. 13/720,648, filed Dec. 19, 2012.
International Preliminary Report on Patentability mailed Sep. 20, 2012 for PCT/US2011/026349 which claims benefit of U.S. Appl. No. 12/719,337, filed Mar. 8, 2010.
International Preliminary Report on Patentability mailed Dec. 6, 2012 for PCT/US2011/038188 claiming benefit of U.S. Appl. No. 12/788,966, filed May 27, 2010.
Invitation to Pay Additional Fees mailed Jul. 19, 2012, for PCT/US2012/037703 claiming benefit of U.S. Appl. No. 13/109,667, filed May 7, 2011.

"ToggleLoc™ Fixation Device with ZipLoop™ Technology: ACL Reconstruction Bone-Tendon-Bone," by James R. Andrews, M.D., of Biomet Sports Medicine, a Biomet Company Brochure (2013), pp. 1-20.
International Preliminary Report on Patentability and Written Opinion mailed May 30, 2014 for PCT/US2012/064832 which claims benefit of U.S. Appl. No. 13/295,126, filed Nov. 14, 2011.
International Search Report and Written Opinion mailed Jun. 6, 2014 for PCT/US2014/026413 which claims benefit of U.S. Appl. No. 14/095,614, filed Dec. 3, 2013 and U.S. Appl. No. 14/095,639, filed Dec. 3, 2013.
ToggleLoc Fixation Device with ZipLoop Technology: Biceps Tendon Reattachment by Mark J. Albritton, M.D. and Daniel Worrel, M.D. of Biomet Sports Medicine, a Biomet Company Brochure (2099, 2011), pp. 1-12.
International Search Report and Written Opinion mailed Feb. 6, 2013 for PCT/US2012/064832 which claims benefit of U.S. Appl. No. 13/295,126, filed Nov. 14, 2011.
International Search Report and Written Opinion mailed Mar. 6, 2013 for PCT/US2012/062738 which claims benefit of U.S. Appl. No. 13/288,459, filed Nov. 3, 2011.
US 6,238,418, 5/2001, Schwartz et al. (withdrawn).
"AperFix® System Surgical Technique Guide. Single Tunnel Double Bundle.™" Cayenne Medical brochure. (Aug. 2008) 8 sheets.
"Bio-Intrafix (TCP/PLA & Intrafix, Tibial Soft Tissue Fasteners," by DePuy Mitek, 6 sheets, (date unknown).
"Bio-Intrafix Tibial Soft Tissue Fasteners, Building on the Legacy of IntraFix," brochure. DePuy Mitek,(Feb. 2007) 6 sheets.
"Biomechanical Evaluation of the Biomet Sports Medicine JurggerKnot™ Soft Anchor in Porcine Bone," Study completed Jan. 2010. Biomet Sports Medicine Research and Development, Warsaw, Indiana. 2 pages.
"Do your next distal tendon repair with . . . The Lubbers Technique", Teno Fix® brochure, 2003 (2 pages) Ortheon® Medical.
"EZ Loc Femoral Fixation Device," copyright 2005 Arthrotek, Inc. (8 sheets).
"JuggerKnot™ Soft Anchor Midfoot Repair," brochure. Biomet Sports Medicine (Jul. 2011) 12 sheets.
"JuggerKnot™ Soft Anchor. It's Small. It's strong. And it's all suture . . . " Ordering Information brochure. Biomet Sports Medicine (Jun. 2011) 2 sheets.
"JuggerKnot™ Soft Anchor. Labral Repair," brochure. Biomet Sports Medicine (Apr. 2011) 12 sheets.
"Make your next tendon repair an open-and-shut case. The Teno Fix® Tendon Repair System", Teno Fix® brochure, 2003 (2 pages) Ortheon® Medical.
"Panalok Anchor with PDS II and ETHIBOND Suture", Mitek Products ETHICON, 1997.
"SE Graft Tensioning System Surgical Technique," Linvatec Corporation copyright 2003, 2004.
"Technique for ACL Reconstruction with Acufex Director Drill Guide and Endobutton CL," by Thomas D. Roseberg, copyright 1999 Smith & Nephew.
A. Weiler, et al; Biodegradierbare Interferenzschrauben in der Kreuzbandchirurgie; OP-Journal 14 pp. 278-284; 1998.
Arthrotek, A Biomet Company; Knees; Sure fire Hybrid Meniscal Device. (2005).
Arthrotek, A Biomet Company; Sure fire Hybrid Meniscal Device; Launch Date: Fall AANA 2004.
F. Alan Barber, M.D., "Uses and Abuses of Sutures and Anchors," Shoulder Scope, San Diego Shoulder Arthroscopy Library.
F. Alan Barber, M.D., "Using Sutures and Anchors," San Diego Shoulder Arthroscopy Course, 17th Annual Meeting.
Flavia Namie Azato, et al. "Traction endurance biomechanical study of metallic suture anchors at different insertion angles," Acta ortop. bras., vol. 11, No. 1, Sao Paulo, Jan./Mar. 2003.
Hecker AT, et al., "Pull-out strength of suture anchors for rotator cuff and Bankart lesion repairs," Am J Sports Med. 1993.
International Search Report and Written Opinion mailed Jul. 28, 2011 for PCT/US2011/026349 claiming benefit of U.S. Appl. No. 12/938,902, filed Nov. 3, 2010; and U.S. Appl. No. 12/719,337, filed Mar. 8, 2010.

(56) References Cited

OTHER PUBLICATIONS

International Search Report and Written Opinion mailed Oct. 14, 2011 for PCT/US2011/038188 filed May 26, 2011 claiming benefit of U.S. Appl. No. 12/788,973, filed May 27, 2010 and U.S. Appl. No. 12/788,966, filed May 27, 2010.

Invitation to Pay Additional Fees mailed Jun. 9, 2011 for PCT/US2011/026349 claiming benefit of U.S. Appl. No. 12/938,902, filed Nov. 3, 2010; and U.S. Appl. No. 12/719,337, filed Mar. 8, 2010.

Lawhorn, M.D., Keith, MaxFire™ Meniscal Repair Device with Zip Loop™ Technology, Biomet Sports Medicine, Feb. 29, 2008.

Mark D. Miller et al.; "Pitfalls Associated with FasT-Fix Meniscal Repair," Arthroscopy: The Journal of Arthroscopic and Related Surgery, vol. 18, No. 8 Oct. 2002: pp. 939-943.

Opus Medical; The AutoCuff System; www.opusmedical.com; 2003.

Patrick Hunt, et al.; Development of a Perforated Biodegradable Interference Screw; Arthroscopy: The Journal of Arthroscopic and Related Surgery, vol. 21, No. 3; pp. 258-265; Mar. 2005.

Roy Alan Majors, M.D.; "Meniscal repairs: proven techniques and current trends," Lippincott Williams & Wilkins, Inc.; 2002.

Shoulder Arthroscopy; pp. H-2-H-22.

Smith & Nephew Endoscopy, "Endoscopic Meniscal Repair Using the T-Fix;" 1996.

Smith & Nephew, "Fast-Fix," Meniscal Repair System; 2001.

Stuart E. Fromm, M.D., RapidLoc, Meniscal Repair System, Mitek Products, Ethicon, 2001.

ToggleLoc™ Femoral Fixation Device, Arthrotek, Mar. 31, 2006.

Ziptight™ Fixation System Featuring Zip Loop™ Technology. Ankle Syndesmosis. Surgical Protocol by Timothy Charlton, M.D. Biomet Sports® Medicine brochure. (Jun. 15, 2011) 8 pages.

\* cited by examiner

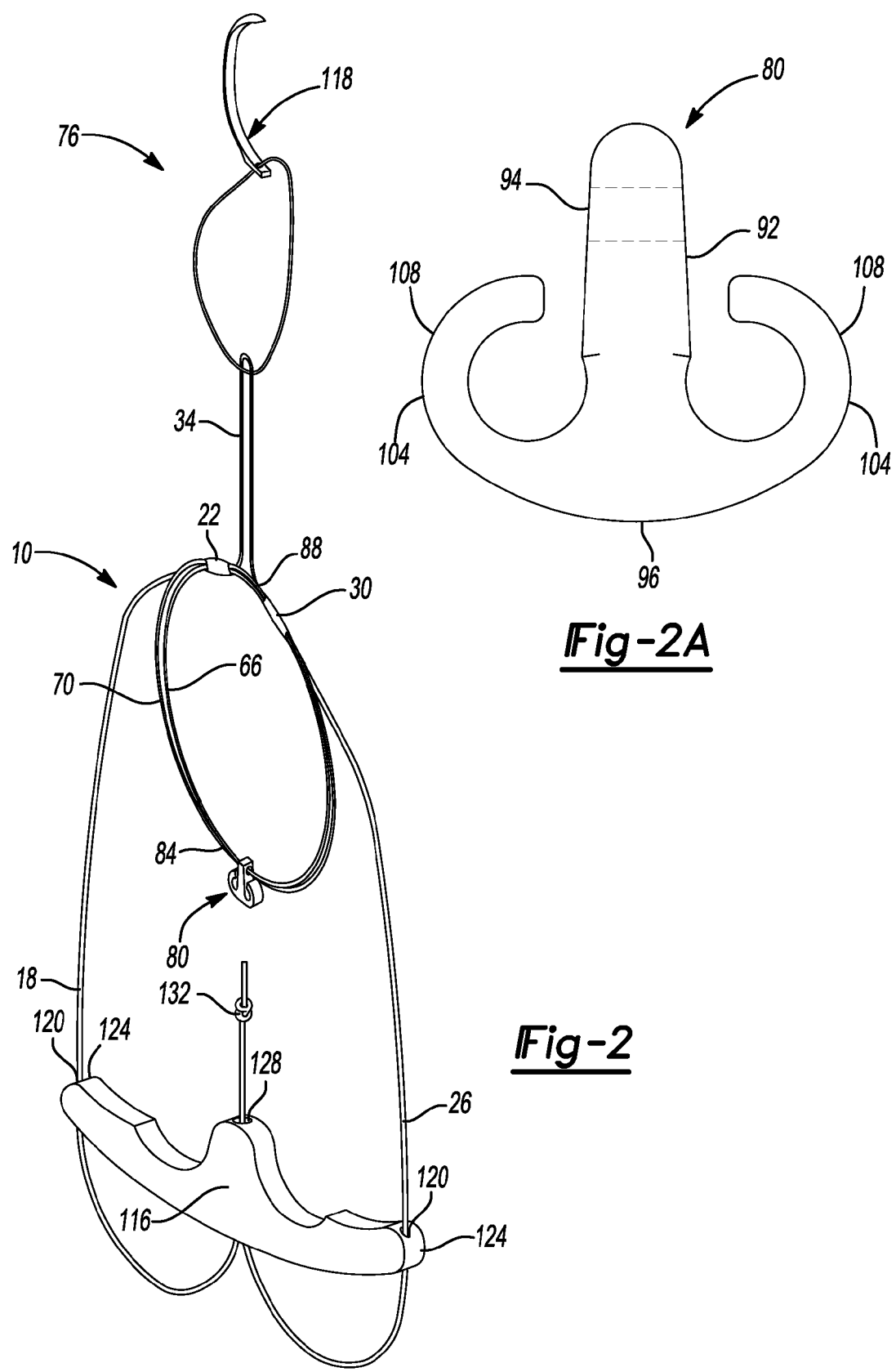

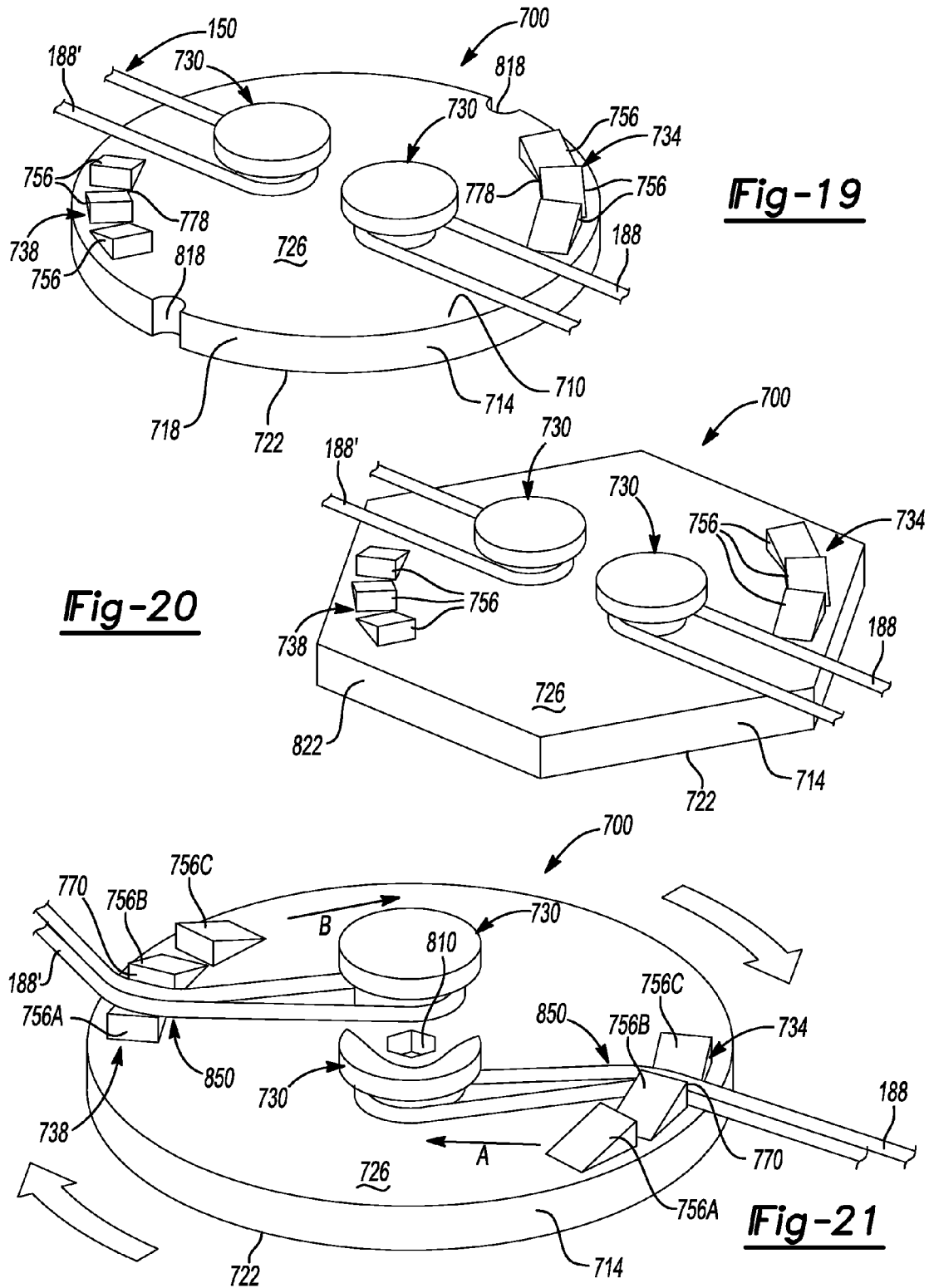

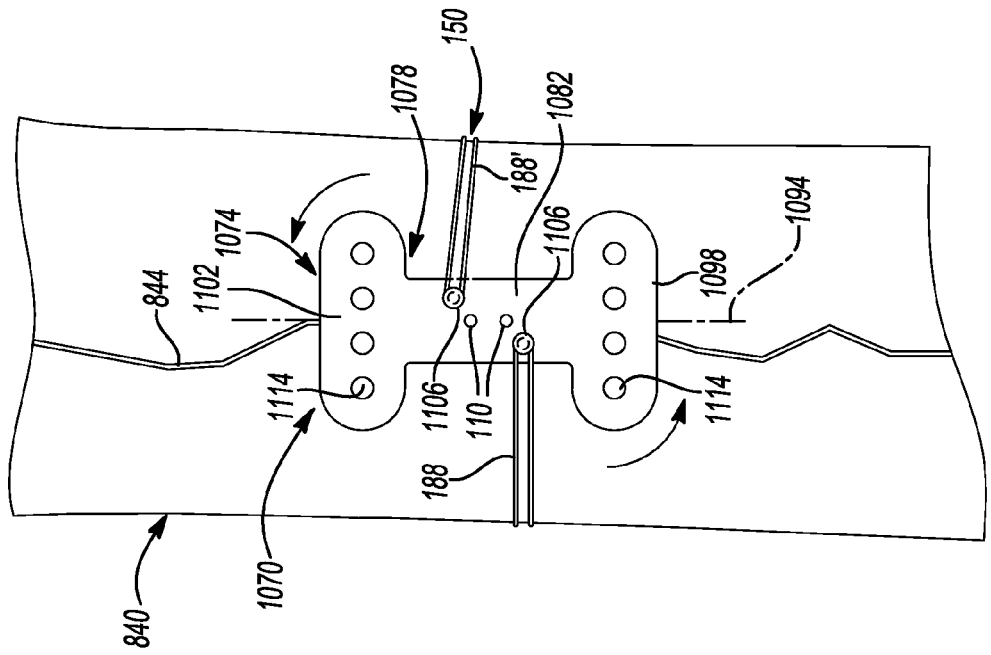
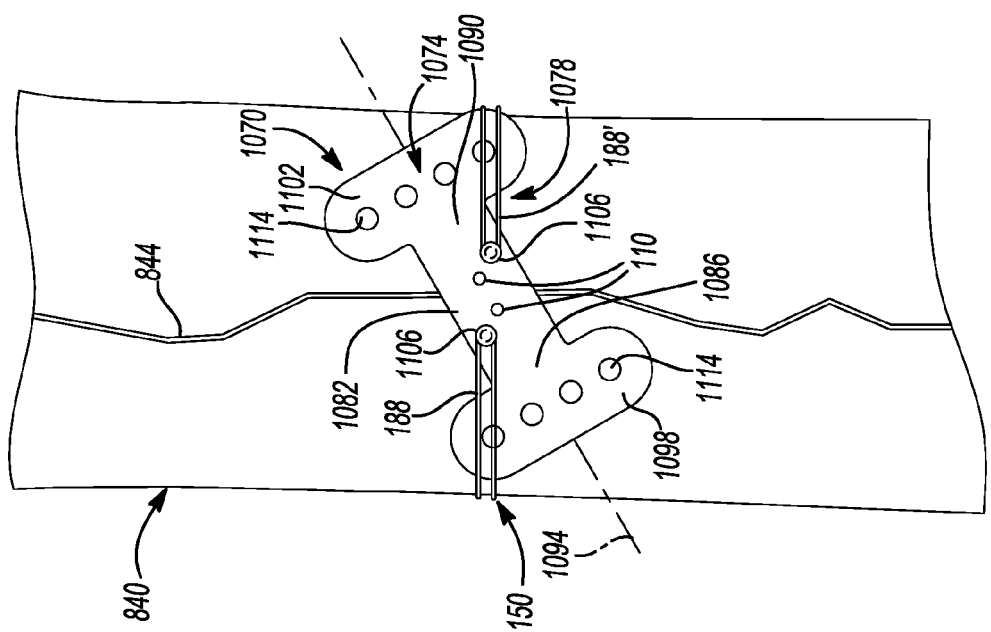

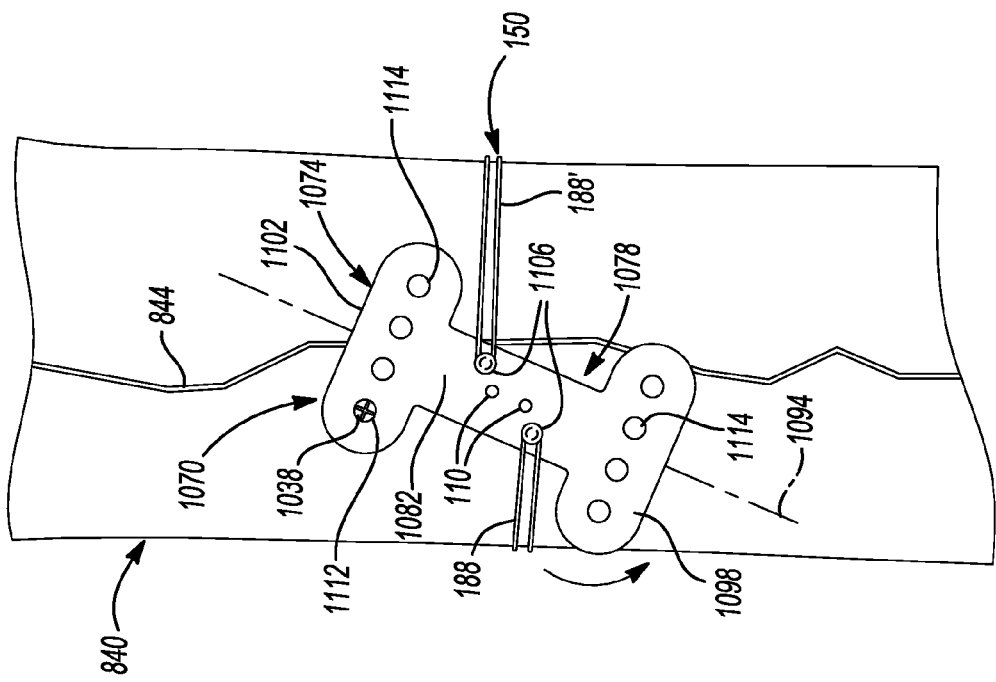
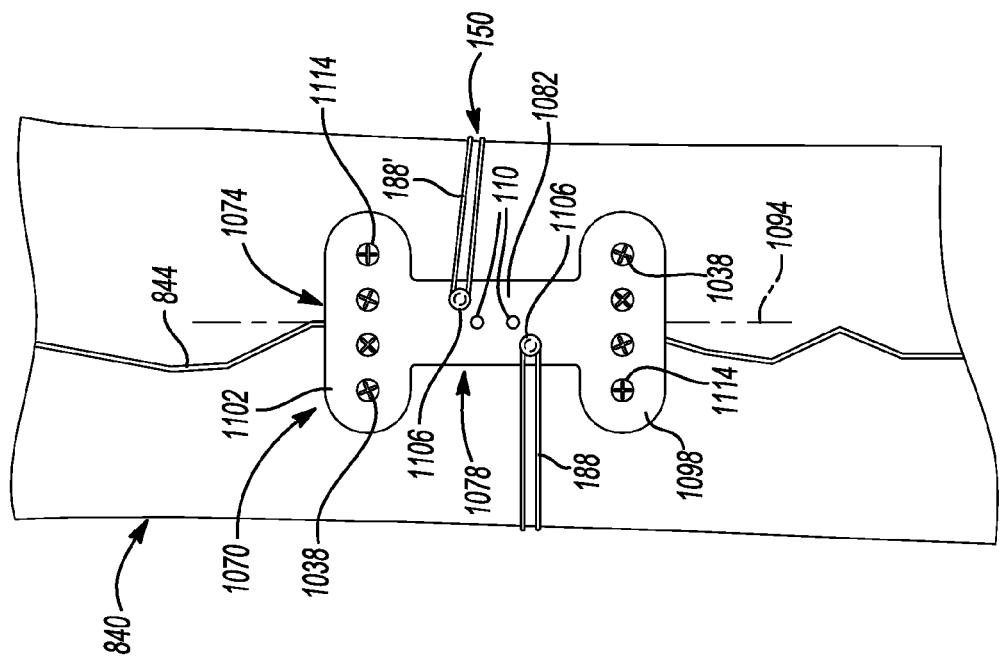

METHOD AND APPARATUS FOR TENSIONING A SUTURE

CROSS-RELATED APPLICATIONS

This application is a continuation-in-part of U.S. patent application Ser. No. 12/938,902 filed on Nov. 3, 2010, now issued as U.S. Pat. No. 8,597,327, which is a continuation-in-part of U.S. patent application Ser. No. 12/915,962 filed on Oct. 29, 2010, now issued as U.S. Pat. No. 8,562,647, which is a continuation-in-part of U.S. patent application Ser. No. 12/719,337 filed on Mar. 8, 2010, now issued as U.S. Pat. No. 9,078,644, which is a continuation-in-part of U.S. patent application Ser. No. 12/489,168 filed on Jun. 22, 2009, now issued as U.S. Pat. No. 8,361,113, which is a continuation-in-part of U.S. patent application Ser. No. 12/474,802 filed on May 29, 2009, now issued as U.S. Pat. No. 8,088,130, which is a continuation-in-part of (a) U.S. patent application Ser. No. 12/196,405 filed on Aug. 22, 2008, now issued as U.S. Pat. No. 8,128,658; (b) U.S. patent application Ser. No. 12/196,407 filed on Aug. 22, 2008, now issued as U.S. Pat. No. 8,137,382; (c) U.S. patent application Ser. No. 12/196,410 filed on Aug. 22, 2008, now issued as U.S. Pat. No. 8,118,836; and (d) a continuation-in-part of U.S. patent application Ser. No. 11/541,506 filed on Sep. 29, 2006, which is now U.S. Pat. No. 7,601,165 issued on Oct. 13, 2009.

This application is a continuation-in-part of U.S. patent application Ser. No. 12/570,854 filed on Sep. 30, 2009, now issued as U.S. Pat. No. 8,303,604, which is a continuation-in-part of U.S. patent application Ser. No. 12/014,399 filed on Jan. 15, 2008, which is now U.S. Pat. No. 7,909,851 issued on Mar. 22, 2011, which is a continuation-in-part of U.S. patent application Ser. No. 11/347,661 filed on Feb. 3, 2006, which is now U.S. Pat. No. 7,749,250 issued on Jul. 6, 2010.

This application is a continuation-in-part of U.S. patent application Ser. No. 12/029,861 filed on Feb. 12, 2008, now issued as U.S. Pat. No. 8,672,968, which is a continuation-in-part of U.S. patent application Ser. No. 11/504,882 filed on Aug. 16, 2006, which is a continuation-in-part of U.S. patent application Ser. No. 11/408,282 filed on Apr. 20, 2006, and now abandoned.

This application is a continuation-in-part of U.S. patent application Ser. No. 12/702,067 filed on Feb. 8, 2010, now issued as U.S. Pat. No. 8,672,968, which is a continuation of U.S. patent application Ser. No. 11/541,505 filed on Sep. 29, 2006 and is now U.S. Pat. No. 7,658,751 issued on Feb. 9, 2010.

This application is a continuation-in-part of U.S. patent application Ser. No. 13/102,182 filed on May 6, 2011, now issued as U.S. Pat. No. 8,231,654, which is a divisional of U.S. patent application Ser. No. 12/196,398 filed Aug. 22, 2008, now U.S. Pat. No. 7,959,650 issued on Jun. 14, 2011, which is a continuation-in-part of U.S. patent application Ser. No. 11/784,821 filed Apr. 10, 2007, now issued as U.S. Pat. No. 9,017,381.

The disclosures of all of the above applications are incorporated by reference herein.

FIELD

The present disclosure relates generally to methods and apparatus for tensioning a suture.

BACKGROUND

The statements in this section merely provide background information related to the present disclosure and may not constitute prior art.

After trauma or surgical intervention, there may be a need to fix bone fragments or portions together to immobilize the fragments and permit healing. Compressive force can be applied to the bone fragments by encircling the bone fragments or bridging the fragments together across a broken, sectioned (cut) or otherwise compromised portion of the bone. The compressive forces should be applied such that upon ingrowth of new bone, the fragments will heal together and restore strength to the site of trauma or surgical intervention.

Accordingly, there is a need for apparatus and methods to apply compressive force to a bone across a fracture or section (cut) to maintain alignment and assist healing. Further, there is a need for apparatus and methods that are easy to use intraoperatively to accommodate various bone sizes or shapes, or locations of bone fractures or sections.

SUMMARY

This section provides a general summary of the disclosure, and is not a comprehensive disclosure of its full scope or all of its features.

In one aspect, an apparatus for applying tension to a suture is provided in accordance with the present teachings. The apparatus can include a tensioning member having a body, first and second suture attachment members and first and second suture engaging members. The body can define a first bone engaging surface, an opposite second suture receiving surface, and an outer perimeter. The first and second suture attachment members can be positioned relative to the second surface and spaced apart from each other, and can be adapted to be coupled to the suture. The first and second suture engaging members can extend from the second surface and can be positioned in spaced relation to the respective first and second suture attachment members. Rotation of the tensioning member in a first direction can be adapted to selectively engage the first and second suture receiving members with the suture, thereby forming a non-linear path of travel of the suture relative to the first and second suture attachment members and suture engaging members and increasing the tension in the suture.

In another aspect, a method for applying tension to a flexible member is provided in accordance with the present teachings. The method can include positioning a tensioning member relative to a first bone portion and a second bone portion, where the tensioning member can have first and second flexible member attachment members and a corresponding set of first and second flexible member engaging members extending therefrom. The flexible member can be positioned about the first and second bone portions and can be coupled to the first and second attachment members. The flexible member can be tensioned to draw the first and second bone portions toward each other under a first tension. The tensioning member can be rotated such that the first and second attachment members draw the flexible member in opposite directions applying additional tension to the flexible member to place the flexible member and the first and second bone portions under a second tension. The flexible member can be engaged with the first and second flexible member engaging members and can create a non-linearity in the flexible member about each of the flexible member engaging members. The second tension can be maintained via engagement of the flexible member with the first and second attachment members and the first and second engagement members in an absence of an external force.

In yet another aspect, a method for applying tension to a suture is provided in accordance with the present teachings.

The method can include positioning a tensioning member relative to a first bone portion and a second bone portion, where the tensioning member can have first and second suture attachment members and a corresponding first and second plurality of suture engaging members extending therefrom. An adjustable suture construct can be positioned about the first and second bone portions. First and second adjustable loops of the adjustable suture construct can be coupled to the first and second attachment members. Free ends of the adjustable suture construct can be tensioned to reduce a size of the first and second adjustable loops and draw the first and second bone portions toward each other under a first tension. The tensioning member can be rotated such that the first and second attachment members draw the adjustable suture construct in opposite directions applying additional tension to the suture construct to place the suture construct and the first and second bone portions under a second tension. The first and second adjustable loops can be engaged with a respective one of the plurality of first and second suture engaging members and can create a non-linearity in the adjustable loops about each of the one of the plurality of first and second suture engaging members. The second tension can be maintained via engagement of the first and second adjustable loops with the first and second suture attachment members and the one of the plurality of first and second suture engagement members in an absence of an external force.

In still another aspect, a method for applying tension to a flexible member is provided in accordance with the present teachings. The method can include positioning a tensioning member in a first position relative to a first bone portion and a second bone portion, where the tensioning member can have first and second flexible member attachment members. The flexible member can be positioned about the first and second bone portions and can be coupled to the first and second attachment members. The flexible member can be tensioned to draw the first and second bone portions toward each other under a first tension. The tensioning member can be rotated to a second position such that the first and second attachment members draw first and second ends of the flexible member in opposite directions applying additional tension to the flexible member to place the flexible member and the first and second bone portions under a second tension. The tensioning member can be secured in the second position to at least one of the first and second bone portions to maintain the second tension.

In another aspect, an apparatus for applying tension to a suture is provided in accordance with the present teachings. The apparatus can include a tensioning member having a first member and a second member. The first member can have a body defining a first bone engaging surface, an opposite second surface, and a pocket formed in the second surface and extending toward the first surface. The pocket can include a first retention arrangement. The second member can be sized and shaped to be received in the pocket and can include a first lower surface and a second upper surface. The second upper surface can include first and second suture attachment members spaced apart from each other. The first and second suture attachment members can be adapted to be coupled to the suture, where the second member can be configured to be positioned at least partially into the pocket and can include a second retention arrangement operable to engage the first retention arrangement. The second member can be configured to be rotated relative to the first member to impart tension onto the suture, wherein the first retention arrangement can be configured to engage the second retention arrangement to prevent rotation of the second member relative to the first member in at least one rotational direction.

In yet another aspect, a method for applying tension to a flexible member is provided in accordance with the present teachings. The method can include positioning a first member of a tensioning member assembly relative to a first bone portion and a second bone portion, where the tensioning member can include a pocket formed therein on an upper surface opposite a lower bone engaging surface. The flexible member can be positioned about the first and second bone portions and can be coupled to first and second attachment members associated with a second member of the tensioning member assembly. The second member can be rotated in a first rotational direction relative to the pocket of the first member to impart tension onto the flexible member. The second member can be positioned in the pocket of the first member such that a second retention arrangement associated with the second member engages a first retention arrangement associated with the pocket of the first member to prevent rotation of the second member relative to the first member in a second rotational direction opposite the first rotational direction to maintain the tension imparted onto the flexible member.

Further areas of applicability will become apparent from the description provided herein. The description and specific examples in this summary are intended for purposes of illustration only and are not intended to limit the scope of the present disclosure.

DRAWINGS

The present teachings will become more fully understood from the detailed description, the appended claims and the following drawings. The drawings are for illustrative purposes only and are not intended to limit the scope of the present disclosure.

FIG. 2 depicts an exemplary assembly configuration of the flexible member construct of FIG. 1 having an attachment member and an insertion member according to the present teachings;

FIG. 2A depicts a side view of the attachment member of FIG. 2 according to the present teachings;

FIGS. 17-21 depict aspects of an exemplary tensioning member for tensioning a flexible member construct according to the present teachings;

FIGS. 37-40 depict aspects of another exemplary tensioning member for tensioning a flexible member construct according to the present teachings;

DETAILED DESCRIPTION

Figure 1:
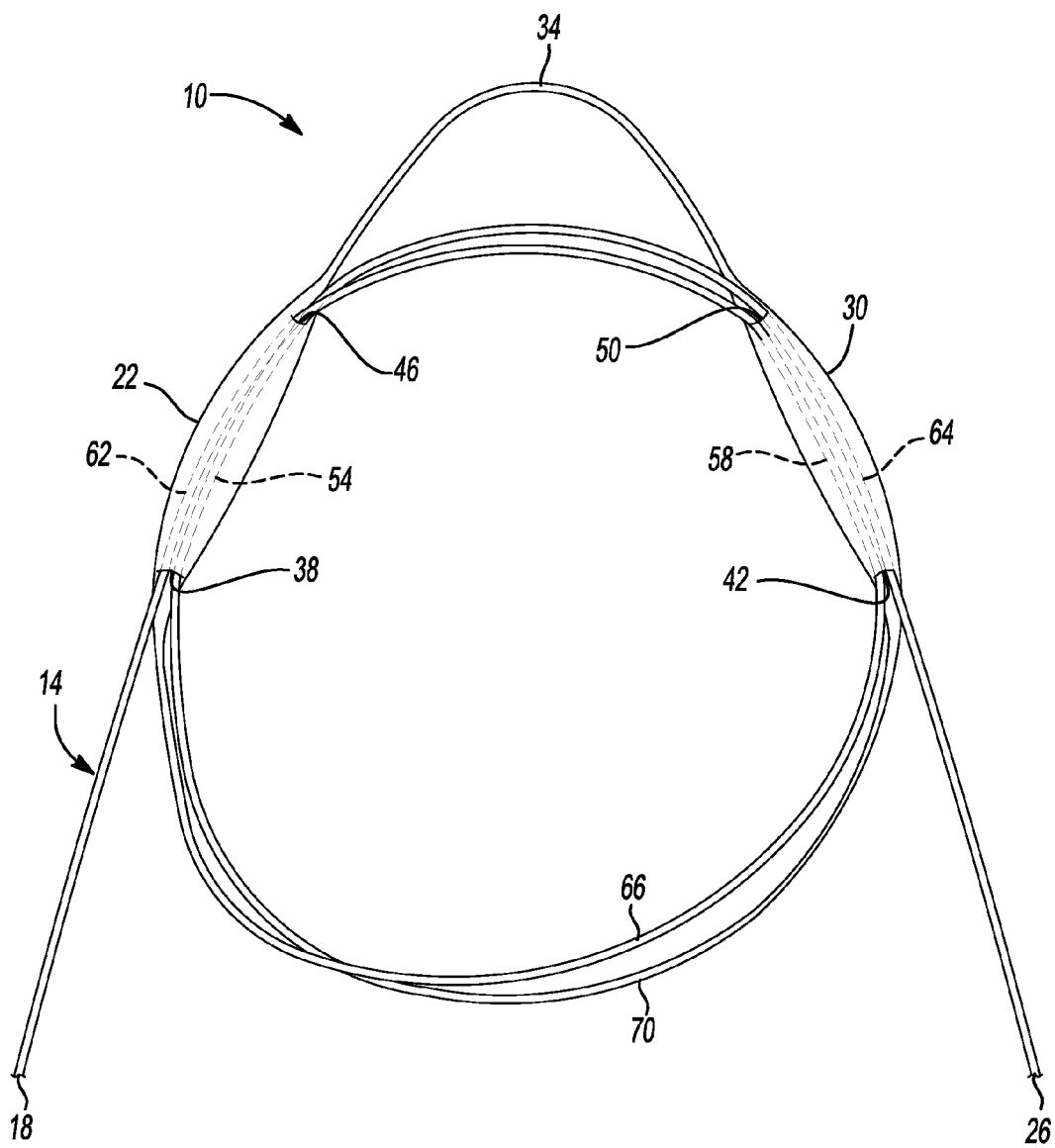
FIG. 1 depicts an adjustable flexible member construct according to the present teachings.

The following description is merely exemplary in nature and is in no way intended to limit the present disclosure, its application, or uses. It should be understood that throughout the drawings, corresponding reference numerals indicate like or corresponding parts and features. While the disclosure generally relates to apparatus and associated methods for tensioning a suture in connection with a fractured or section bone, such as in a sternal closure procedure, the apparatus and methods of the present teachings can be used in connection with various other fracture fixation methods and/or other procedures where suture tensioning is required, such as for example, in tensioning soft tissue or portions of two separate bones.

Referring to FIG. 1, an adjustable flexible member construct 10 is provided according to various aspects of the present teachings. The adjustable flexible member construct 10 can be fashioned from a flexible member 14 made of any biocompatible material including, but not limited to, non-resorbable polymers, such as polyethylene or polyester, resorbable polymers, and various combinations thereof. In various aspects, the adjustable flexible member construct 10 can include a hollow material or core to allow for appropriate tensioning, as will be discussed herein. In various aspects, the adjustable flexible member construct 10 can be a suture. In such aspects, the suture can be hollow or a braided or a multiple-filament braided suture structure having a hollow core. In various aspects, the suture can be resorbable. In various aspects, the adjustable flexible member construct 10 can define a substantially tubular hollow shape.

The adjustable flexible member construct 10 can include a first end 18, a first formed passage portion 22, a second end 26, a second formed passage portion 30, and a fixed length loop portion 34 connecting the first and second passage portions 22, 30, as shown in FIG. 1. In one exemplary aspect, flexible member construct 10 can include an elongated body 32 having an exterior surface and an interior surface defining an elongated passage between the first and second ends 18, 26. The body 32 can define the first and second passage portions 22, 30 and the fixed length portion 34 therebetween. Passage portions 22, 30 can each include first apertures 38, 42 positioned proximate one end thereof, and second apertures 46, 50 positioned proximate a second opposite end thereof. The passage portions 22, 30 can be formed to have a larger width or diameter than remaining portions of flexible member 14, as shown for example in FIG. 1. Alternatively, the passage portions 22, 30 can be formed initially to have the same width or diameter as the remaining portions of flexible member 14, later expanding in diameter during the construction process. In various aspects, the first and second apertures 38, 42, 46, 50 can be formed during a braiding process of flexible member 14 as loose portions between pairs of fibers defining flexible member 14, or can be formed during the construction process. Alternatively, the first and second ends can be pushed between individual fibers of the braided flexible member 14, as will be discussed herein.

Figure 1A:
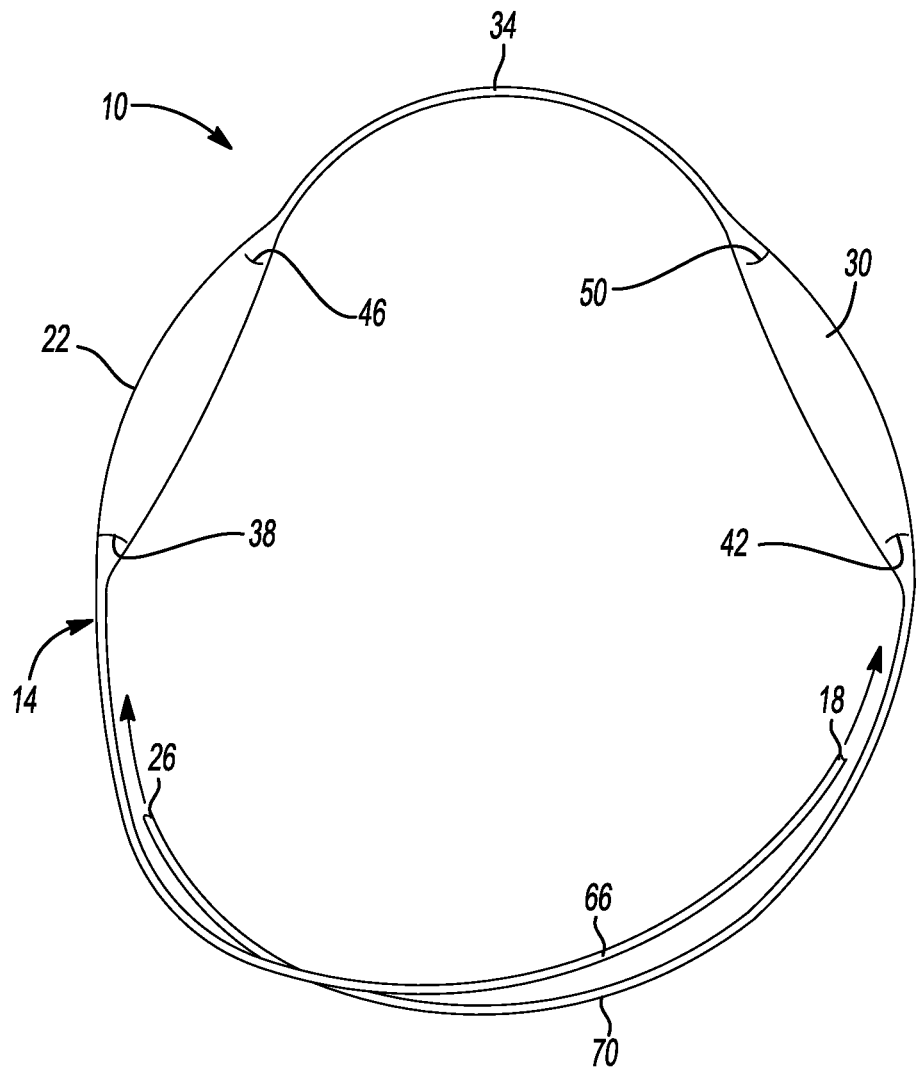
FIGS. 1A and 1B depict an exemplary method of assembling the adjustable flexible construct of FIG. 1 according to the present teachings.
Figure 1B:
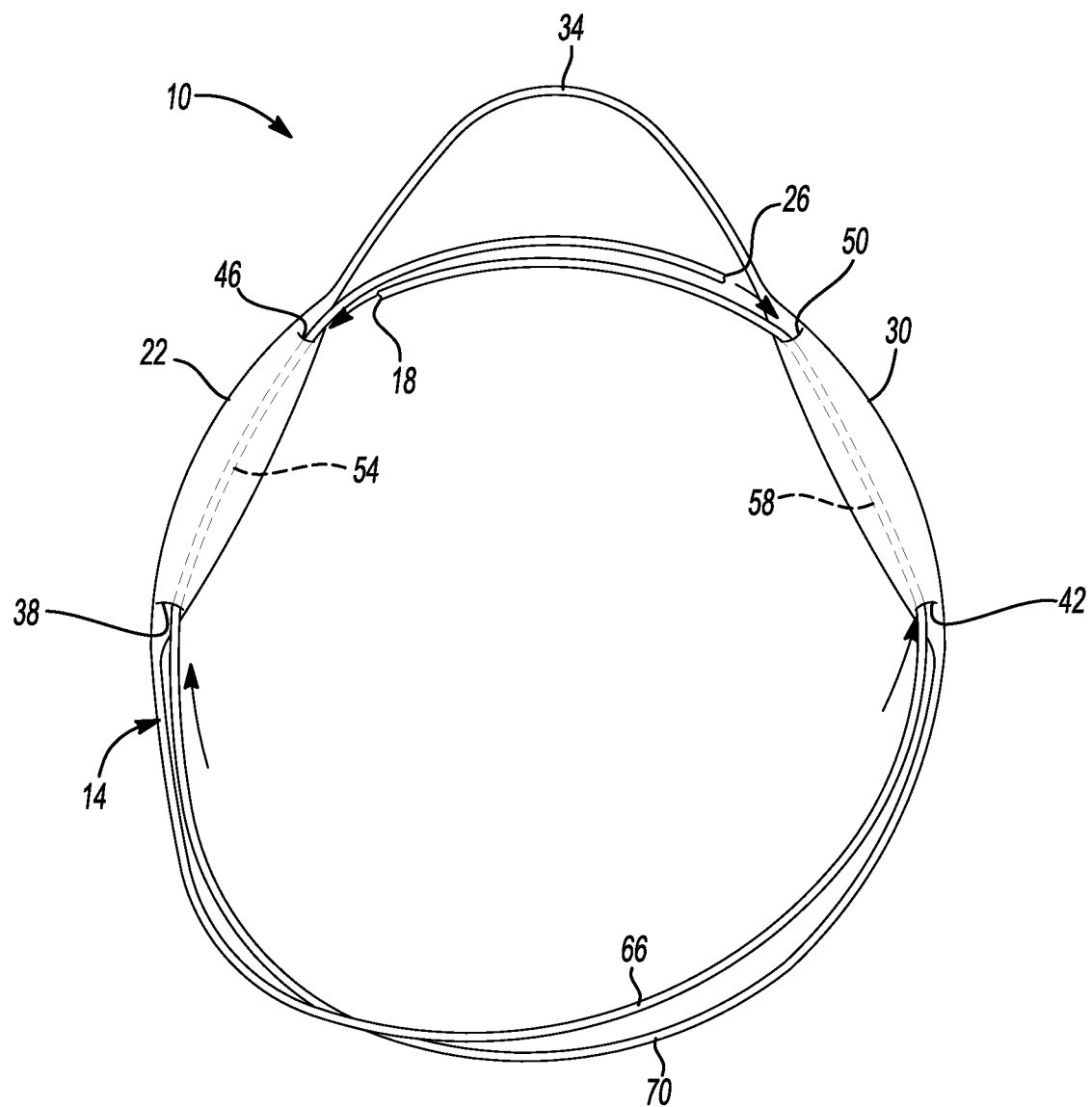

To form the adjustable flexible member construct 10, first end 18 can be passed through second passage portion 30 via first and second apertures 42, 50, as generally shown in FIGS. 1A and 1B. In a similar manner, second end 26 can be passed through the first passage portion 22 via the first and second apertures 38, 46, as also shown in FIGS. 1A and 1B. Subsequently, as shown in FIG. 1B with reference to FIG. 1, first end 18 can be passed through the first passage portion 22 via second and first apertures 46 and 38, respectively. First end 18 can follow a path that is opposite in direction to a path followed by a portion 54 of the flexible member 14 that has already passed through first passage portion 22 while following second end 26 through first and second apertures 38 and 46. Similarly, second end 26 can be passed through the second passage portion 30 via second and first apertures 50 and 42, respectively. First end 26 can follow a path that is opposite in direction to a path followed by a portion 58 of the flexible member 14 that has already passed through second passage portion 30 while following first end 18 through first and second apertures 42 and 50. This results in portions 62, 64 of flexible member 14 being positioned parallel or substantially parallel to portions 54, 58 in passage portions 22, 30. Passing the first and second ends 18, 26 though passage portions 22, 30 as discussed above forms adjustable loops 66, 70, as shown in FIG. 1. The first and second ends can be passed through the same apertures in each passage portion 22, 30 or, alternatively, through separate apertures in each passage portion 22, 30.

The adjustable flexible member construct 10 can thus provide a double adjustable loop configuration via loops 66, 70 while also providing portion 34, which can have a fixed length between the passage portions 22, 30. As will be discussed in greater detail herein, this configuration can be used, for example, to couple an attachment member to loops 66, 70 and couple fixed length portion 34 to either the attachment member or another device. In this manner, the amount of friction developed within the first and second passage portions 22, 30 relative to and among portions 54, 58, 62 and 64 during adjustment of adjustable loops 66, 70 is reduced as compared to that which would occur if the attachment member were coupled to the passage portion when the loops are being adjusted or reduced in size under tension.

With additional reference to FIGS. 2 and 2A, adjustable flexible member construct 10 is shown in an exemplary assembly configuration 76 having an attachment member 80 coupled to a first side 84 of loops 66, 70 opposite a second side 88 facing fixed length portion 34. Attachment member 80 can include a generally T-shaped configuration having a first stem portion 92 defining an aperture 94 for receipt of loops 66, 70 therein at one end, and a transversely extending cross portion 96 at a second opposite end. Transversely extending portion 96 can include opposed lateral ends 104 that include arcuate or curled portions 108, as shown in FIG. 2A. In various aspects, attachment member 80 can be used to secure a flexible member loop thereto by placing the loop over first portion 92 and under arcuate portions 108, as shown for example in FIG. 4.

The assembly configuration 76 can also include an optional grab member or handle 116 and a passing or needle member 118. Handle 116 can be used to aid the surgeon in easily pulling ends 18, 26 of construct 10 to reduce the size of loops 66, 70, as will be discussed in greater detail below. Handle 116 can include a first pair of apertures 120 positioned at opposed ends 124 of handle 116, as shown in FIG. 2. The first and second ends 18, 26 can be passed or routed through apertures 120 and then through a central aperture 128, where ends 18, 26 can be secured to handle 116 by various methods, including a knot 132, as also shown in FIG. 2. The surgeon can use handle 116 to apply simultaneous tension to ends 18, 26, which can thereby evenly reduce or adjust loops 66, 70 to a desired size or tension.

Operation of the adjustable flexible member construct 10 will now be described in greater detail with reference to an exemplary configuration where adjustable flexible member construct 10 is wrapped around or encircles a bone, such as a sternum, and fixed loop 34 is connected to attachment member 80, as shown for example in FIG. 4. It should be appreciated, however, that construct 10 can be used in various attachment configurations, other than the example discussed above, wherein tension is applied to construct 10 via fixed loop 34 and attachment member 80 in connection with reducing or adjusting the size of loops 66, 70.

Upon applying tension to ends 18, 26, with or without handle 116, the loops 66, 70 can be reduced to a desired size and/or placed in a desired tension by causing translation of ends 18, 26 relative to passage portions 22, 30. Tension in fixed length loop portion 34 combined with the tension in adjustable loops 66, 70 can cause the body 32 of flexible member 14 defining the passage portions 22, 30 to constrict about the portions 54, 58 and 62, 64 of flexible member 14 passed therethrough. This constriction can reduce a width or diameter of each of the passage portions 22, 30, thereby forming a mechanical interface between exterior surfaces of the passed through portions of flexible member 14 and interior surfaces of the passage portions 22, 30. The static friction between the interior and exterior surfaces at the mechanical interface formed as a result of the constriction can prevent relative movement of portions 54, 58, and 62, 64 relative to passages 22, 30 and hence prevent relaxation of the tension in construct 10, thereby preventing an increase in the size of loops 66, 70. Thus, adjustable flexible member construct 10 provides for "automatically" locking loops 66, 70 in a reduced length or size under tension without requiring a knot.

Flexible member construct 10 can be provided in various sizes to accommodate differently sized bones, such as sternums, in different patients. In one exemplary configuration, fixed loop portion 34 can be provided in various sizes or lengths. Flexible member construct 10 can also be provided with flexible member 14 having various diameters, such as 30 thousandths of an inch or 37-40 thousandths of an inch. In one exemplary configuration, the 30 thousandths diameter flexible member 14 can be used, for example, where construct 10 is routed or passed through holes drilled in the bone so that flexible member 14 can be more easily manipulated during such routing. The larger 37-40 thousandths diameter flexible member 14 can be used, for example, where the construct 10 is wrapped around the sternum, as will be discussed herein. Forming the construct 10, as well as other constructs discussed herein, with a larger diameter flexible member provides more surface area of the tensioned flexible member to engage the sternum or other bone, and thus distribute the compressive load over a greater area of the bone.

Figure 3:
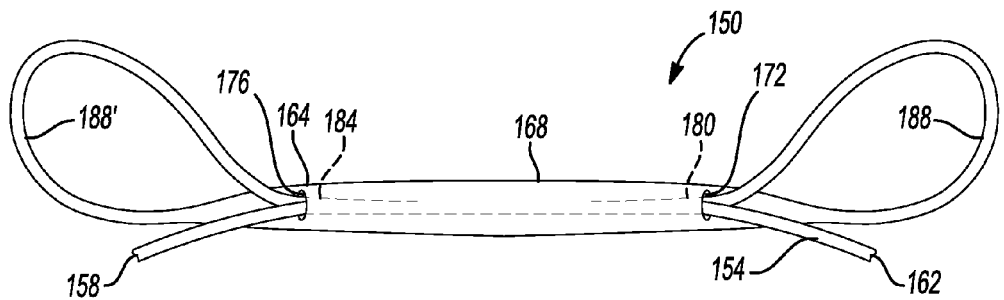
FIGS. 3, 3A and 3B depict alternative flexible member constructs according to the present teachings.
Figure 3A:
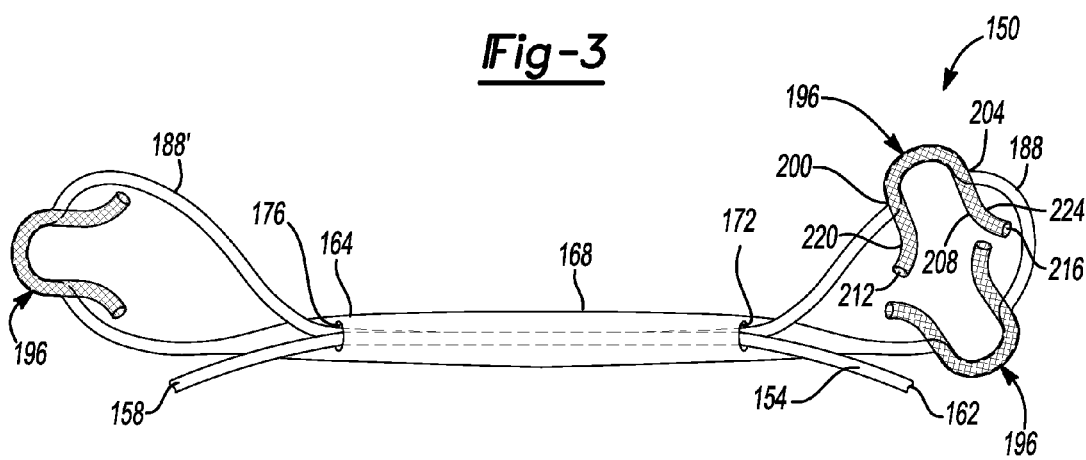

With additional reference to FIG. 3, and FIG. 3A, an exemplary alternative adjustable flexible member construct 150 is shown. Construct 150 can include a hollow flexible member 154 having a first end 158 and a second end 162, and can include a body 164 that defines a longitudinal passage portion 168 therein between first and second ends 158, 162, as shown in FIG. 3. The passage portion 168 can define a pair of apertures 172, 176 at opposed ends thereof, similar to apertures 38, 46 discussed above. To form construct 150, the first end 158 can be passed through aperture 172 and passage portion 168 and out aperture 176 such that a portion 180 of flexible member 154 following first end 158 extends through passage portion 168. In a similar manner, second end 162 can be passed through aperture 176 and passage portion 168 and out aperture 172 such that a portion 184 of flexible member 154 following second end 162 also extends through passage portion 168. This configuration forms two loops 188 and 188', as shown in FIG. 3. It should be appreciated that each of the first and second ends 158, 162 can alternatively be pushed through a respective space defined between adjacent individual fibers of the braided flexible member 14 such that the respective spaces defined between fibers comprise apertures 172, 176 in communication with an interior longitudinal passage.

The pulling of ends 158, 162 can cause movement of portions 180, 184 relative to passage portion 168, and the loops 188, 188' can be reduced to a desired size or placed in a desired tension. Tension in loops 188, 188' can cause the body 164 defining the passage portion 168 to be placed in tension and therefore cause passage portion 168 to constrict about portions 180, 184 passed therethrough. This constriction reduces the diameter of passage portion 168, thus forming a mechanical interface between the exterior surfaces of portions 180, 184 and an interior surface of passage portion 168. This constriction results in static friction between the interior and exterior surfaces at the mechanical interface, causing the adjustable flexible member 154 to "automatically" lock in a reduced size or diameter configuration in which tension is maintained. Flexible member construct 150 with adjustable loops 188, 188' can be used to compress a fractured or sectioned bone, such as a sectioned sternum in a sternal closure procedure following open chest surgery, as will be discussed herein.

With additional reference to FIG. 3A, adjustable flexible member construct 150 is shown having attachment members or flexible anchors 196 coupled to loops 188, 188'. Each loop can include various numbers of anchors coupled thereto, including more or fewer anchors 196 than shown. Each anchor 196 can define a hollow core and can include a pair of apertures 200, 204 formed in a body 208 thereof in a similar manner as apertures 38, 46 discussed above. Flexible member 154 can pass through first aperture 204 into the hollow core and out through the second aperture 200, as shown in FIG. 3A. Apertures 200, 204 can be placed inward from respective ends 212, 216 of anchors 196 so as to form tail portions 220, 224 adjacent each aperture 200, 204. The tail portions 220, 224 can provide anchoring resistance relative to a corresponding bone or anchoring structure, as will discussed herein.

Figure 3B:
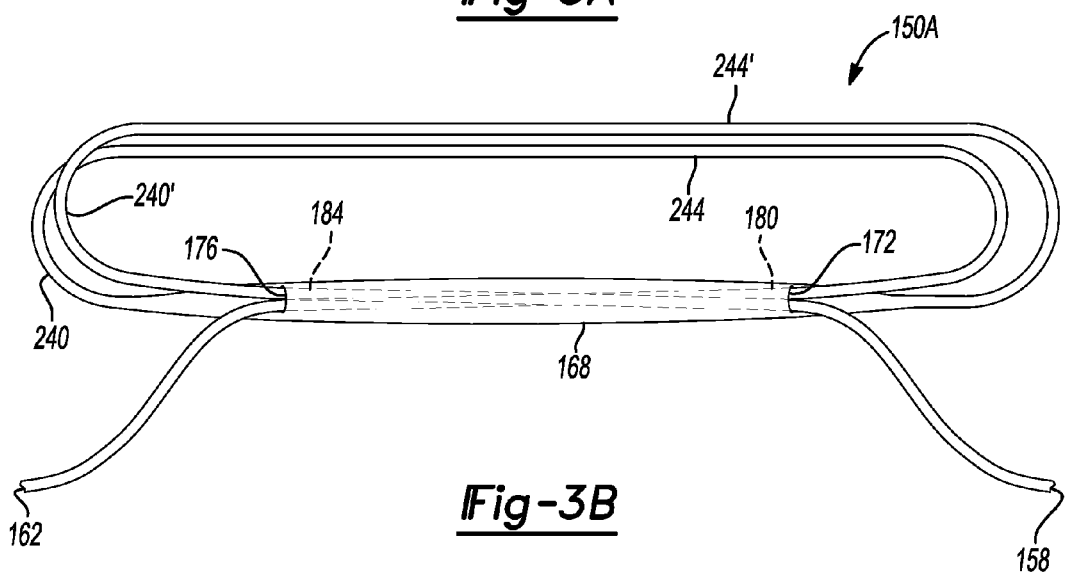

With reference to FIG. 3B and continuing reference to FIGS. 3 and 3A, an alternative adjustable flexible member construct 150A is shown. Construct 150A can be formed to include a double loop configuration having two loops 240, 240' that each traverse a path from one end of passage portion 168 to the other end thereof, instead of each loop being disposed at respective opposite ends of passage portion 168 as in construct 150. Flexible member construct 150A can be formed by passing the first end 158 of the flexible member through aperture 176, through passage portion 168 and out aperture 172. The second end 162 can be passed through aperture 172, through the passage portion 168 and out the aperture 176. In various aspects, the first and second apertures 172, 176 can be formed during the braiding process as loose portions between pairs of fibers defining the flexible member 154, as discussed above. Passing ends 158, 162 through the apertures 172, 176 can form the loops 240, 240'. The loops 240, 240' can define mount or summit portions 244, 244' of the adjustable flexible member construct 150A and can be disposed generally opposite from the passage portion 168. Flexible member construct 150A can be used, for example, to compress a fractured or sectioned bone or to close a sectioned sternum in sternal closure procedures, as will be discussed herein.

The longitudinal and parallel placement of the first and second ends 158 and 162 of the flexible member 154 within the passage portion 168 resists the reverse relative movement of the first and second portions 180, 184 of the flexible member construct 150A once it is tightened. The tensioning of the ends 158 and 162 can cause relative translation of the portions 180, 184 relative to passage portion 168. Upon applying tension to the first and second ends 158 and 162, the loops 240, 240' can be reduced to a desired size or placed in a desired tension. Tension in the loops 240, 240' can cause the body of the flexible member 154 defining the passage portion 168 to be placed in tension and therefore cause passage portion 168 to constrict about the portions 180, 184 similarly to the constriction discussed above with respect to construct 150. This constriction can cause the adjustable flexible member construct 150A to "automatically" lock in a reduced size or smaller diameter configuration. A further discussion of the flexible member constructs 150, 150A are provided in U.S. patent Ser. No. 11/541,506 filed on Sep. 29, 2006 entitled "Method and Apparatus for Forming a Self-Locking Adjustable Suture Loop" assigned to Biomet Sports Medicine, LLC, and the disclosure is incorporated by reference.

Referring now to FIGS. 4-16, the use of flexible member constructs 10, 150 and 150A in various assembly configurations and exemplary sternal closure procedures will now be described. With particular reference to FIGS. 4 and 5, a sternum 304 is shown having a section or cut 308 separating sternal portions 312, 316, such as may be performed in connection with cardiac surgery. Flexible member constructs 10, 150, 150A alone, or in various combinations with each other or additional fixation devices, can be used to compress and secure sternal portions 312, 316 together to assist healing, as will be discussed herein.

Figure 4:
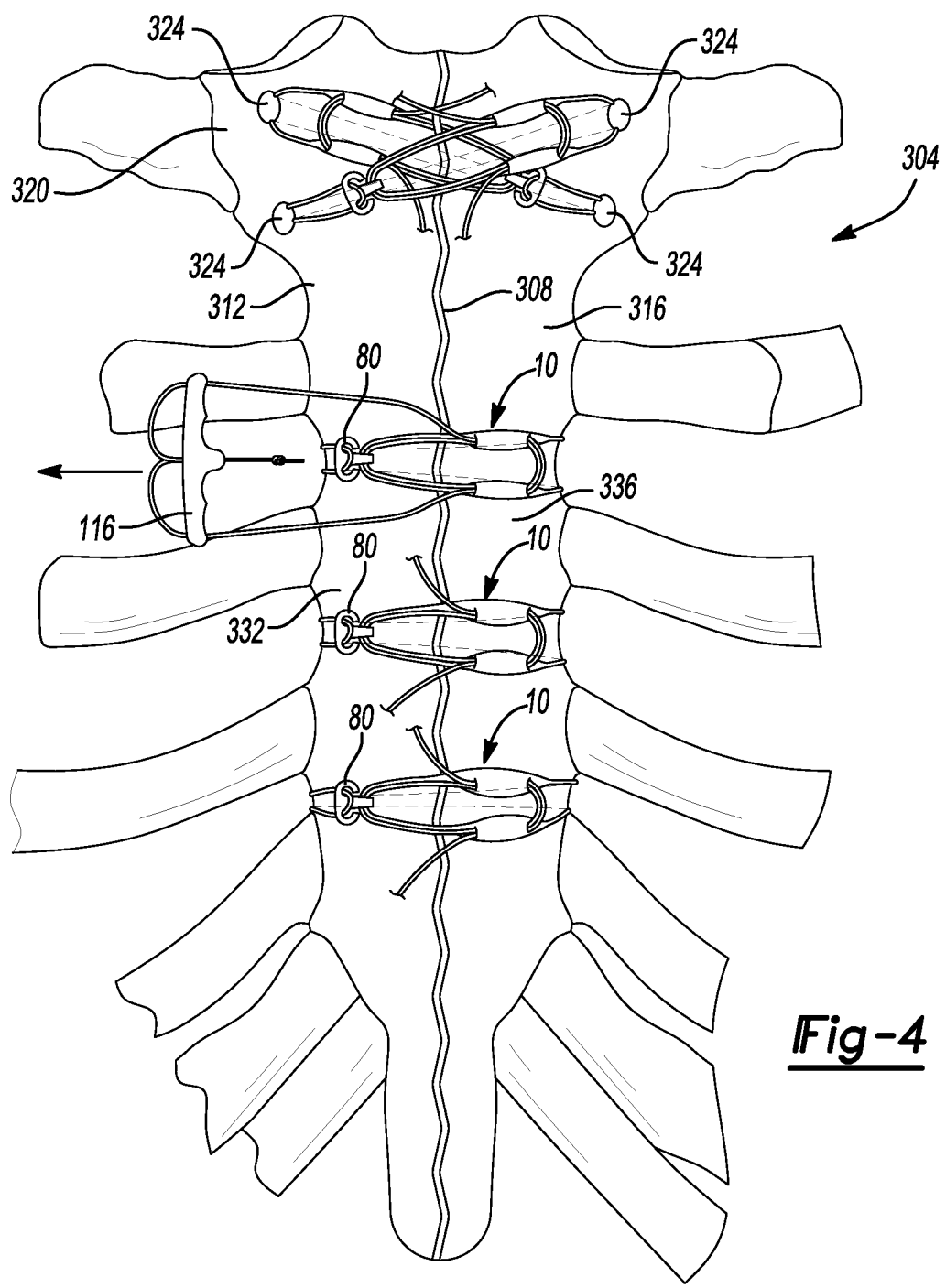
FIGS. 4 and 5 depict exemplary views of the adjustable flexible member construct of FIG. 1 in a surgical procedure for sternal closure according to the present teachings.
Figure 5:
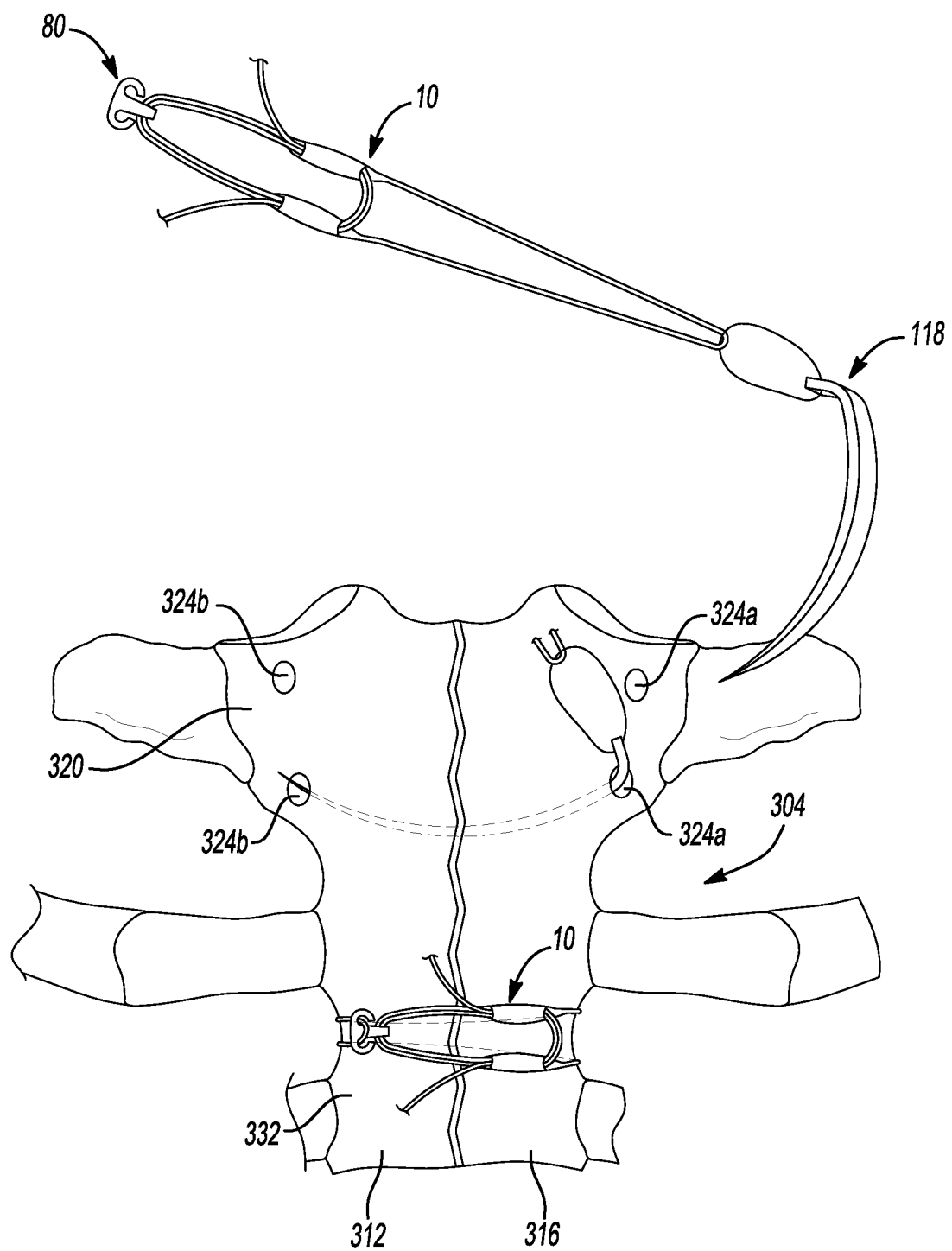

In FIGS. 4 and 5, adjustable flexible member construct 10 is shown in various configurations to compress sternal portions 312, 316 toward each other to close section 308. In one exemplary configuration, two flexible member constructs 10 can be used in a diagonal pattern in the manubrium 320 of the sternum in connection with two pairs of diagonally opposite holes 324 formed in the manubrium 320. While the diagonal pattern of flexible member construct 10 is shown in the manubrium 320 in FIG. 4, a non-diagonal or medial-lateral configuration can alternatively be used, as generally shown in FIG. 5.

To secure flexible member construct 10 to the manubrium 320, passing member 118 can be inserted through a first hole 324a of a respective pair of holes 324a, 324b and directed towards a corresponding second hole 324b, as shown in FIG. 5. A surgeon or the like can pull the passing member through the second hole 324b thus routing at least the fixed portion 34 through the first and second holes 324a, 324b. Fixed portion 34 can then be secured to attachment member 80, as shown in FIG. 4. Once fixed portion 34 is secured to the attachment member, first and second ends 18, 26 can be pulled or tensioned to reduce the loops 66, 70 to a desired size and to place construct 10 in a desired tension to compress and close the sectioned sternum 304. Ends 18, 26 of construct 10 can be tensioned by pulling on the respective ends as discussed above, or with the use of the handle 116, as generally shown in FIG. 4. Handle 116 can provide the surgeon with an ability to easily tension ends 18, 26 simultaneously and evenly. Handle 116 can then be removed and discarded. Handle 116 can be used to evenly tension loops 66, 70 as discussed above, or can be used to tension loops 66, 70 at different rates by manipulating an angle of handle 116 so that, for example, a first loop of loops 66, 70 can be tensioned at a faster rate than a second loop of loops 66, 70. In this manner, the first loop can reach a desired final tension before the second loop. In one exemplary configuration, the smaller diameter flexible member can be used with construct 10 in manubrium 320 for easier manipulation through holes 324.

Flexible member construct 10 can also be used to compress a body 332 of sternum 304, as also shown in FIGS. 4 and 5. For the body 332, construct 10 can be wrapped around the sternum and fixed portion 34 can be secured to attachment member 80 such that ends 18, 26 extend from an anterior side 336 of body 332, as shown in FIG. 4. In the exemplary configuration shown in FIG. 4, three flexible member constructs 10 are shown securing the body 332 of the sternum 304. Nevertheless, more or fewer flexible constructs than shown can be used in the intercostal spaces between the ribs to secure the body of the sternum, as may be determined by a surgeon during a sternal closure procedure. In addition, the larger diameter flexible member construct 10 can be utilized in body area 332 of sternum 304, according to one exemplary configuration. The larger diameter flexible member can enable more tension to be applied to the bone or sternum without cutting into or damaging the bone.

The flexible member constructs 10 can be attached and tensioned or secured to the sternum 304 in various orders. For example, flexible member constructs 10 can first be attached to the manubrium 320 and then to the body 332, or vice-versa. Additionally, flexible member constructs 10 can be tensioned in various orders, such as initially tensioning each flexible member construct 10 to a snug or non-slack condition and then further tensioning each construct 10 to a final desired tension. As discussed above, constructs 10 can be tightened with or without use of handle 116. Flexible construct 10 can automatically lock under tension, as also discussed above, after which a portion of ends 18, 26 can be trimmed and removed.

Flexible member construct 10 also can be provided with an antibiotic and/or platelet concentrate coating to resist bacterial adhesion and/or promote healing. In this regard, flexible member construct 10, as well as other constructs discussed herein, can be pre-configured with such a coating or the coating can be applied intraoperatively. Further, the surgeon can also apply the platelet coating to the sectioned area during the sternal closure procedure.

Figure 6:
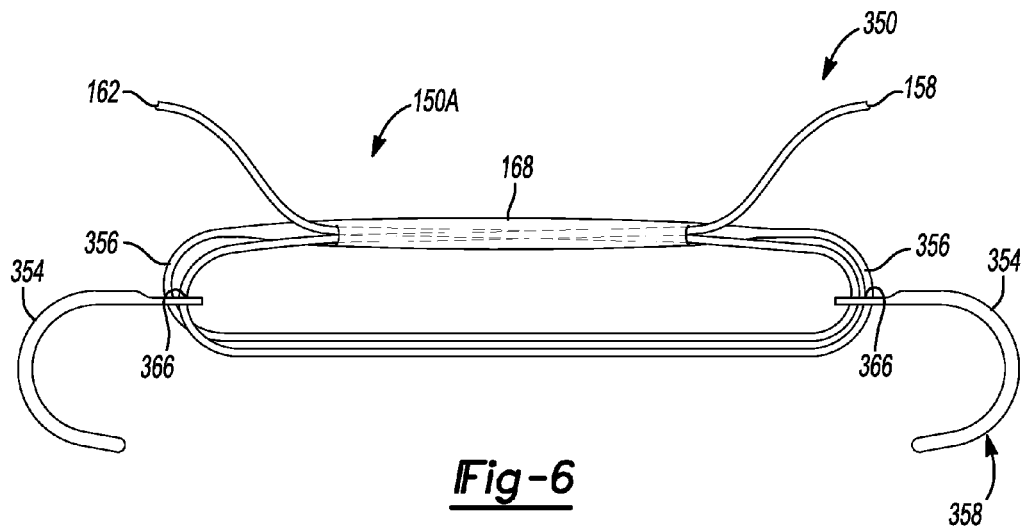
FIGS. 6-9 depict views of exemplary alternative attachment members associated with one or more of the adjustable flexible member constructs according to the present teachings.
Figure 10:
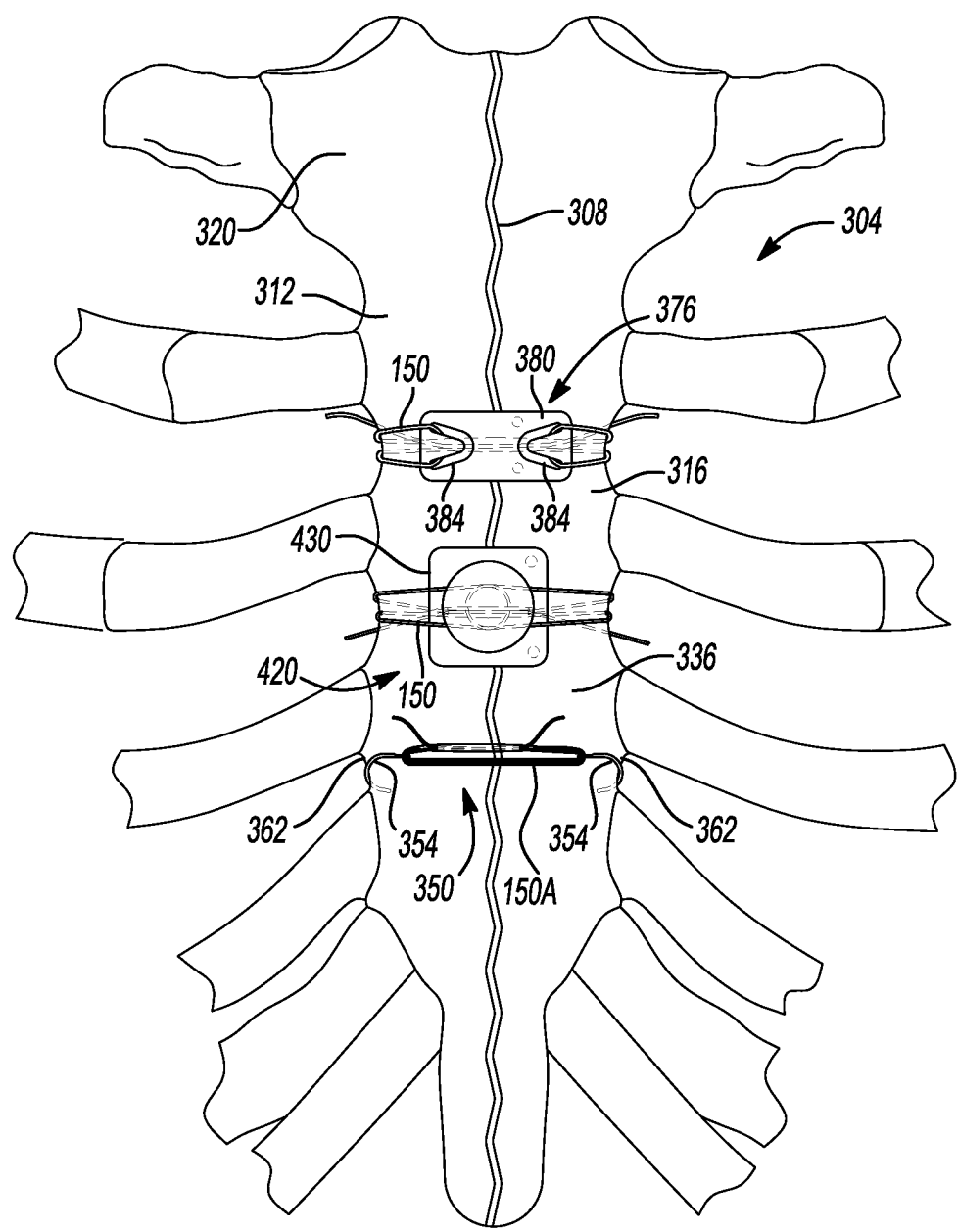
FIGS. 10 and 11 depict views of the attachment members of FIGS. 6-9 in exemplary configurations for use in a sternal closure procedure according to the present teachings.

With additional reference to FIGS. 6 and 10, flexible member construct 150A is shown in an assembly configuration 350 having a pair of attachment members 354 coupled to opposed sides 356 of loops 240 and 240'. Attachment members 354 can include a generally arcuate shape 358 and, in the exemplary configuration shown in FIG. 6, a generally semi-circular shape or U-shape. The shape 358 of attachment members 354 can be used to secure the attachment members 354 to medial and lateral sides 362 of sternum 304, as generally shown in FIG. 10. Attachment members 354 can include an aperture 366 for receiving loops 240, 240' therethrough, as shown in FIG. 6. In an exemplary configuration, flexible member construct 150A can be formed integrally with attachment members 354 for use in a sternal closure or other fracture reduction procedure. In this manner, attachment members 354 can be preformed and coupled to loops 240, 240' to form assembly configuration 350, which can be provided in the assembly configuration for use in the sternal closure procedure.

With particular reference to FIG. 10, construct 150A in the assembly configuration 350 can be used to compress the sternum 304 by securing attachment members 354 to the sides 362 of sternal portions 312, 316 and then applying tension to ends 158, 162 of construct 150A. The adjustable loops of construct 150A can then be reduced to the desired size and placed in the desired tension to compress sternum 304 about section 308. Flexible member construct 150A can automatically lock under tension to maintain the reduced size of loops 240, 240', as discussed above. It should be appreciated that while attachment members 354 are described above in connection with flexible member construct 150A, the attachment members 354 can also be used with alternative flexible member constructs, such as construct 150.

Figure 7:
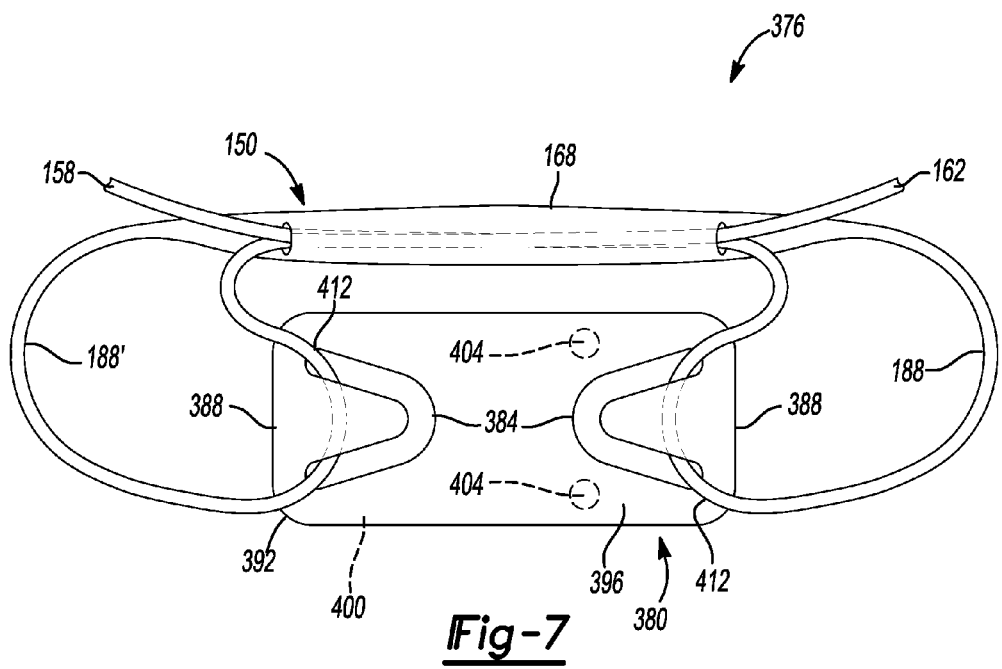

Turning now to FIG. 7 and with reference to FIG. 10, flexible member construct 150 is shown in an assembly configuration 376 operatively associated with an attachment member or frame 380. Frame 380 can be used to facilitate securing flexible member construct 150 around a fractured bone or the sectioned sternum 304 to compress the fracture or section and affect healing. Frame 380 can include a pair of attachment portions 384 at opposed ends 388 of the frame. In the exemplary configuration shown, frame 380 can include a generally rectangular plate 392 and the attachment portions 384 can be in the form of V-shaped apertures extending through plate 392 from a top surface 396 to a bottom surface 400, as shown in FIG. 7. Bottom surface 400 can optionally include a pair of fixation members 404 to prevent movement of frame 380 relative to the sternum 304 upon placement thereon. Fixation members 404 can include spikes, posts, screws, adhesive or the like that are coupled to or pass through or extend from the bottom surface 400.

With additional reference to FIG. 10, flexible member construct 150 in the assembly configuration 376 is shown with the bottom surface of frame 380 positioned on the anterior side 336 of sternum 304. Flexible member construct 150 can then be wrapped around sternum 304 and opposed ends 412 of loops 188, 188' can be secured to frame 380 via attachment portions 384. In this configuration, passage portion 168 can be positioned on a posterior side of sternum 304, as generally shown in FIG. 10. Ends 158, 162 of construct 150 can then be tensioned to reduce the loops 188, 188' to the desired size and tension to compress and close section 308 and assist healing of sternum 304. Flexible member construct 150 can automatically lock and maintain the reduced size of loops 188, 188' under tension, as discussed above. It should be appreciated that frame 80 can also be used with flexible member construct 10.

Figure 8:
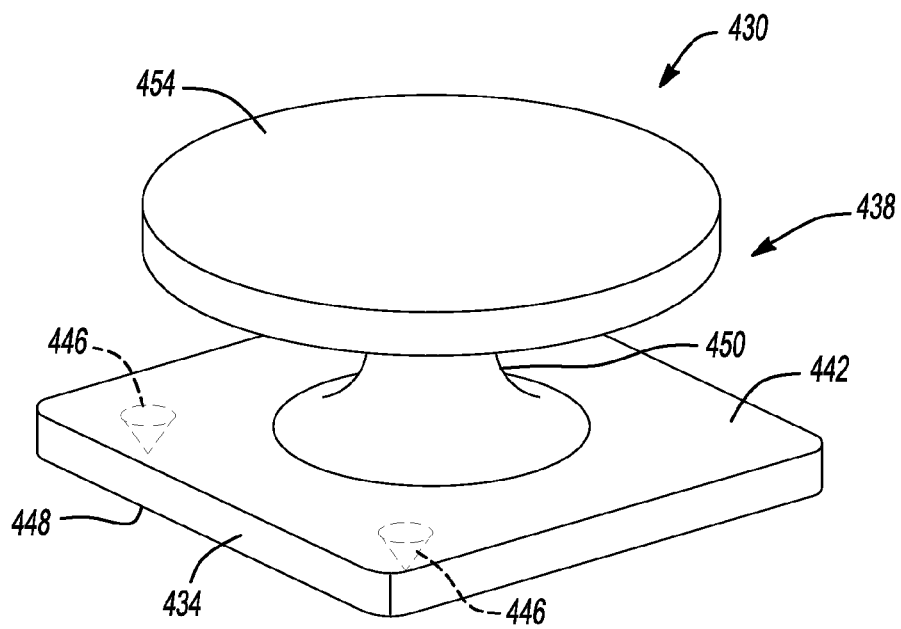

Referring now to FIGS. 8 and 10, flexible member construct 150 is shown in an assembly configuration 420 operatively associated with an attachment member or frame 430. Frame 430 can include a base 434, a post 438 extending from an upper surface 442 of base 434, and at least one optional fixation member 446 extending from a lower surface 448 of base 434. Fixation member 446 can include spikes, posts, screws, adhesive or the like that are coupled to or extend from lower surface 448. Post 438 can include a reduced diameter neck portion 450 coupled to the base and a larger diameter or head portion 454 coupled to the neck portion 450 and configured to retain loops 188, 188' of construct 150, as discussed below. Frame 430 can be placed on sternum 304 with lower surface 448 engaging the anterior side 336 of sternum 304, as shown in FIG. 10. Flexible member construct 150 can be wrapped around sternum 304 in one of the intercostal spaces and each loop 188, 188' can be secured to the frame 380 via post 438, as also shown in FIG. 10.

In this exemplary configuration, passage portion 168 can be positioned on the posterior side of sternum 304. Once frame 430 is positioned and construct 150 is wrapped around the sternum and secured to post 438, ends 158 and 162 extending from the posterior side of sternum 304 can be tensioned. Applying tension to ends 158, 162 can reduce loops 188, 188' to a desired size and tension to compress sectioned sternal portions 312, 316 together to assist healing at section 308, as generally shown in FIG. 10. Flexible construct 150 can automatically lock loops 188, 188' under tension to maintain the reduced size of loops 188, 188' and compression of sternal portions 312, 316 together, as discussed above.

It should be appreciated that while reference to FIG. 10 has been made with respect to the assembly configurations 350, 376 and 420, these assembly configurations have been combined in one figure for illustration purposes only and need not be used together. In this regard, an exemplary sternal closure procedure could utilize only one of the assemblies shown in the intercostal spaces, or combinations thereof, as may be desired by a particular surgeon performing a sternal closure procedure. It should also be appreciated that assemblies 350, 376 and 420 could be used individually or in various combinations with flexible member constructs 10 secured to the manubrium 320, as discussed above with reference to FIG. 4.

Figure 9:
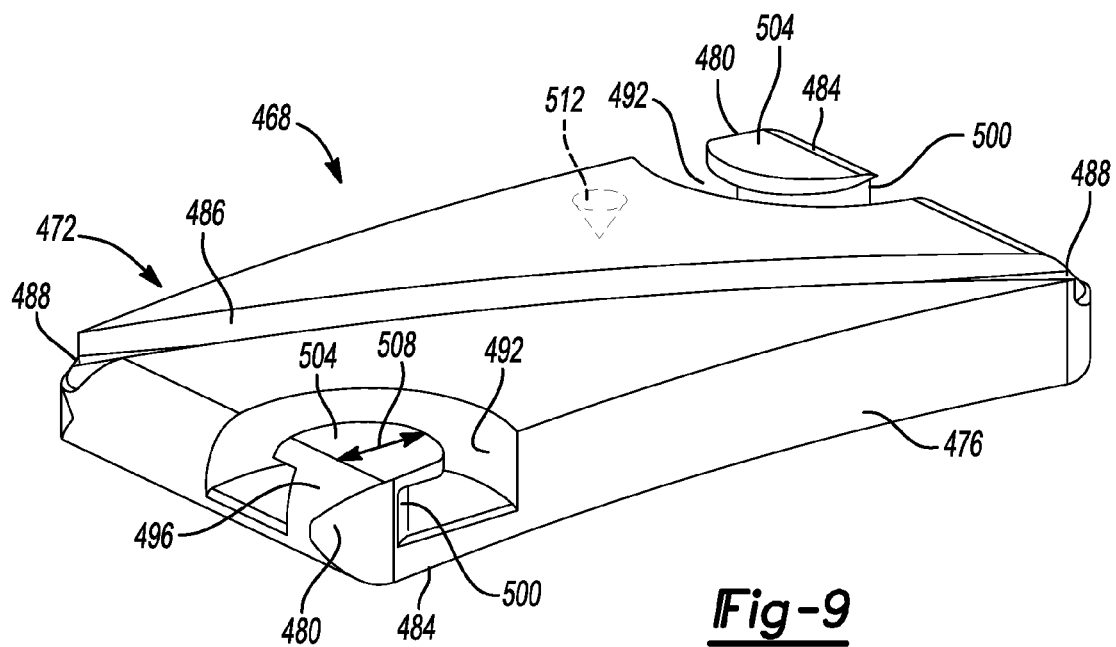
Figure 11:
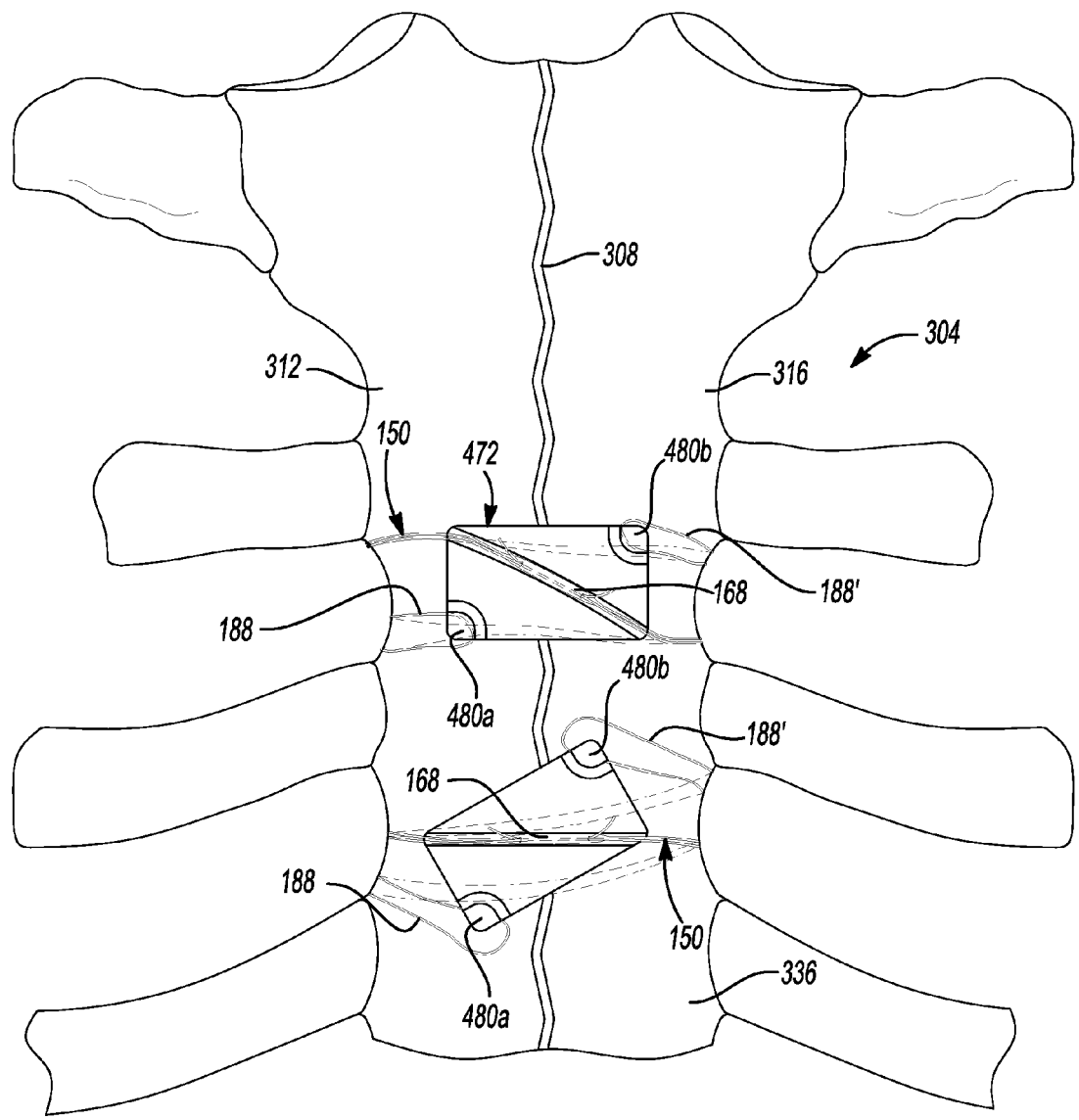

Referring now to FIGS. 9 and 11, adjustable flexible member construct 150 is shown in an assembly configuration 468 operatively associated with a frame 472. As shown in FIG. 9, frame 472 can include a generally rectangular body 476 with attachment portions 480 positioned at one pair of diagonally opposed corners 484 and a groove or channel 486 extending diagonally across a top surface of frame 472 from a second pair of opposed corners 488. While frame 472 is shown having rectangular body 476, it should be appreciated that frame 472 can be configured in other shapes, such as various polygonal shapes for use in coupling frame 472 to flexible member construct 150, as will be described below. Attachment portions 480 can each include a recess 492 at least partially surrounding a post 496. Post 496 can include a neck portion 500 and a cap or head portion 504 having a width dimension 508 greater than a corresponding width of neck portion 500 such that at least a portion of head portion 504 overhangs neck portion 500, as shown in FIG. 9. At least one optional fixation member 512 can extend from a bottom surface 516 of frame 472.

With particular reference to FIG. 11, frame 472 can be positioned in various configurations relative to sternum 304, as illustrated by the two exemplary configurations shown in FIG. 11. Frame 472 can be positioned on sternum 304 such that the bottom surface 516 engages the anterior side 336 of sternum 304. Flexible member construct 150 can be wrapped around sternum 304 within an intercostal space thereof and loops 188, 188' can be coupled to respective attachment portions 480. More specifically, flexible construct 150 can be placed in channel 486 such that passage portion 168 is positioned within channel 486, as shown in FIG. 11. Positioning construct 150 in channel 486 can provide a low profile closure arrangement that can be more conformable or provide less discomfort to a recipient patient. Loop portion 188 can then be wrapped around the posterior side of sternum 304 in one direction and coupled to attachment portion 480A of the pair of attachment portions 480. Similarly, loop portion 188' can be wrapped around the posterior side of sternum 304 in an opposite direction of loop 188 and then be coupled to attachment portion 480B. Tension can then be applied to ends 158, 162 to reduce the size of loops 188, 188' to compress sternal portions 312, 316 together to assist healing of sectioned sternum 304 at section 308. Flexible member construct 150 can automatically lock loops 188, 188' at the desired reduced size under tension, as discussed above. In addition, placing frame 472 over the section can also stabilize the sternum to align sternal portions 312, 316 to be co-planar.

Flexible member construct 150 in the assembly configuration 468 can be used alone or in various combinations with flexible member constructs 10 and 150A and/or assembly configurations 350, 376 and 420 discussed above. For example, flexible member constructs 10 can be used in the manubrium 320 as shown in FIG. 4 and assembly 468 can be used alone or in various combinations with assemblies 350, 376 and 420 in the body 332 to compress sternal portions 312, 316, as discussed above.

Figure 12:
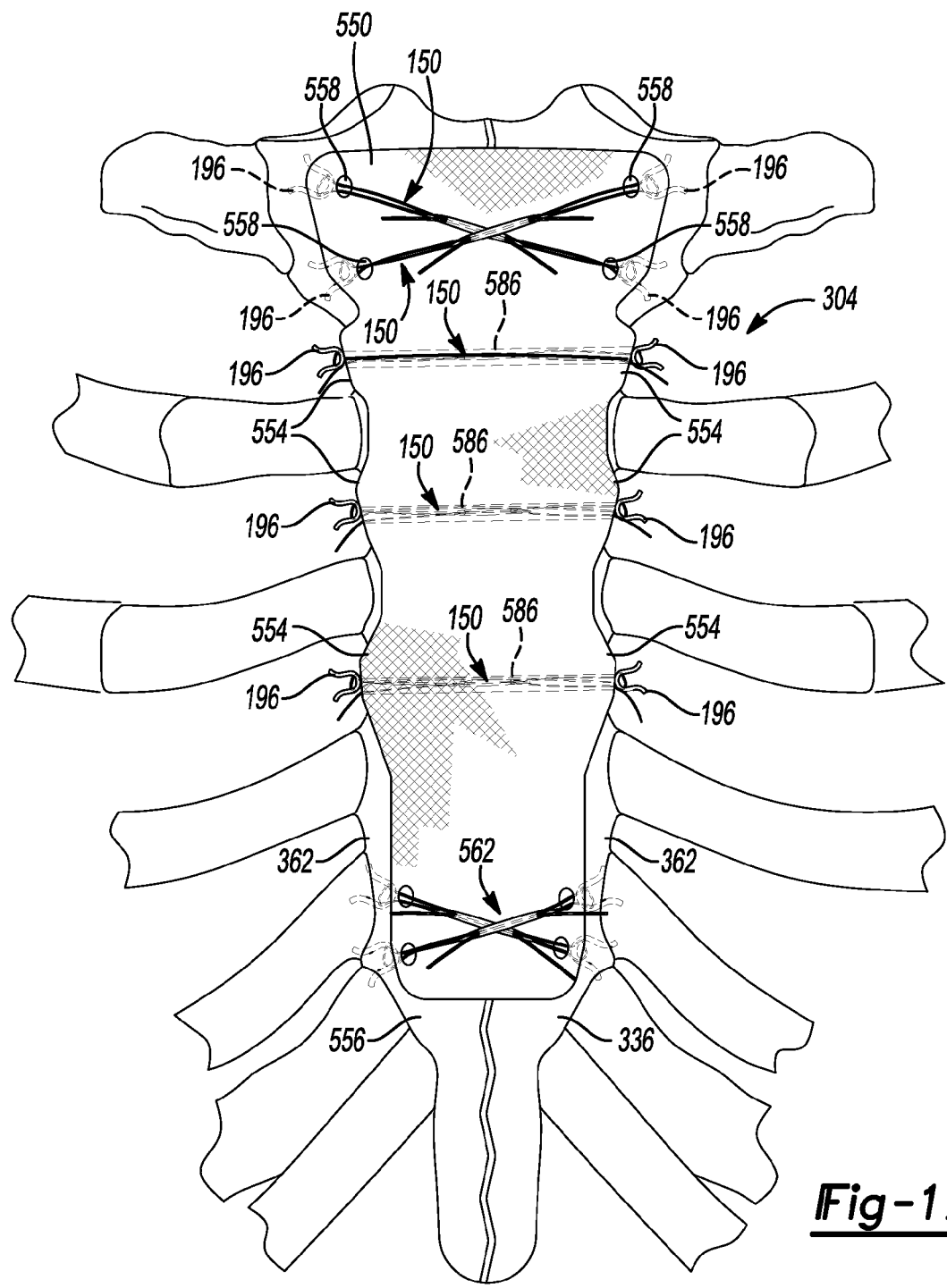
FIG. 12 depicts a view of an exemplary use of the flexible member construct of FIG. 3A in a surgical method for sternal closure according to the present teachings.

Referring now to FIG. 12, adjustable flexible member construct 150 is shown operatively associated with anchors 196 and an orthopedic mesh 550 for use in a sternal closure procedure. More particularly, orthopedic mesh 550 can be positioned on the anterior side 336 of sternum 304 such that portions 554 extend around the lateral sides 362 in the intercostal spaces, as shown in FIG. 12. The orthopedic mesh 550 can be, for example, a product sold by Biomet Sports Medicine, LLC under the name SportMesh™. With the orthopedic mesh 550 positioned on sternum 304 as discussed above, construct 150 with anchors 196 can be used in various configurations to compress the sectioned sternum 304 at section 308, as generally shown in FIG. 12.

The orthopedic mesh 550 can be coated with the platelet concentrate discussed above, and/or antibiotics, bone growth agents, etc. to aid in soft tissue healing. The mesh 550 can provide a barrier between the flexible member constructs and the bone to aid in transferring load from the flexible member construct to the mesh 550, which can decrease the pressure applied to the bone by the tensioned flexible member construct. The mesh 550 can be particularly useful, for example, in patients with soft bone tissue. It should also be appreciated that load distribution in the intercostal spaces can be provided by the portions 554 that extend around the medial and lateral sides. Moreover, the orthopedic mesh can aid in the retention of anchors 196, particularly where the bone tissue may be soft.

In one exemplary configuration, four holes 558 can be formed through the mesh 550 and the manubrium 320. Flexible anchors 196 associated with two flexible member constructs 150 can be inserted through respective diagonal pairs of holes 558 through the manubrium, as shown in FIG. 12. The constructs 150 can be in diagonal overlapping pattern and be disposed primarily on top of the orthopedic mesh 550. Upon tensioning the free ends 158, 162 of each construct 150, the tail portions 220, 224 of anchors 196 can engage the posterior manubrium adjacent holes 558 and provide anchoring resistance to retain the anchors 196 outside of holes 558 on the posterior side of the sternum 304. The loops 188, 188' subsequently can be reduced to the desired size or tension to compress sternal portions 312, 316 and assist closure and healing of the sectioned sternum. The orthopedic mesh 550 can work to distribute the load placed on the anterior side 336 of the sternum by the constructs 150 under tension. A similar configuration 562 can be used at a lower portion 566 of the sternum 304 adjacent the Xiphoid process, as also shown in FIG. 12. It should be appreciated that configuration 562, as well as the configuration discussed immediately above with respect to the manubrium, can alternatively be in a parallel transverse pattern as opposed to the illustrated diagonal patterns.

Continuing with FIG. 12, adjustable flexible construct 150 having a pair of anchors 196 attached to respective loops 188, 188' can be inserted through transverse bores 586 formed in sternum 304. In particular, the constructs 150 can be positioned in bores 586 such that the passage portions 168 are each aligned in a respective bore 586, as shown in FIG. 12. The constructs 150 can be pierced or routed through the portions 554 of orthopedic mesh 550 that extend around the lateral sides of sternum 304 so as to provide additional anchoring resistance and load distribution for flexible anchors 196, as shown in FIG. 12. Ends 158, 162 can be tensioned to compress sternal portions 312, 316, as discussed herein. It should be appreciated that while orthopedic mesh 550 is shown in FIG. 12 with reference to construct 150 and flexible anchors 196, orthopedic mesh 550 can be used in various other sternal closure configurations disclosed herein, for example, to distribute a load applied by the various disclosed flexible member constructs relative to the sternum 304.

Figure 13:
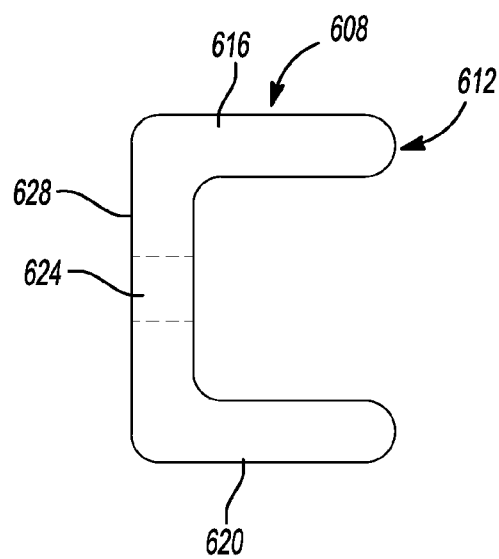
FIG. 13 depicts an exemplary alternative attachment member according to the present teachings.
Figure 14:
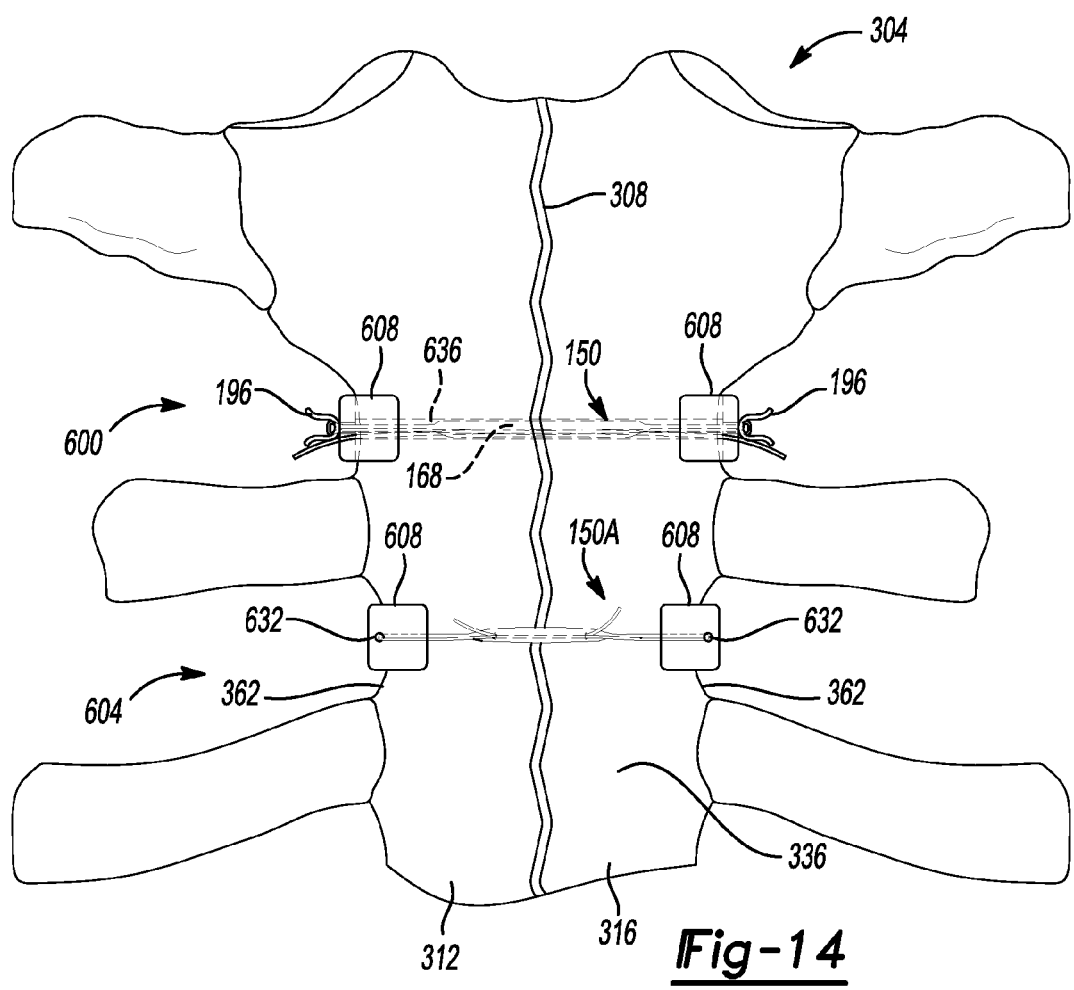
FIG. 14 depicts exemplary configurations of the attachment member of FIG. 13 associated with various adjustable flexible member constructs according to the present teachings.

Referring now to FIGS. 13 and 14, adjustable flexible member construct 150 is shown in exemplary assembly configurations 600 and 604 operatively associated with attachment members 608. Each attachment member 608 can include a body 612 having a substantially U-shaped configuration and can be sized for positioning about the lateral sides 362 of sternum 304 such that top and bottom portions 616, 620 extend about the respective anterior and posterior sides of the sternum, as shown in FIG. 14. In one exemplary configuration, attachment member 608 can include an aperture 624 positioned within a side portion 628 connecting the top and bottom portions 616, 620. In another configuration, attachment member 608 can include an aperture 632 in the top portion 616, as shown in FIG. 14. Aperture 632 can be in lieu of or in addition to aperture 624.

With reference to assembly configuration 600, flexible member construct 150 with anchors 196 can be positioned through transverse bore 636 in sternum 304 such that passage portion 168 is positioned within the bore. Each respective loop 188, 188' with anchors 196 can be passed through aperture 624 in attachment member 608 such that the anchors 196 are on a first side of portion 628 opposite a second side adjacent the sternum 304. Ends 158, 162 can then be tensioned thereby reducing a size of loops 188, 188' so as to draw attachment members 608 against the lateral sides of sternum 304 and compress sternal portions 312, 316 together. Flexible member construct 150 can automatically lock the loops in the reduced diameter configuration under tension, as described herein. Attachment members 608 can facilitate distributing a compression load applied to the sternum by the tensioned construct 150, which can enable more tension to be applied.

With continuing reference to FIG. 14, assembly configuration 604 can include attachment members 608 integrally formed or pre-assembled with flexible member construct 150A such that loops 240, 240' are coupled to apertures 632. In this configuration, attachment members 608 can be positioned against the respective lateral sides of sternum 304, similar to assembly configuration 600 discussed above. Flexible member construct 150A can be positioned relative to the anterior side 336 of sternum 304 such that it does not wrap around or extend through sternum 304. It should be appreciated that assembly configurations 600, 604 can be used alone or with various other flexible member construct and assembly configurations disclosed herein to compress sternal portions 312, 316 to assist healing of sectioned sternum 304.

Figure 15:
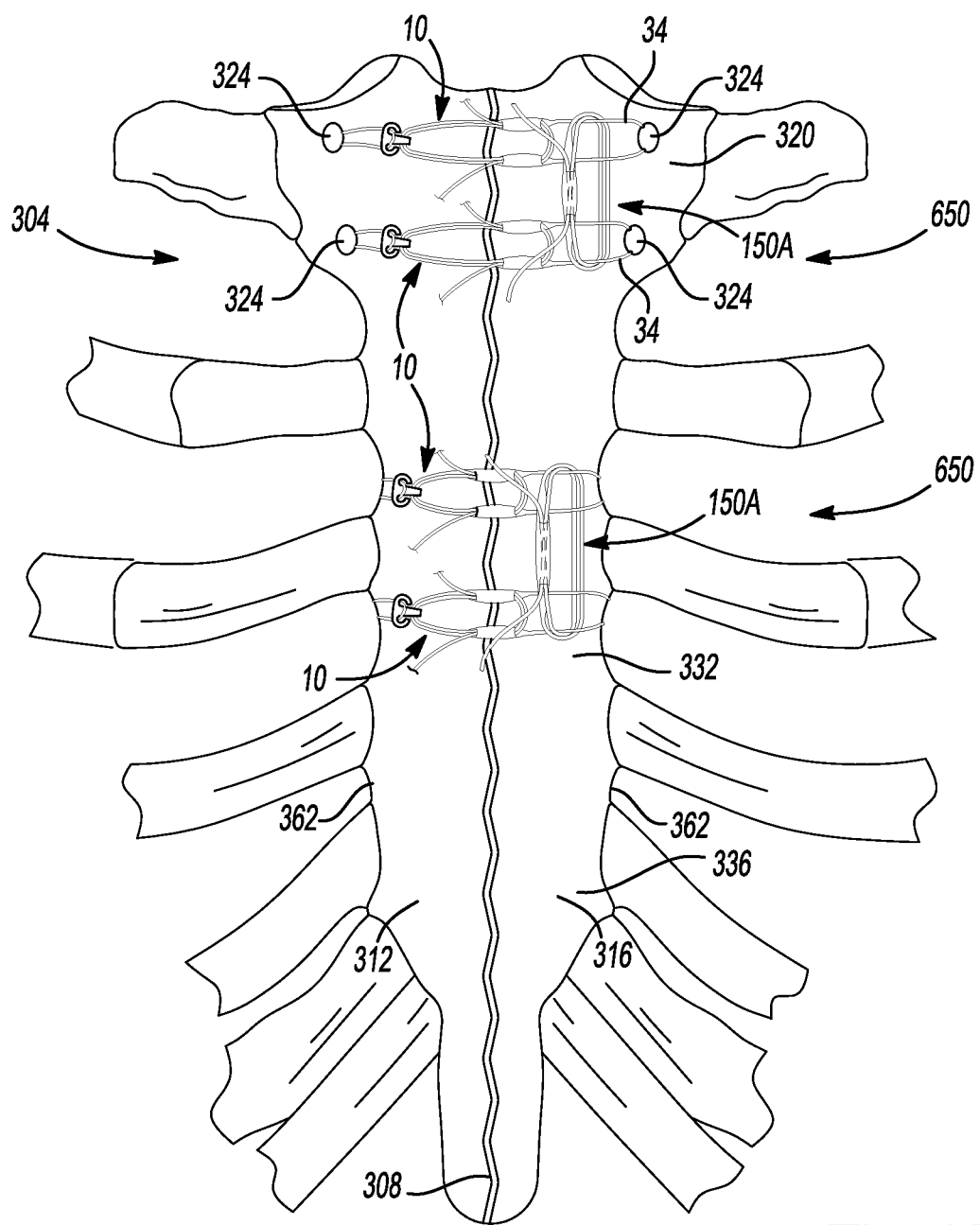
FIG. 15 depicts an exemplary surgical method for sternal closure according to the present teachings.

Turning now to FIG. 15, an alternative configuration 650 for compression of sternum 304 in a sternal closure procedure is provided. Configuration 650 can include two flexible member constructs 10 in a transverse orientation in the manubrium 320, as generally discussed above with reference to FIGS. 4 and 5. Configuration 650 can also include flexible member construct 150A coupled around the two constructs 10 before fixed portion 34 of each construct 10 is coupled to the respective attachment member 80, as shown in FIG. 15. Construct 150A can be positioned generally in a superior-inferior orientation perpendicular to the transverse orientation of constructs 10. Construct 150A can be tensioned after tensioning constructs 10 to draw any remaining tension from the system. In this configuration, constructs 10 can provide cross-tensioning generally perpendicular to section 308 and construct 150A can provide tensioning generally parallel to section 308. Configuration 650 can also be utilized to compress the body 332 of sternum 304, where constructs 10 are wrapped around the sternum 304 instead of through holes 324, as also shown in FIG. 15.

Figure 16:
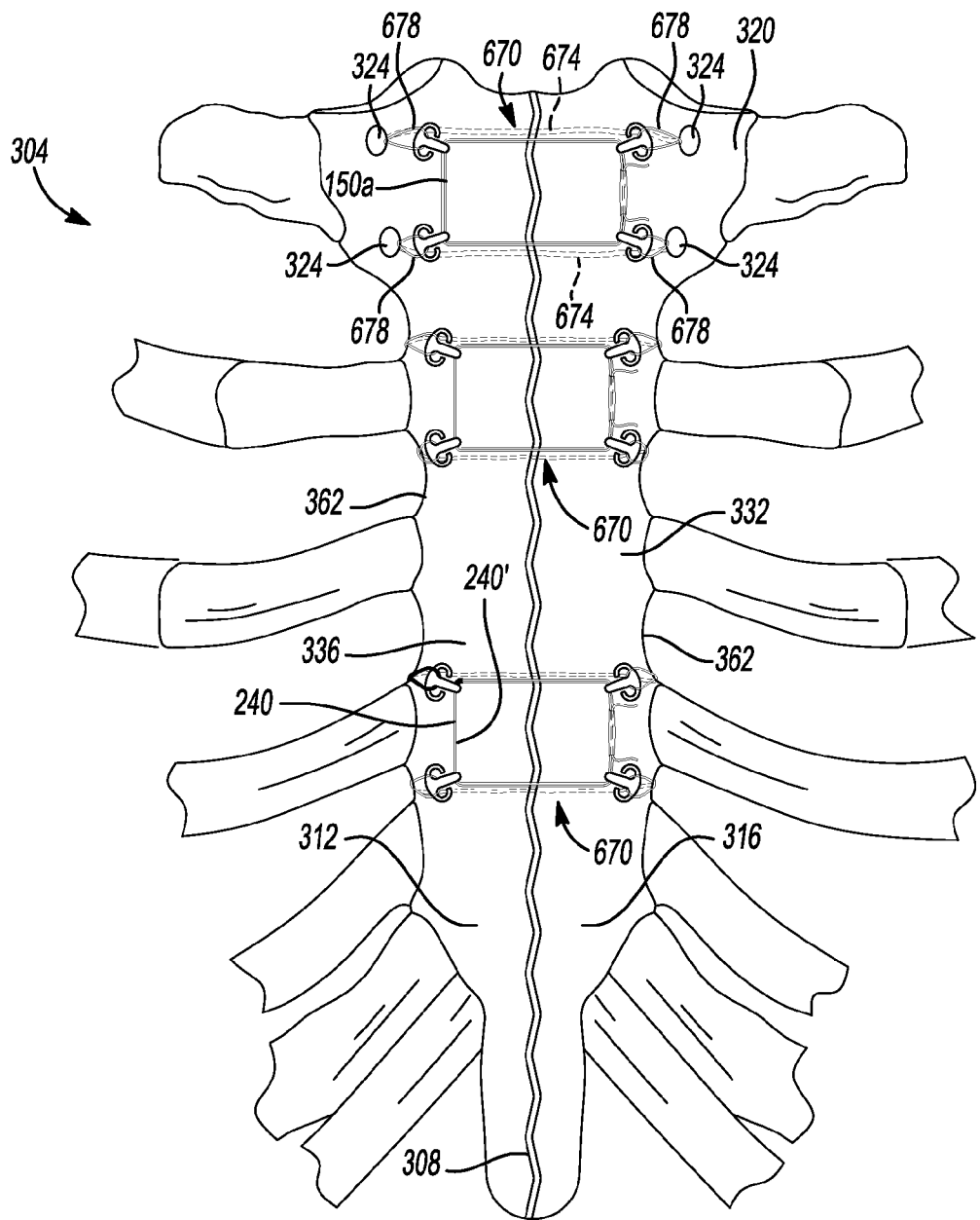
FIG. 16 depicts an exemplary surgical method for sternal closure according to the present teachings.

Referring now to FIG. 16, another alternative configuration 670 for compression of sternum 304 in a sternal closure procedure is provided. Configuration 670 can include two separate continuous suture or flexible member loops 674 having a fixed length. Alternatively, a flexible member construct, such as construct 150, can be used in place of fixed loops 674 to provide additional adjustment and tensioning capability. Flexible member construct 150A can be provided with four attachment members 80 integrally coupled to loops 240, 240'. In the manubrium area, loops 674 can be routed or passed along the posterior side of sternum 304 in a transverse orientation such that opposed ends 678 of loops 674 extend through a respective pair of holes 324, as shown in FIG. 16. The opposed ends 678 of each of loops 674 can be coupled to a respective two of the four attachment members 80. The ends 158, 162 of flexible member construct 150A can then be tensioned to compress sternal portions 312, 316, as discussed herein. Additional configurations 670 can be used to compress body 332 of sternum 304 where the fixed loops are wrapped around the sides of sternum 304 as opposed to being passed through holes 324, as also shown in FIG. 16. It should be appreciated that configurations 650 and 670 can be used alone or with various combinations of the flexible member constructs and assembly configurations discussed herein.

Turning now to FIGS. 17-28, various frames or tensioning members are shown operatively associated with a flexible member or suture construct. The tensioning members can facilitate attachment and/or additional tensioning of the various suture constructs discussed above, as well as individual strands of suture, and can be used in addition to or in lieu of the various attachment members (e.g., 380, 430, 472) discussed above.

With particular reference to FIGS. 17-21, a tensioning member 700 is shown operatively associated with a pair of suture loops. The pair of suture loops can be loops of two separate strands of suture or can be the adjustable suture loops of the suture constructs 10, 150, 150A discussed above. In this regard, it should be appreciated that while the following discussion will continue with reference to adjustable loops 188, 188' of adjustable suture construct 150, the pair of adjustable loops shown operatively associated with tensioning member 700 can also include adjustable loops 66, 70 of suture construct 10, adjustable loops 240, 240' of suture construct 150A, loops of individual looped stands of suture, and/or a single strand of suture secured to each of the attachment members such as by wrapping and/or tying thereto. It should also be appreciated that while the tensioning members discussed herein illustrate adjustable suture loops of the suture constructs being attached thereto, other portions of the suture constructs discussed herein, such as the passage portions, can also be coupled to the attachment members in lieu of one of the adjustable loops.

Figure 29:
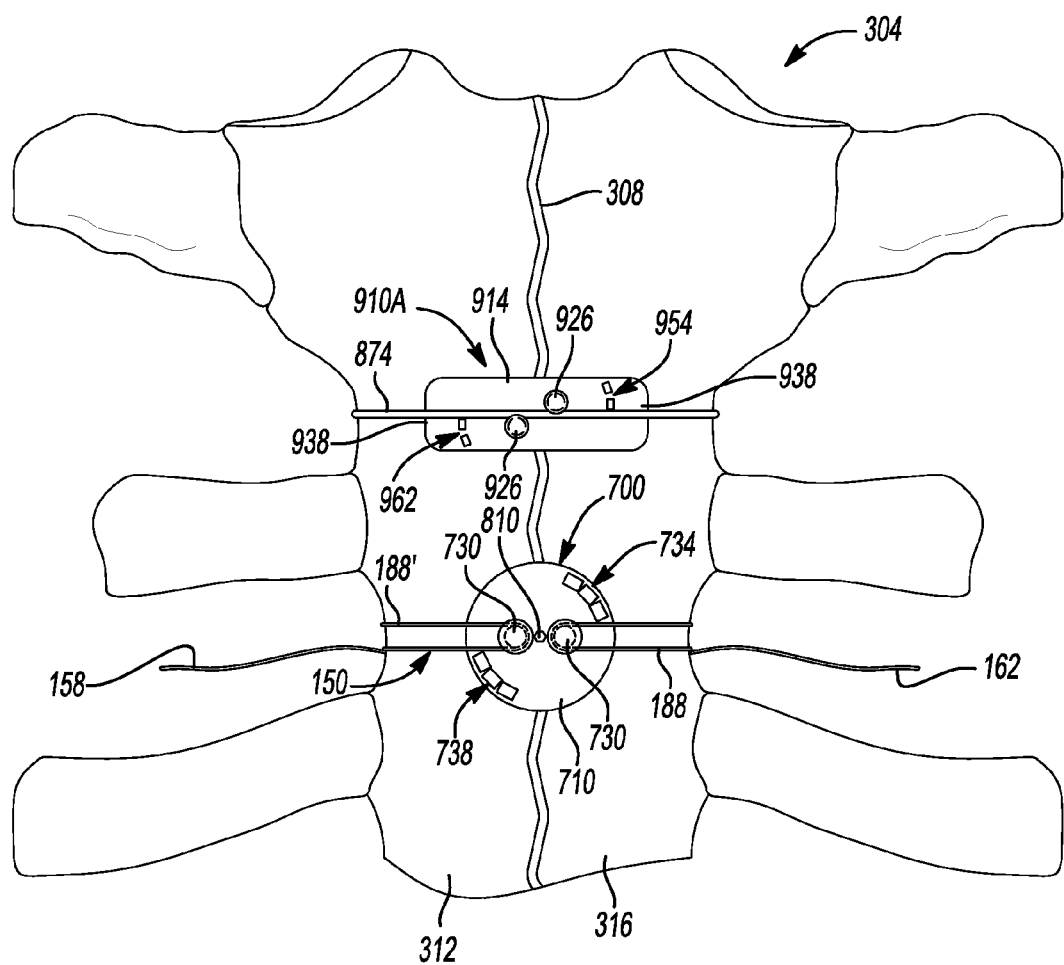
FIGS. 29-31 depict exemplary use of the tensioning members in exemplary sternal closure and fracture fixation procedures.
Figure 30:
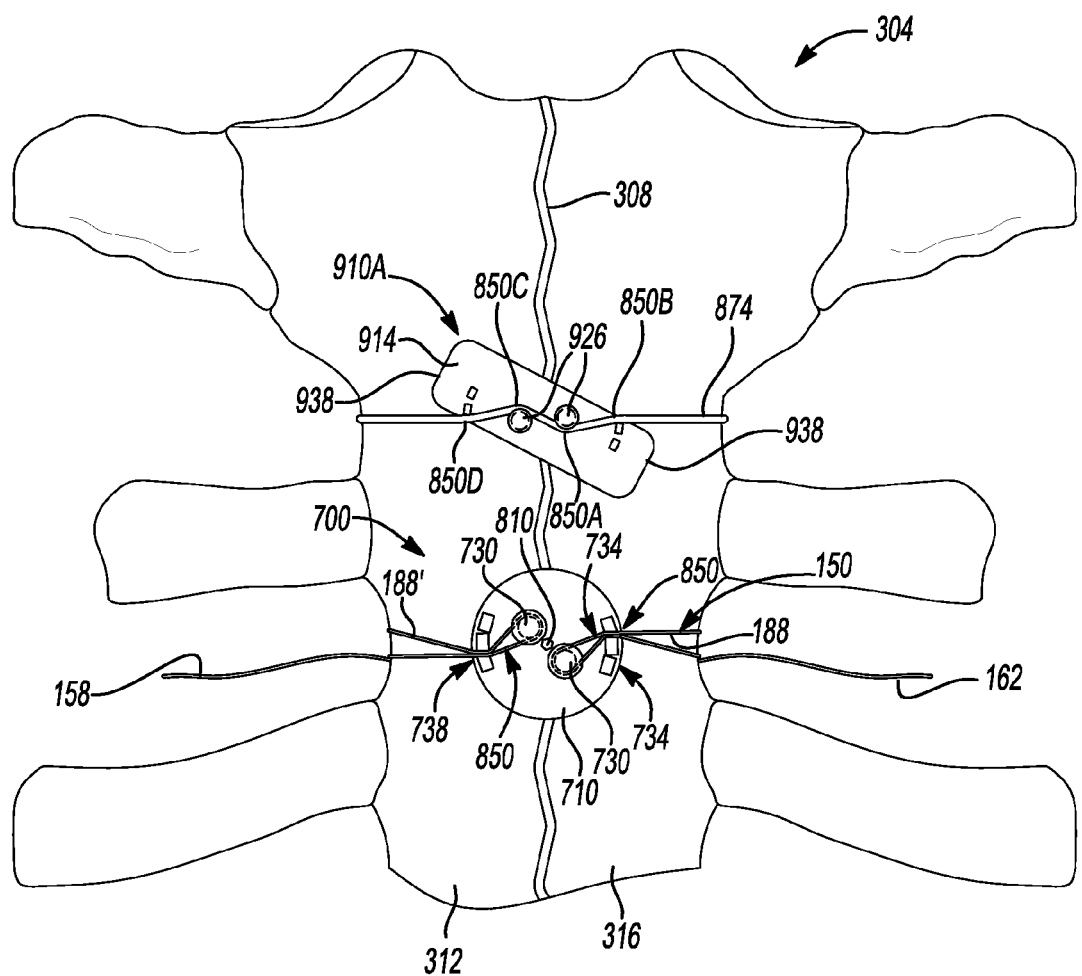
Figure 31:
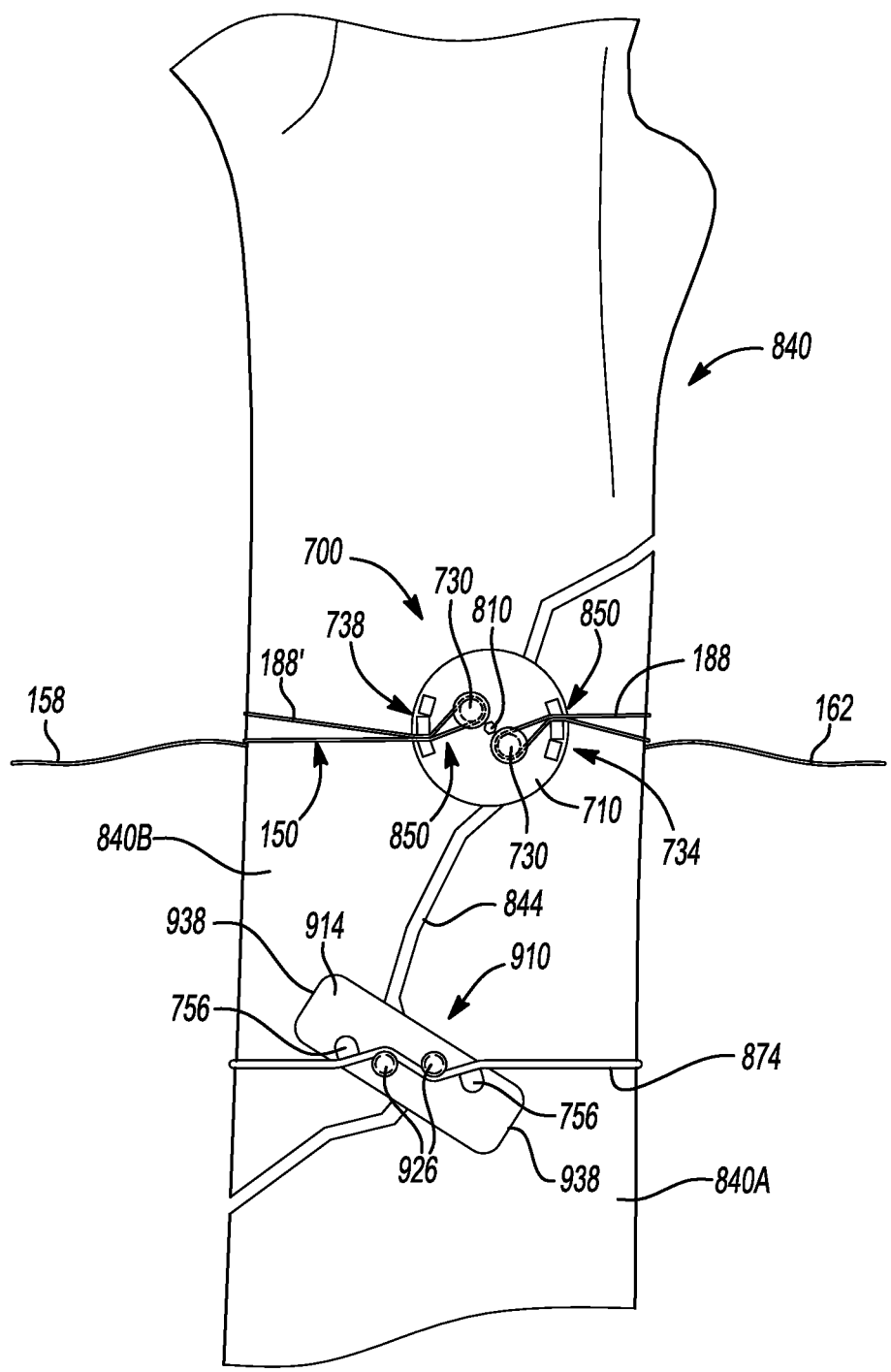

The tensioning member 700 can be used to facilitate securing suture construct 150 around a fractured bone or the sectioned sternum 304 to compress the fracture or section and affect healing, as shown for example in FIGS. 29-31. The tensioning member 700 can be used for attachment of adjustable loops 188, 188' as well as to provide additional tensioning of suture construct 150 after the construct 150 has been tensioned as discussed above.

Figure 17:
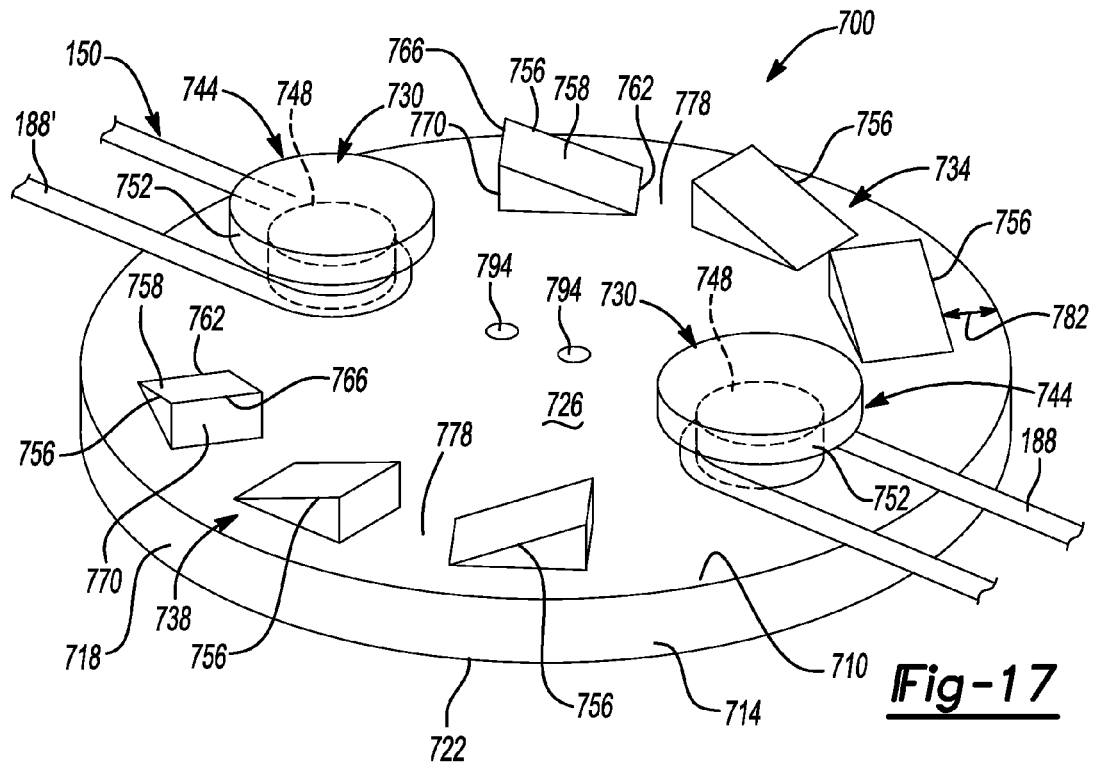

With particular reference to FIG. 17, tensioning member 700 can include a body 710 having a perimeter 714 with a generally circular shape 718. It should be appreciated that the shape of tensioning member 700 can be varied as may be desired for various surgical procedures and/or to facilitate gripping an outer perimeter of the tensioning member 700, as will be discussed below. Body 710 can include a first bone or soft tissue engaging side 722 and an opposite second or upper side 726. A pair of attachment members 730 and a first and second set of suture engaging members 734, 738 can extend from the upper side 726, as shown in FIG. 17. In the exemplary configuration shown in FIG. 17, the upper side 726 can include a substantially smooth or uninterrupted planar surface, except for members 730, 734 and 738, so as to not interfere with suture loops 188, 188' during adjustment of tensioning member 700, as will be discussed in greater detail below. Similarly, the first side 722 can also include a substantially smooth or uninterrupted planar bone engaging surface.

In the exemplary configuration shown in FIG. 17, the attachment members 730 can include a pair of opposed posts 744 having a first portion 748 extending from the upper side 726 and a second portion 752 having a larger diameter than the first portion 748 so as to form an undercut retention feature for retaining loops 188, 188'. Alternatively, the attachment members can include recessed posts 496, such as shown in FIG. 9, and/or recessed apertures, such as the attachment portions 384 of FIG. 7. In another exemplary alternative configuration, the suture or suture loops 188, 188' could be integrally formed with or attached to one of the attachment members 730.

The first and second set of suture engaging members 734, 738 can each include a plurality of ramped members 756 having an angled or inclined upper surface 758 with a first end 762 extending from the upper side 726 and a second end 766 spaced apart from the upper side 726 so as to form a wall 770 configured to selectively engage the suture loops 188, 188'. In an exemplary configuration, the wall 770 can be perpendicular or substantially perpendicular to upper side 726. In another exemplary configuration, the wall 770 can include an arcuate portion and/or an undercut to aid in retention of the suture loops 188, 188'. In an exemplary configuration, the plurality of ramped members 756 can be positioned along an arcuate path, as shown for example in FIG. 17.

The first and second set of suture engaging members 734, 738 can include a varying number of ramped members 756 to provide a varying degree of tension adjustment capability, as will be discussed in greater detail below. In this regard, spacing 778 between the number of provide ramped members 756 can also be varied, such as the different spacing shown between the ramped members 756 of FIGS. 17 and 18. Further, a distance 782 from the perimeter 714 to each of the attachment members 730 can be varied to vary an amount of additional tension applied to the suture construct 150 as the tensioning member 700 is rotated, as will also be discussed below in connection with operation of the tensioning member 700.

Figure 18:
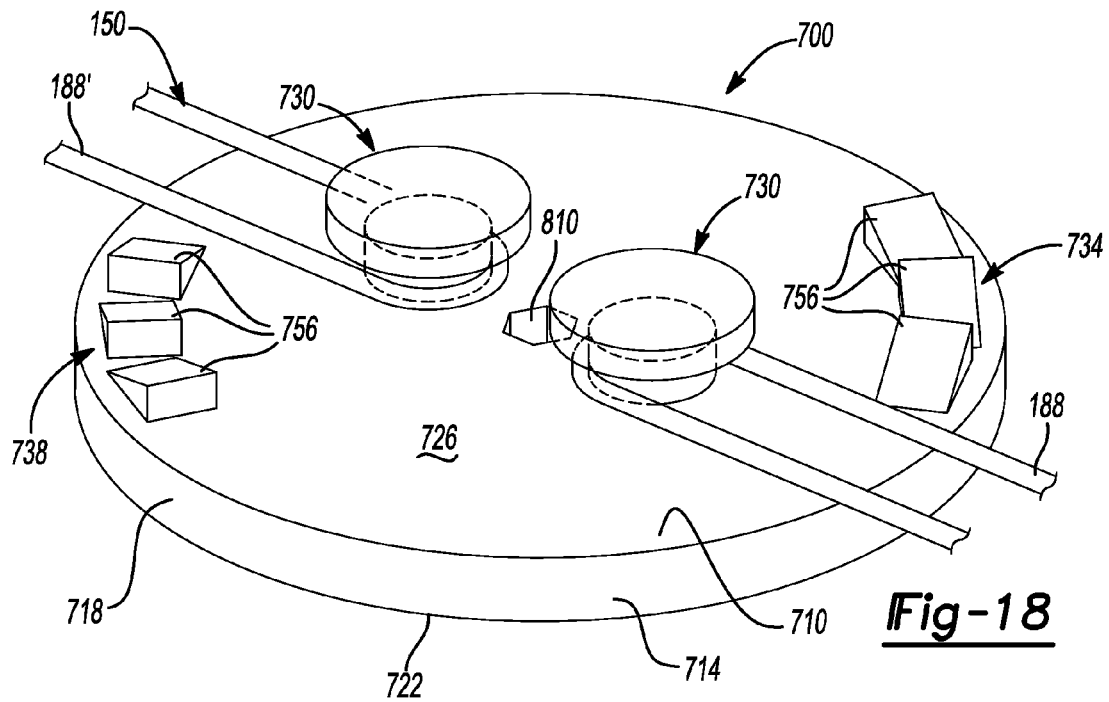
Figure 26:
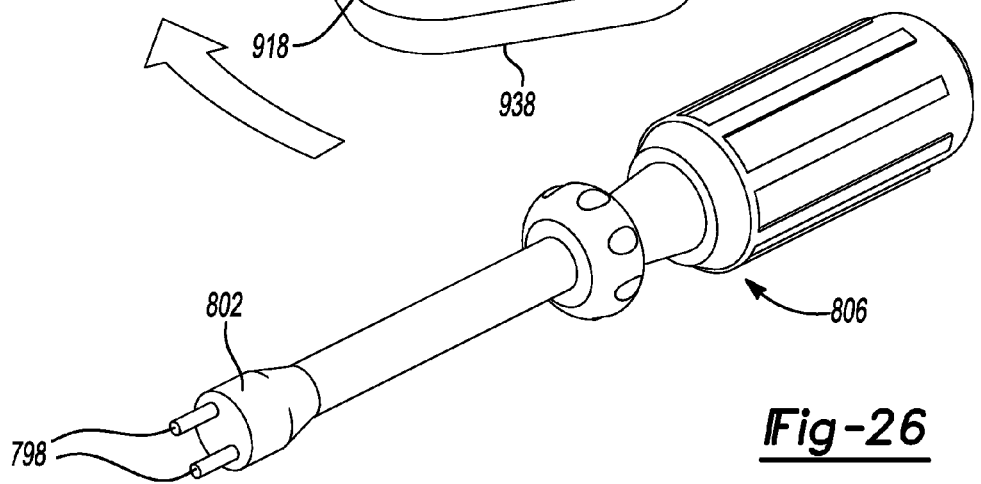
FIG. 26 depicts an exemplary instrument for adjusting the tensioning members according to the present teachings.

With continuing reference to FIG. 17 and additional reference to FIGS. 18-20, tensioning member 700 can include various features configured to facilitate rotationally driving tensioning member 700 to impart additional tension on suture construct 150. For example, FIG. 17 illustrates a pair of apertures 794 extending through body 17 proximate a center thereof. Apertures 794 can receive a pair of projections 798 extending from a distal end 802 of a driver 806 (FIG. 26). Rotation of driver 806 can thereby rotate tensioning member 700, as will be discussed below. As another example, FIG. 18 illustrates a hexagon shaped aperture 810 in lieu of the pair of apertures 794. For this configuration, driver 806 could include a singe projection (not shown) having a hexagon shaped outer surface sized and shaped to drivingly engaging the hexagon shaped aperture 810.

FIG. 19 illustrates another exemplary configuration where a pair of notches 818 are formed in the perimeter 714 for receiving a corresponding driving tool (not shown) or to facilitate manual manipulation with a surgeon's or clinician's hand. In FIG. 20, the perimeter 714 is shown with a hexagon shape 822 to facilitate hand manipulation by the surgeon or clinician. It should be appreciated that tensioning member 700 can be provided with one or more of the driving features discussed above. In this regard, it should also be appreciated that the attachment members 730 can be used in addition to or in lieu of the driving features discussed above to rotate tensioning member 700.

With additional reference to FIGS. 21 and 29-31, operation of tensioning member 700 will now be discussed in greater detail. Tensioning member 700 can be used to facilitate attachment of loops 188, 188' of suture construct 150, as well as to provide additional tension to suture construct 150 after it has been tensioned in the manner discussed above in connection with the sternal closure procedure. In the exemplary procedure shown in FIGS. 29-31, tensioning member 700 can be positioned on the sectioned sternum 304 (FIGS. 29-30) and/or the fractured bone 840 (FIG. 31) to facilitate attachment of suture construct 150 to the respective bone as well as providing additional tensioning capabilities.

As discussed above in connection with the sternal closure surgical procedure, suture construct 150 can be similarly wrapped around the sternum 304 or bone 840 such that the loops 188, 188' are coupled to the pair of attachment members 730. Alternatively, passage portion 168 could be coupled to one of the attachment members 730 and the first and second loops 188, 188' could be coupled to the second attachment member. Similarly, in another alternative configuration, passage portion 168 of suture construct 150A could be coupled to one of the attachment members and the first and second loops 240, 240' could be coupled to the other attachment member.

Free ends 158, 162 of suture construct 150 can then be tensioned to reduce loops 188, 188' to the desired size and tension to compress and close section 308 of sternum 304 (or fracture 844 of bone 840) and assist healing, as shown in FIGS. 29 and 31 with reference to FIG. 10 and attachment member 380. With particular reference to FIG. 31, suture construct 150 can be wrapped around bone 840 about fracture 844 to compress fractured bone portions 840A and 840B and promote healing. It should be appreciated that the tensioning members and suture constructs discussed herein can also be used in connection with two separate bones where the suture construct is wrapped around the two bones and tension is applied to draw the bones toward each other.

Once suture construct 150 has been tensioned as discussed above, tensioning member 700 can be optionally rotated to impart additional tension on suture construct 150 and thus additional compression on section 308 or fracture 844. In the configuration illustrated in FIGS. 21 and 29-31, tensioning member 700 can be rotated clockwise to impart additional tension on suture construct 150. In particular, tensioning member 700 can be rotated clockwise to engage one of the ramped members 756 of each set of suture engaging members 734, 738 with a respective adjustable loop 188, 188', as shown in FIG. 21. Rotation of tensioning member 700 in the clockwise direction will draw adjustable loop 188 in the direction of arrow A and will draw adjustable loop 188' in the direction of arrow B thereby imparting additional tension on suture construct 150, as also shown in FIG. 21. As tensioning member 700 is rotated clockwise and attachment members 730 draw loops 188, 188' in the respective directions A and B, the ramped members 756 of the first and second set of suture engaging members 734, 738 are brought into engagement with the respective adjustable loops 188, 188'.

As each ramped member 756 is brought into contact with the respecting suture loops 188, 188', the inclined surface 758 is facing the adjustable loops 188, 188' and facilitates the adjustable loops 188, 188' sliding over the inclined surfaces 758 from the first end 762 toward the second end 766 to be positioned adjacent the wall 770 of a desired ramped member 756. Upon a desired amount of tension being imparted on the suture construct 150 by rotation of tensioning member 700 such that the adjustable loops 188, 188' are positioned about the first and second set of suture engaging members 734, 738, an external force (e.g. surgeon's hand and/or driver 806) that is being used to rotate tensioning member 700 can be removed. Upon removing the external driving force, the increased tension in suture construct 150 from rotation of tensioning member 700 can urge tensioning member 700 to rotate in a counterclockwise direction toward the initial position shown in FIGS. 17-20. This action can bring the wall 770 of the ramped member 756 adjacent adjustable loops 188, 188' into contact with the adjustable loops 188, 188' such that the ramped members 756 exert a force on the adjustable loops 188, 188', as shown in FIG. 21.

As a result, the adjustable loops 188, 188' can be bent and tensioned around the respective engaging ramped members 756 such that a non-linearity 850 is created in the adjustable loops 188, 188'. This non-linearity 850 effectively increases a distance the adjustable loops 188, 188' are required to extend relative to the original position of the adjustable loops 188, 188' (before tensioning member 700 was rotated into engagement with adjustable loops 188, 188') and thus increases the tension in suture construct 150. In particular, the suture construct 150 can be tensioned about sectioned sternum 304 or fractured bone 840 to a first tension by tensioning the free ends 158, 162 in the manner discussed above. In an exemplary aspect, the first tension can draw the respective bone portions into contact with each other and compress the bone portions together. Subsequently, the tensioning member 700 can be rotated in the manner discussed above to tension suture construct to a second tension and apply further compression to the bone portions to promote fusion and healing.

As can be appreciated, a larger degree of clockwise rotation of tensioning member 700 such that adjustable loops 188, 188' are engaged with ramped members 756 that are positioned further away (i.e., in a counterclockwise direction) from the adjustable loops 188, 188', can impart a greater amount of additional tension on suture construct 150. For example, rotating tensioning member 700 such that adjustable loops 188, 188' are positioned behind a second ramped member 756B of the three ramped members 756 shown in FIG. 21 can create a larger bend or non-linearity 850 in adjustable loops 188, 188' as compared to the adjustable loops being positioned behind a first ramped member 756A. Similarly, positioning the adjustable loops behind a third ramped member 756C will create a larger non-linearity 850 than discussed above with respect to ramped members 756B and thus provide the largest amount of additional tensioning associated with the exemplary tensioning member 700 shown in FIG. 21. In this regard, it should be appreciated that additional ramped members 756 and/or increased spacing between the ramped members 756 can provide for additional tension increasing capability of tensioning member 700.

With additional reference to FIGS. 22 and 23, an alternative tensioning member 700A will now be discussed. Tensioning member 700A can be similar to tensioning member 700 such that like reference numerals refer to like features and only differences will be discussed in detail. Tensioning member 700A can include an attachment member 870 configured to receive a flexible member 874. Flexible member 874 can be a portion of one of the suture constructs 10, 150, 150A discussed above, or can be a portion of an individual suture strand or a portion of a flexible member such as a wire. In an aspect where suture 874 is a portion of one of the suture constructs discussed above, it should be appreciated that a portion of one of the loops and/or the passage portions of such suture constructs can be received in attachment member 870. Thus, while the following discussion will continue with reference to suture 874, it will be appreciated that suture 874 is representative of any of the suture constructs discussed herein.

Figure 22:
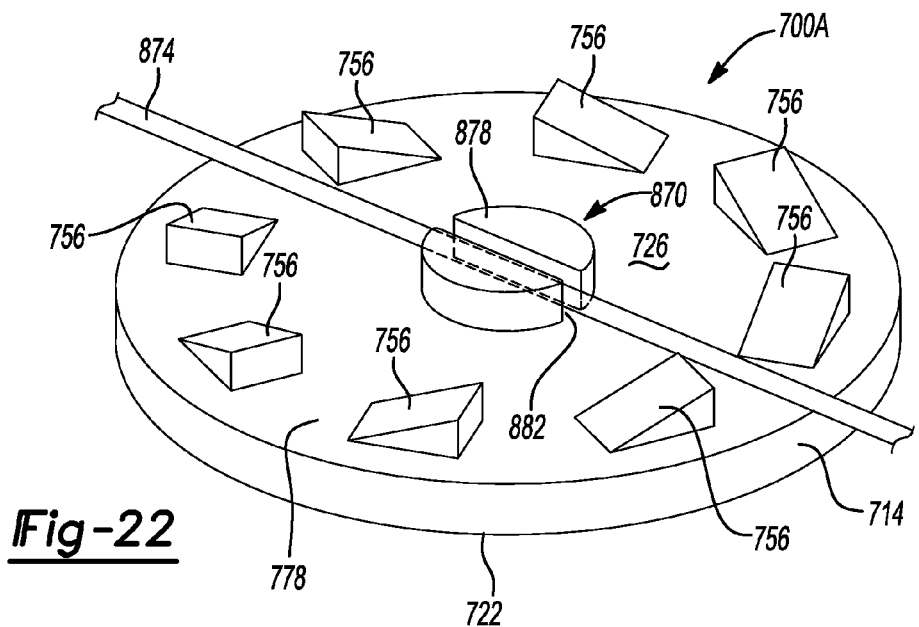
FIGS. 22-23 depict another exemplary tensioning member for tensioning a flexible member construct according to the present teachings.
Figure 23:
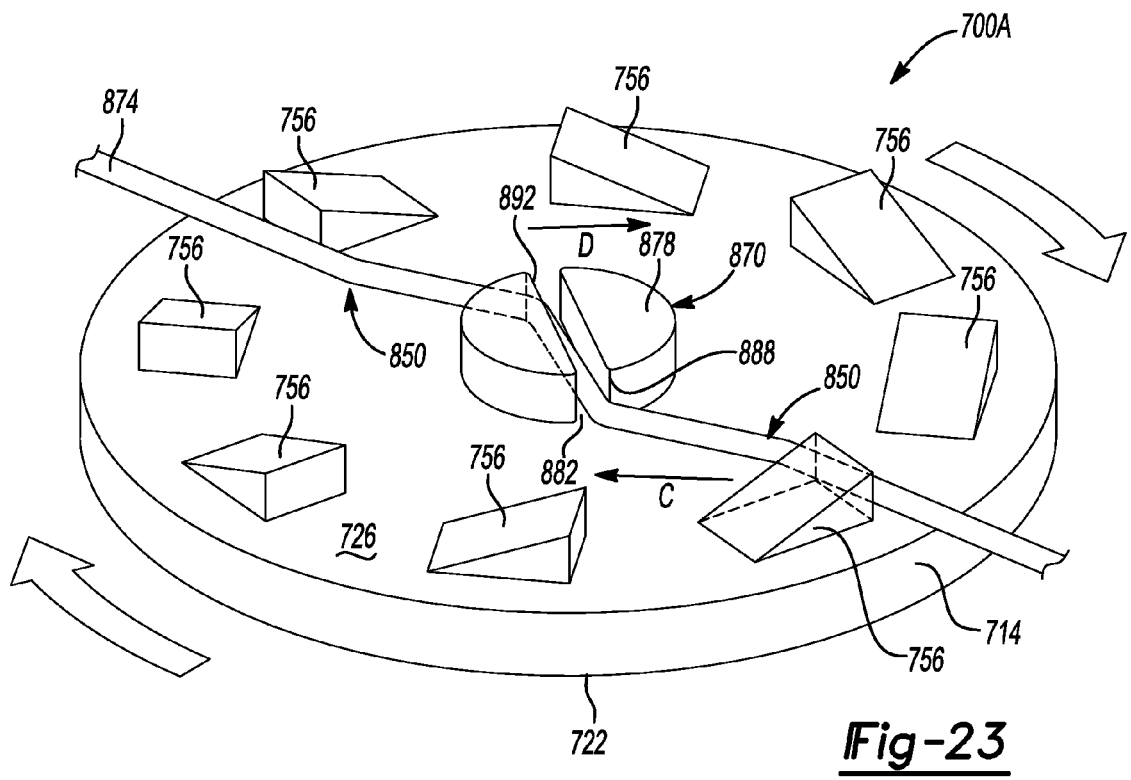

Attachment member 870 can include a protrusion 878 extending from the upper side 726, as shown in FIG. 22. The protrusion 878 can include a channel 882 extending therethrough that receives the suture 874. In one exemplary aspect, attachment member 870 can include two separate protrusions 878 spaced apart from each other so as to form channel 882. Tensioning member 700A can similarly include a plurality of ramped members 756 positioned on the upper side 726 and extending along an arcuate path. In the exemplary configuration illustrated, the ramped members 756 can extend circumferentially around the body 710 proximate the perimeter 714. In another exemplary configuration, the ramped members can be positioned as two sets, similar to the ramped members 756 of the first and second set of suture engaging members 734, 738 of tensioning member 700.

In operation, tensioning member 700A can be rotated clockwise similar to the rotation discussed above for tensioning member 700 to impart additional tension on suture 874. With particular reference to FIG. 23, tensioning member 700A can be rotated clockwise whereby channel 882 bends suture 874 and draws a portion of suture 874 proximate a first end 888 of channel 882 in the direction of arrow C and another portion of the suture 874 proximate a second end 892 of channel 882 in the opposite direction of arrow D. Such drawing of the suture 874 requires suture 874 to extend a greater distance and thus increases the tension in suture 874.

Similar to tensioning member 700 discussed above, the rotation of tensioning member 700A can cause suture 874 to slide over ramped members 756 until a rotational driving force used to rotate tensioning member 700A is removed. In this regard, it should be appreciated that tensioning member 700A can include one or more of the driving features discussed above in connection with tensioning member 700. For example, apertures 794 can be positioned in each of protrusions 78 and/or the outer perimeter can include the notches 818 or hexagon shape 822. Upon removal of the driving force, the additional tension in suture 874 can urge tensioning member 700A to rotate in the counterclockwise direction partially back toward the original position shown in FIG. 23. However, as with tensioning member 700, the ramped member wall 770 adjacent the suture 874 can engage the suture 874 and resist such counter rotation in cooperation with channel 882 and thereby create the non-linearity or bend 850 in suture 874. The non-linearity 850 requires the suture 874 to extend a greater distance and thereby increases the tension in suture 874 similar to tensioning member 700. Further, tensioning member 700A can automatically maintain the increased tension in suture 874 similar to tensioning member 700 due to the counteracting forces imparted on suture 874 from the engaging ramped members 756 and the attachment members 870.

Figure 24:
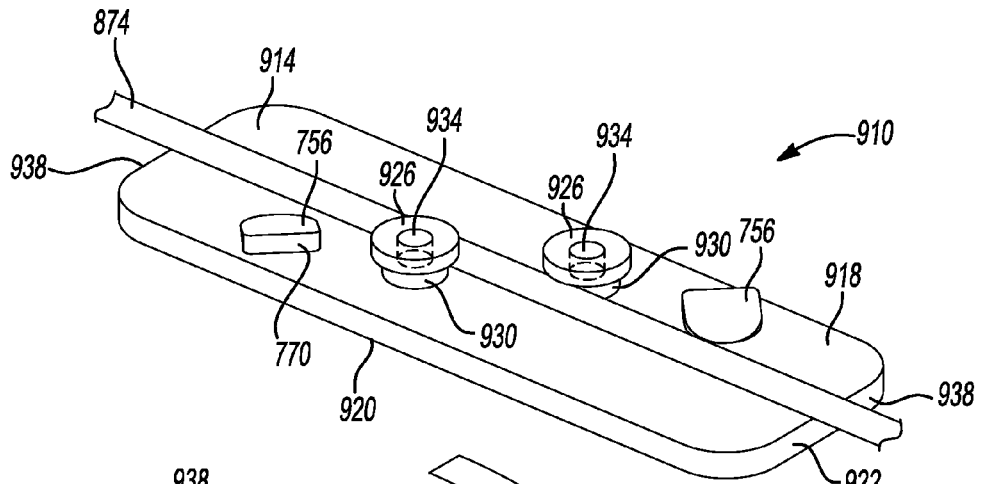
FIGS. 24-25 depict another exemplary tensioning member for tensioning a flexible member construct according to the present teachings.
Figure 25:
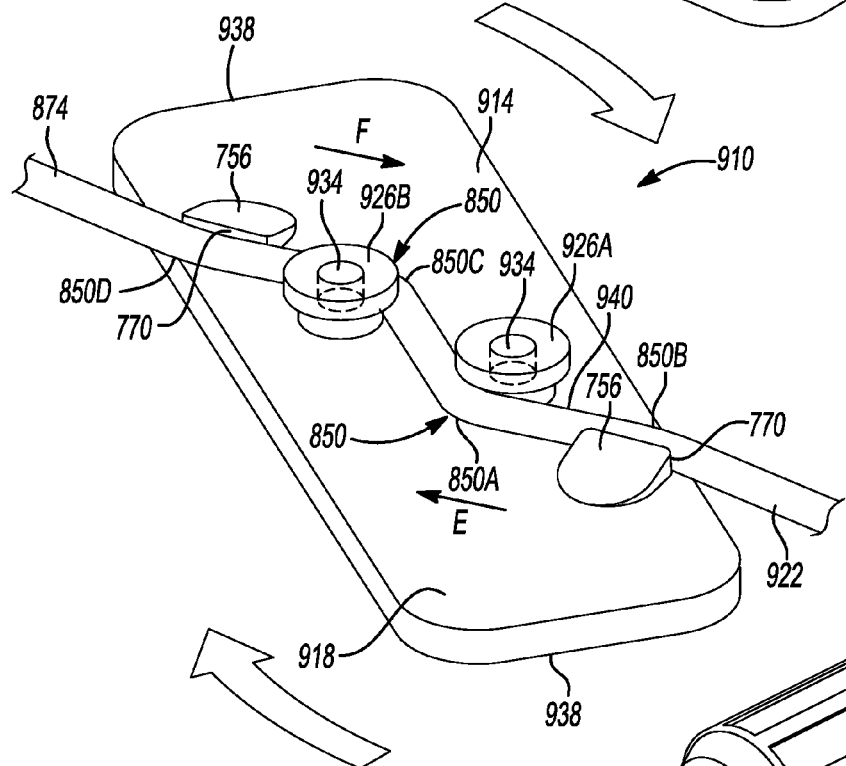

With additional reference to FIGS. 24-26, a tensioning member 910 is shown in accordance with the present teachings. Tensioning member 910 can include a body 914 having an upper surface 918 and an opposite lower tissue or bone engaging surface 920. Body 914 can define a generally rectangular perimeter 922, although it should be appreciated that tensioning member 910 can include a body 914 with other shapes as may be desired depending on different procedures in which tensioning member 910 may be used. A pair of generally centrally located attachment members 926 can extend from the upper surface 918 and can include an undercut portion 930 similar to that discussed above for attachment members 730. Attachment members 926 can each include an aperture 934 formed in a top surface thereof configured to receive the projections 798 of driver 806, as will be discussed below.

In the exemplary configuration illustrated in FIG. 24, the pair of attachment members 926 can be spaced apart from each other such that they are offset from each other in both a longitudinal direction of body 914 and a perpendicular lateral direction of body 914. The offset can facilitate generating the bending of suture 874 similar to the tensioning members discussed above. As also discussed above, tensioning member 910 can be used in addition to or in lieu of the various attachment members 380, 430 and 472 shown for example in FIGS. 7-9. Further, tensioning member 910 can also be used with any of the suture constructs discussed herein similar to that discussed above for tensioning members 700 and 700A.

Tensioning member 910 can include a single ramped member 756 extending from the upper surface 918 and spaced apart from each of the respective attachment members 926 in a direction toward opposed longitudinal ends 938, as shown in FIG. 24. It should be appreciated that tensioning member 910 can alternatively include a plurality of ramped members 756, such as shown for example in FIG. 27. It should also be appreciated that tensioning member 910 can use any of the alternative driving features discussed above in lieu of or in addition to the apertures 934.

In operation, tensioning member 910 can be positioned on soft tissue or bone and suture 874 or one of the suture constructs discussed herein can be positioned between attachment members 926, as shown in FIGS. 24 and 25. The suture 874 can then be tensioned around the sternum 304 or other bone 840 to compress the respective section 308 or fracture 844 as discussed above and shown in FIG. 31. Tensioning member 910 can then be rotated clockwise using driver 806 or another suitable method and/or instrument. For example, the projections 798 of driver 806 can be positioned in apertures 934. Driver 806 can then be rotated to rotate tensioning member 910 clockwise and drive attachment members 926 into portions of suture 874 and draw the suture 874 in the direction of arrows E and F shown in FIG. 25. Drawing suture 874 in the direction of arrows E and F requires the suture 874 to extend over a greater distance thereby increasing the tension in suture 874.

Tensioning member 910 can be rotated clockwise until suture 874 slides over ramped members 756. The rotational driving force (i.e., from driver 806) can then be removed, upon which tensioning member 910 can be urged counterclockwise partially toward the initial position shown in FIG. 24 until the walls 770 of ramped members 756 engage suture 874. This action can impart a force on suture 874 thereby causing the non-linearity or bending 850 relative to each attachment member 926 and ramped member 756. In this regard, a first one of the attachment members 926A can engage a first side 940 of suture 874 and the wall 770 of the adjacent ramped member 756 can engage a second opposite side 942 of suture 874. Similarly, a second one of the attachment members 926B can engage the second side 942 of suture 874 and the wall 770 of the corresponding ramped member 756 can engage the first side 940, as shown in FIG. 25.

The non-linearity 850 can effectively increase a distance the suture 874 is required to extend, such as around bone 840 to compress fracture 844, and can thereby increase tension in suture 874, as shown for example in FIG. 31. In the exemplary configuration shown in FIG. 25, the non-linearity 850 with respect to attachment member 926A can include a first bend or non-linearity 850A as the suture is bent around attachment member 926A, and a second non-linearity 850B as the suture is bent around the associated ramped member 756. Similarly, the non-linearity with respect to attachment member 926B can include a third bend or non-linearity 850C as the suture is bent around attachment member 926B, and a fourth non-linearity 850D as the suture is bent around the associated ramped member 756. The tension in suture 874 in cooperation with the engagement of the ramped members 756 and the attachment members 926 can automatically maintain the non-linearity 850 and increased tension in suture 874 imparted by tensioning member 910.

Figure 27:
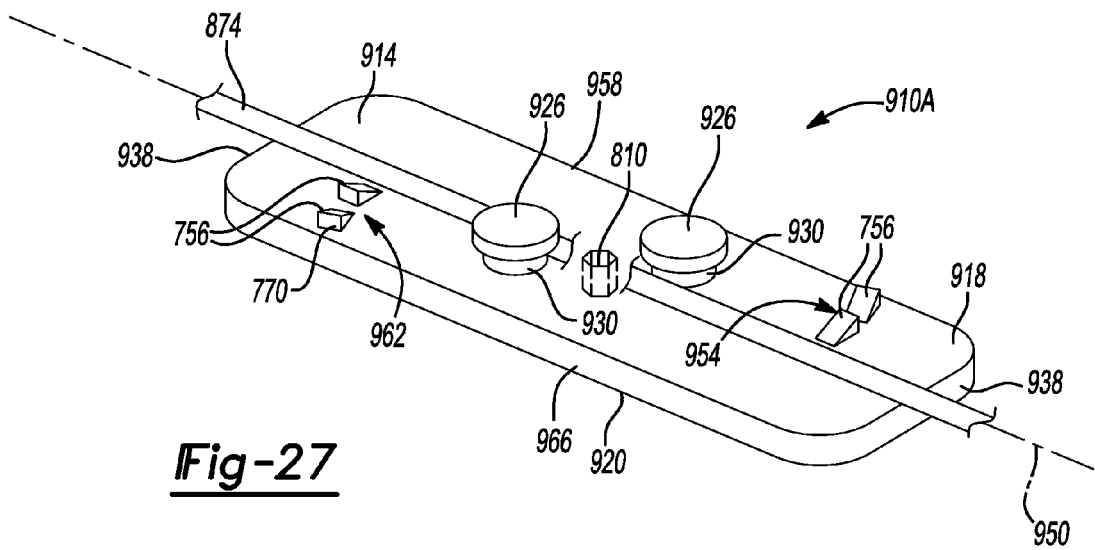
FIGS. 27-28 depict another exemplary tensioning member for tensioning a flexible member construct according to the present teachings.
Figure 28:
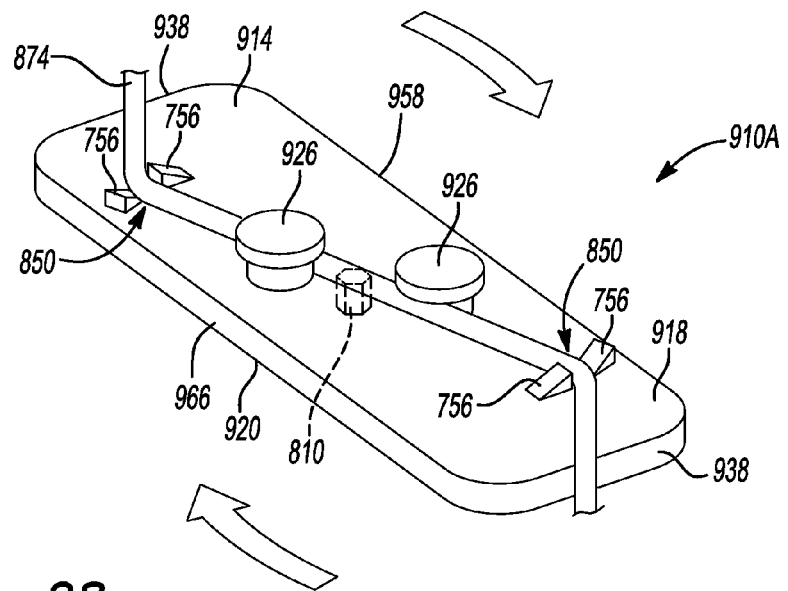

With additional reference to FIGS. 27 and 28, a tensioning member 910A is shown according to the present teachings. Tensioning member 910A can be similar to tensioning member 910 such that like reference numerals refer to like components and only differences will be discussed in detail. Tensioning member 910A can include two sets of ramped members 756 spaced apart from the respective attachment members 926, as shown in FIG. 27. In an exemplary aspect, each set of ramped members 756 can be positioned in an arcuate path. In an exemplary aspect, each set of ramped members 756 can be positioned relative to a longitudinal centerline 950 such that a first set 954 of the ramped members 756 are positioned between centerline 950 and a first lateral side 958 and a second set 962 of the ramped members 756 are positioned between centerline 950 and a second opposite lateral side 966. Tensioning member 910A can also include the hexagon shaped aperture 810 in place of or in addition to the apertures 934.

In operation, tensioning member 910A can be utilized in a similar manner as tensioning member 910 and can be used in addition to or in lieu of tensioning members 700, 700A and 910. Further, tensioning member 910A can be used in lieu of or in addition to attachment members 380, 430, and/or 472. For example, and with reference to FIGS. 29 and 30, tensioning member 910A can be positioned on the sternum 304 and suture 874 (or one of the suture constructs discussed above) can be positioned around the sternum 304 and section 308. The suture 874 or suture construct 150 can then be appropriately tensioned. Tensioning member 910A can then be rotated in a clockwise direction to engage attachment members 926 and ramped members 756 with suture 874 in the manner discussed above and shown in FIG. 31 to impart additional tension on suture 874.

Figure 32:
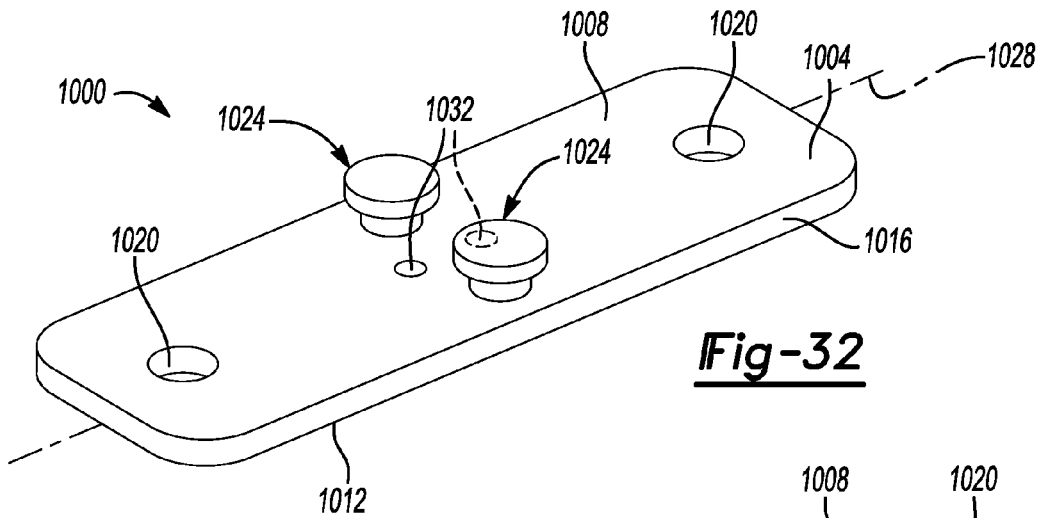
FIGS. 32-33 depict aspects of another exemplary tensioning member for tensioning a flexible member construct according to the present teachings.
Figure 33:
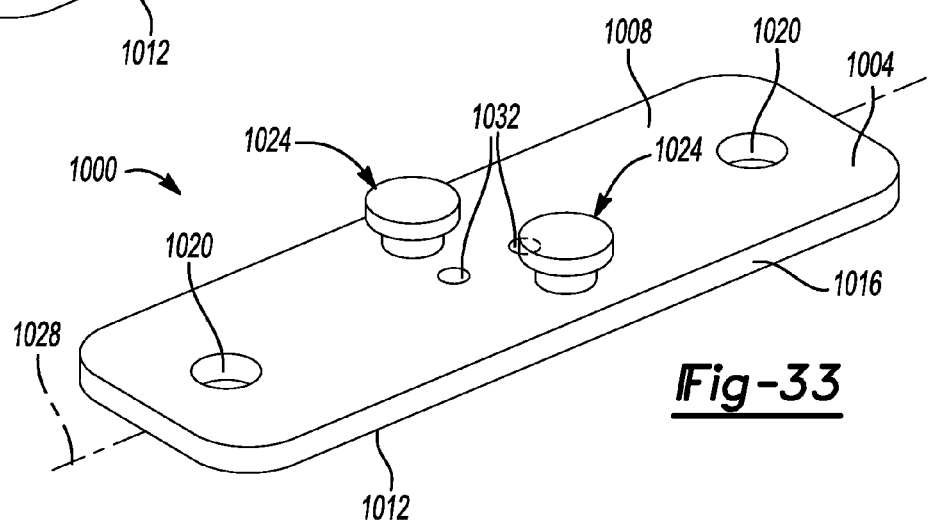

Turning now to FIGS. 32-33, a tensioning member 1000 is shown in accordance with the present teachings. Tensioning member 1000 can include a body 1004 having a first or upper surface 1008 and a second or bone engaging surface 1012. Tensioning member 1000 can define an outer perimeter 1016 and, in the exemplary configuration illustrated, can have an elongated or rectangular shape. Tensioning member 1000 can include a first set of fastener receiving holes 1020 extending through body 1004, as shown in FIG. 32. It should be appreciated that tensioning member 1000 can include more or less than the set of two fastener receiving holes 1020 illustrated in FIGS. 32 and 33. Tensioning member 1000 can also include a pair of attachment members 1024 that can be similar to attachment members 730 discussed above. Attachment members 1024 and can be positioned along an axis perpendicular to a longitudinal axis 1028 of tensioning member 1000, as shown in FIG. 32, or at an offset angle from perpendicular, as shown in FIG. 33. Attachment members 1024 can be configured to receive suture 874 or loops of one or more of the suture constructs discussed above, such as loops 188, 188' of construct 150. Tensioning member 100 can further include a pair of apertures 1032 configured to receive projection 798 of driver 806 similar to apertures 934 discussed above.

In operation, tensioning member 1000 can be positioned relative to the fractured bone 840 or sectioned sternum 304. Tensioning member 1000 can be coupled to one of the suture constructs, such as to the loops 188, 188' of exemplary suture construct 150, in a manner similar to tensioning member 700 discussed above in connection with FIGS. 30 and 31. Driver 806 can then be used to rotate tensioning member 1000 to impart additional tension on to associated suture construct 150 by requiring suture construct 150 to span or extend a longer distance similar to operation of the tensioning members discussed above. Upon rotating tensioning member 1000 to impart a sufficient amount of additional tension onto associated suture construct 150 and/or compression onto section 308 or fracture 844, a pair of bone screws or fasteners 1038 can secure tensioning member 1000 in the tensioned and rotated position to the sternum 304 or bone 840.

Figure 34:
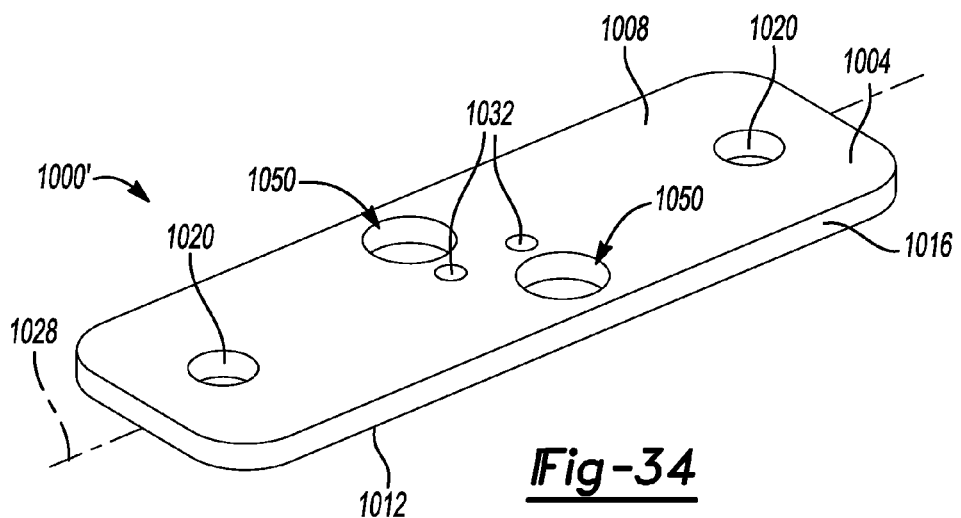
FIG. 34-36 depict aspects of another exemplary tensioning member for tensioning a flexible member construct according to the present teachings.
Figure 35:
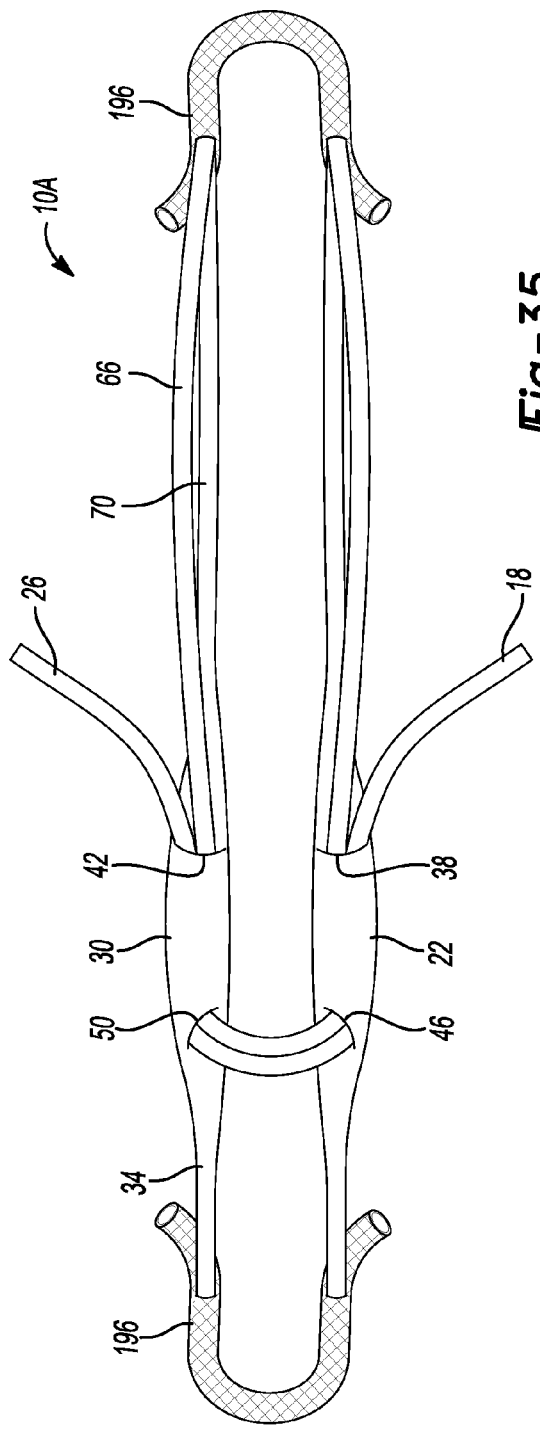
Figure 36:
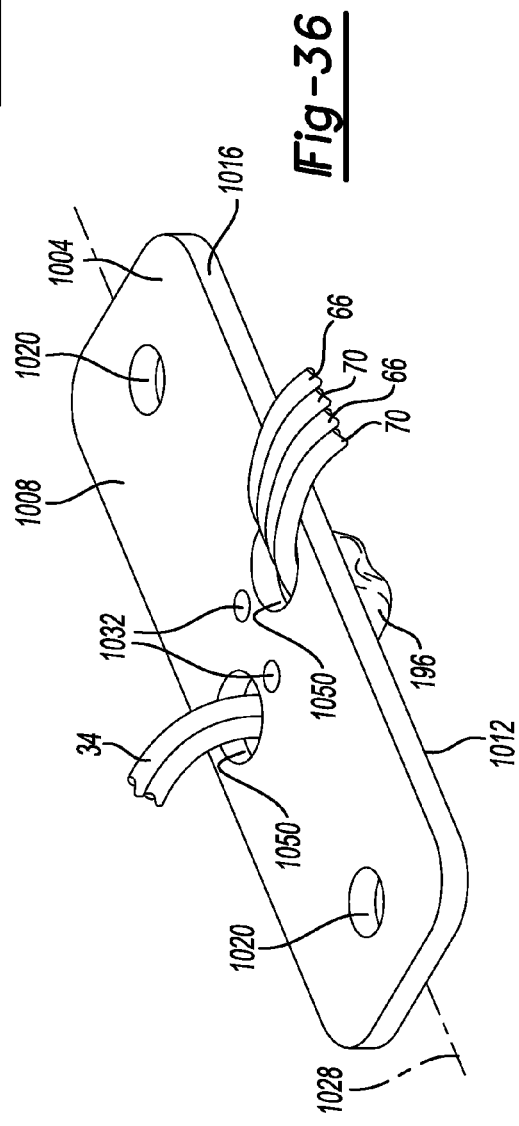

With additional reference to FIGS. 34-36, another tensioning member 1000' is shown in accordance with the present teachings. Tensioning member 1000' can be similar to tensioning member 1000 such that like reference numerals refer to like components and features and only differences will be discussed in detail. Tensioning member 1000' can include a pair of attachment members 1050 in the form of apertures in place of attachment members 1024 of tensioning member

1000. Attachment members 1050 can be positioned along an axis substantially perpendicular to longitudinal axis of 1028 or offset therefrom, as shown in the exemplary configuration of FIG. 34.

In operation, flexible anchors 196 associated with any of the suture constructs discussed above, such as construct 150A of FIG. 3B or construct 10A of FIG. 35, can be coupled to attachment members 1050. In particular, one of the flexible anchors 196 carried by a respective suture construct can be coupled to one of the attachment members 1050. Tensioning member 1000' can then be positioned about fracture 844 or section 308 and wrapped around the respective bone 840 or sternum 308. The other flexible anchor 196 coupled to an opposite end of the respective suture construct, such as construct 10A, can be coupled to the other attachment member 1050, as generally shown in FIG. 36. Tensioning member 1000' can then be tensioned and secured in a similar manner as tensioning member 1000 discussed above.

Turning now to FIGS. 37-40, a tensioning member 1070 is shown in accordance with the present teachings. Tensioning member 1070 can operate similarly to tensioning member 1000 and can include a body 1074 in the form of an I-shape 1078 in the exemplary configuration illustrated. In this exemplary configuration, body 1074 can include a first portion 1082 having opposed ends 1086 and 1090. First portion 1082 can define a longitudinal axis 1094 of tensioning member 1070. Second and third portions 1098 and 1102 can extend perpendicular or substantially perpendicular to first portion 1082 about respective ends 1086 and 1090 thereby forming the I-shape 1078.

Similar to tensioning member 1000, first portion 1082 can include a pair of attachment members 1106 and a pair of driver engagement apertures 1110. Attachment members 1106 can be positioned along an axis substantially perpendicular to longitudinal axis 1094, or along an axis offset from perpendicular to longitudinal axis 1094, as shown in FIG. 37. Each of the second and third portions 1098 and 1102 can include at least one bone screw receiving aperture 1114. In the exemplar configuration illustrated, each of the second and third portions 1098 and 1102 include four apertures 1114 configured to receive bone screws 1038.

In operation, tensioning member 1070 can be positioned relative to fractured bone 840 or sectioned sternum 304, as shown in FIG. 37. One of the suture constructs discussed above can be coupled to attachment members 1106, such as via loops 188, 188' of exemplary suture construct 150. Suture construct 150 can then be tensioned in the manner discussed above to impart compression on fracture 844 or section 308. Tensioning member 1070 can then be rotated to impart additional tension onto suture construct 150 and compression onto fracture 844 or section 308, as generally shown in FIGS. 37 and 38. In this regard, by having the attachment members 1106 offset from perpendicular to the longitudinal axis, as shown in FIG. 37, rotation of tensioning member 1070 can bring longitudinal axis 1094 generally in line with fracture 844 or section 308 such that the second and third portions 1098, 1102 span fracture 844 or section 308, as generally shown in FIG. 38.

Bone screws 1038 can then received through apertures 1114 to secure tensioning member 1070 to bone 840 or sternum 304 in the rotated position, as shown in FIG. 39. In this regard, tensioning member 1070 can be used not only to impart additional tension on the associated suture construct, but also to secure the fracture bone 840 or section 308 together in its compressed state when second and third portions 1098, 1102 span both sides of fracture 844 or section 308, as also shown in FIG. 39.

With additional reference to FIG. 40, an alternative exemplary process for rotating tensioning member about bone 840 or sternum 304 will be discussed. Tensioning member 1070 can be positioned relative to the fractured bone 840 or sternum 304 in a similar manner as discussed above such that the longitudinal axis 1094 of tensioning member 1070 is angled relative to fracture 844 or section 308 and tensioning member 1070 is skewed to one side of fracture 844 or section 308, as shown in FIG. 40. One bone screw 1038 can be positioned in the second portion 1098 and partially secured to bone 840 or sternum 304 so as to initially serve as a pivot point 1122 for rotating tensioning member 1070. In the exemplary configuration illustrated in FIG. 40, bone screw 1038 can be positioned in one of the apertures 1114 that is furthest from fracture 844 or section 308. Suture construct 150 can then be coupled to attachment members 1106 in the manner discussed above.

Tensioning member 1070 can then be rotated about the partially secured bone screw 1038 in a direction toward fracture 844 or section 308 so as impart additional tension onto suture construct 150 and thus compression onto fracture 844 or section 308. Once tensioning member 1070 is rotated to the position generally shown in FIG. 39, the additional bone screws 1038 can be positioned in the apertures 1114 and all of the bone screws 1038 can be driven into the associated bone to secure tensioning member 1070 thereto in the rotated state.

Figure 41:
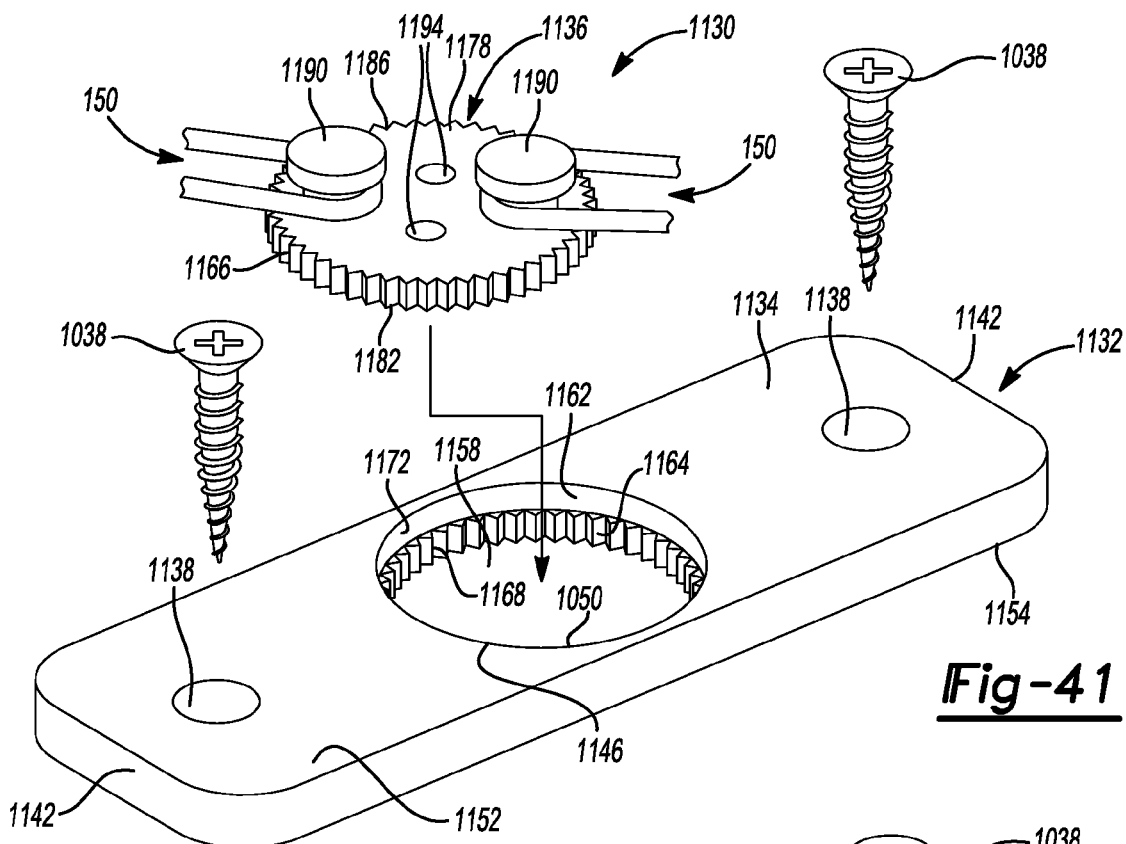
FIG. 41 depicts another exemplary tensioning member for tensioning a flexible member construct according to the present teachings.

Turning now to FIG. 41, a tensioning member assembly 1130 is shown in accordance with the present teachings. Tensioning member assembly 1130 can include a first member 1132 having a body 1134 and a second member 1136 configured to be selectively movable relative thereto, as will be discussed below in greater detail. Body 1134 can include a pair of bone screw receiving holes 1138 proximate opposed ends 1142 thereof. In the exemplary configuration illustrated, body 1134 can be elongated so as to have an oval or rectangular shape. Body 1134 can also include a centrally positioned circular closed-end recess or pocket 1146 having an opening 1150 formed in an upper surface 1152 of body 1134 opposite a bottom or bone engaging surface 1154.

Pocket 1146 can extend partially toward bone engaging surface 1154 and can include a floor or bottom 1158 and a perimeter sidewall 1162. Alternatively, pocket 1146 can be formed as an aperture extending through body 1134. The sidewall 1162 of pocket 1146 can include a splined configuration 1164 configured to mate or mesh with a complimentary splined configuration 1166 of second member 1136. In the exemplary configuration illustrated, the sidewall 1162 can include the splined configuration 1164 on only a lower portion 1168 proximate bone engaging surface 1154 such that an upper portion 1172 does not include splined configuration 1164.

Second member 1136 can include an upper surface 1178, a lower surface 1182 and an outer perimeter 1186. In the exemplary configuration illustrated in FIG. 41, second member 1136 can have a circular shape with a diameter complimentary to a diameter of pocket 1146. The outer perimeter 1186 can include the splined configuration 1166 such that second member 1136 can be selectively received in splined engagement with first member 1132. A pair of attachment members 1190 can extend from the upper surface 1178 in a similar manner as the various attachment members discussed above. A pair of driver engagement apertures 1194 can also be formed in the upper surface 1178 for receiving driver 806.

In operation, one of the suture constructs discussed above, such as construct 150, can be coupled to attachment members 1190 of second member 1136. First member 1132 can be positioned about a fractured bone, such as bone 840, and secured thereto with bone screws 1038. Second member 1136 can be coupled to driver 806 and positioned proximate first member 1132. In one exemplary configuration, the driver 806 can be configured to cooperate with the second member 1136 such that second member 1136 can remain removably coupled to driver 806 upon engagement of projections 798 with apertures 1194. In one exemplary configuration, second member 1136 can be positioned relative to pocket 1146 such that the splined configuration 1166 resides in the upper portion 1172 of sidewall 1162 and does not engage the splined configuration 1164 of pocket 1146. Second member 1136 can be rotated via driver 816 to impart additional tension onto tensioned suture construct 150 optionally using upper portion 1172 as a guide. Upon imparting the desired additional tension onto suture construct 150 and thus compression onto fractured bone 840, second member 1136 can be positioned in pocket 1146 such that the second member splined configuration 1166 engages the first member splined configuration 1164 thereby preventing relative movement between the first and second members 1132, 1136 to maintain the additional tension and compression.

Figure 42:
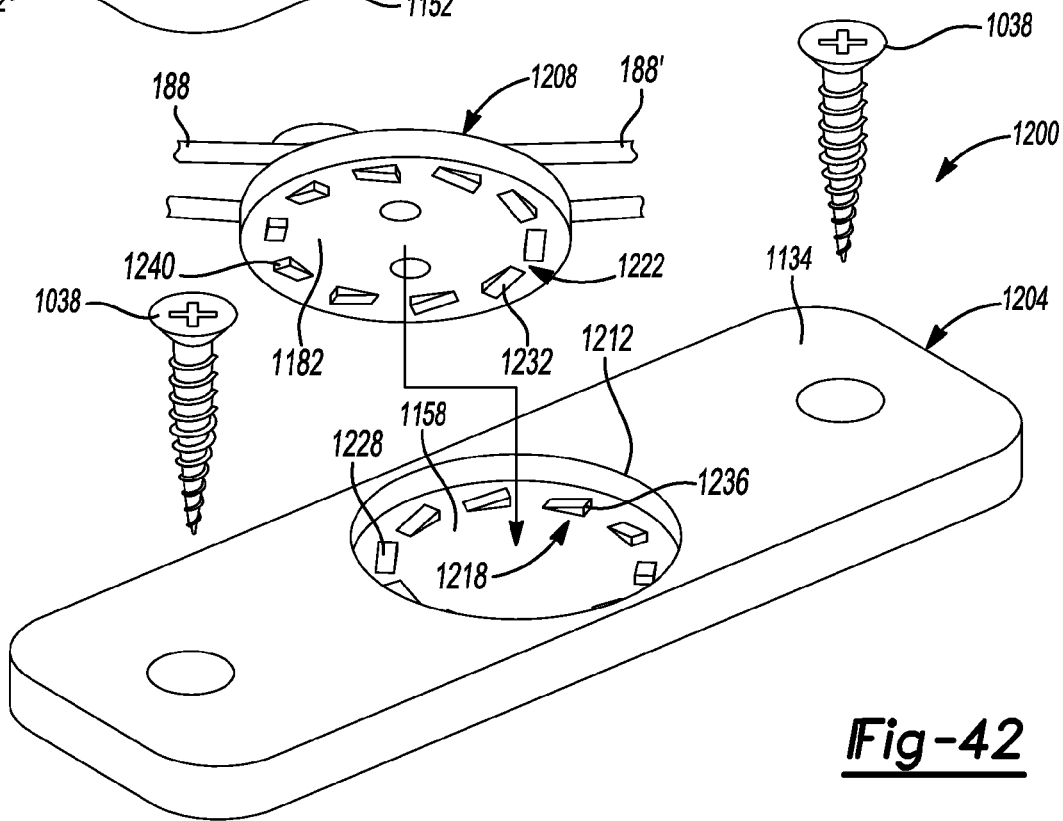
FIG. 42 depicts another exemplary tensioning member for tensioning a flexible member construct according to the present teachings.

With additional reference to FIG. 42, another tensioning member assembly 1200 is shown in accordance with the present teachings. Aspects of tensioning member assembly 1200 can be similar to tensioning member assembly 1130 such that like reference numerals refer to like features and only differences will be discussed in detail. Tensioning member assembly 1200 can similarly include a first member 1204 and a second member 1208. Second member 1208 can be configured to be received in a pocket 1212 formed in the body 1134 of first member 1204. Pocket 1212 can be similar to pocket 1146, but can include a plurality of ramped members 1218 on floor 1158 in place of the splined configuration 1164. As will be discussed in greater detail below, ramped members 1218 can be configured to cooperate with a corresponding plurality of opposed ramped members 1222 on second member 1208 to allow selective rotation of second member 1208 relative to first member 1204 in a first predetermined rotation direction while preventing relative rotation in a second opposite rotational direction.

Similar to tensioning member assembly 1130, second member 1208 can have a diameter complimentary to a diameter of pocket 1212. Second member 1208 can also include the plurality of ramped members 1222 on bottom or lower surface 1182 radially spaced so as to align with the plurality of ramped members 1218 of first member 1204. In this regard, as can be seen in FIG. 42, the ramped members 1218, 1222 can cooperate to allow rotation of the second member 1208 relative to the first member 1204 in the first rotational direction where inclined surfaces 1228, 1232 of respective ramped members 1218, 1222 can slide relative to each other, and can prevent rotation in the second rotational direction where end faces 1236, 1240 of respective ramped members 1218, 1222 can engage each other.

In operation, loops 188, 188' of suture construct 150 can be coupled to second member 1208 in a similar manner as second member 1136 discussed above. Likewise, first member 1204 can be positioned about fractured bone 844 and coupled thereto with bone screws 1038. Second member 1208 can be positioned in pocket 1212 such that the ramped members 1218, 1222 are in engagement or substantial engagement with each other. Suture construct 150 can be tensioned in the manner discussed above to compress fractured bone portions 840A, 840B (or sectioned sternum 304) together also in a similar manner as discussed above. Driver 806 can be coupled to second member 1208, if not already coupled thereto, and can be used to rotate second member 1208 in the first direction relative to first member 1204 to impart additional tension on suture construct 150 and thus compression on fracture 844 of bone 840. Upon imparting the desired additional tension and compression, driver 806 can be released thereby allowing the second member 1208 to rotate slightly in the second direction until the end faces 1236, 1240 engage each other thereby preventing any further rotation in the second direction and maintaining the additional imparted tension on suture construct 150 and thus compression on fractured bone 840.

While one or more specific examples have been described and illustrated, it will be understood by those skilled in the art that various changes may be made and equivalence may be substituted for elements thereof without departing from the scope of the present teachings as defined in the claims. Furthermore, the mixing and matching of features, elements and/or functions between various examples may be expressly contemplated herein so that one skilled in the art would appreciate from the present teachings that features, elements and/or functions of one example may be incorporated into another example as appropriate, unless described otherwise above. Moreover, many modifications may be made to adapt a particular situation or material to the present teachings without departing from the essential scope thereof.

What is claimed is:

1. A method for applying tension to a flexible member, comprising:
   positioning a tensioning member relative to a first bone portion and a second bone portion, the tensioning member having first and second flexible member attachment members and a corresponding set of first and second flexible member engaging members extending therefrom;
   positioning the flexible member about the first and second bone portions;
   coupling the flexible member to the first and second attachment members;
   tensioning the flexible member to draw the first and second bone portions toward each other under a first tension;
   rotating the tensioning member such that the first and second attachment members draw the flexible member in opposite directions applying additional tension to the flexible member to place the flexible member and the first and second bone portions under a second tension;
   engaging the flexible member with the first and second flexible member engaging members and creating a non-linearity in the flexible member about each of the flexible member engaging members; and
   maintaining the second tension via engagement of the flexible member with the first and second attachment members and the first and second engagement members in an absence of an external force.

2. The method of claim 1, wherein positioning the flexible member about the first and second bone portions includes wrapping the flexible member around the first and second bone portions.

3. The method of claim 1, wherein coupling the flexible member to the first and second attachment members includes coupling a first adjustable loop of an adjustable suture construct formed from a suture to a first post and coupling a second adjustable loop of the adjustable suture construct to a second post, the first and second adjustable loops extending from a passage portion of the adjustable suture construct.

4. The method of claim 1, wherein coupling the flexible member to the first and second attachment members includes coupling an adjustable suture construct formed from a suture to the first and second attachment members, the adjustable suture construct having a first end of the suture that extends through a first aperture defined by the suture into the passage portion and out a second aperture defined by the suture so that the first end is outside of the passage portion and defines a first adjustable loop, and having a second end of the suture that extends through the second aperture into the passage portion and out the first aperture so that the second end is outside of the passage portion and defines a second adjustable loop.

5. The method of claim 4, wherein coupling the flexible member to the first and second attachment members includes coupling the first adjustable loop to the first attachment member and coupling the second adjustable loop to the second attachment member.

6. The method of claim 4, wherein coupling the flexible member to the first and second attachment members includes coupling the first and second adjustable loops to the first attachment member and coupling the passage portion to the second attachment member.

7. The method of claim 1, wherein tensioning the flexible member to draw the first and second bone portions toward each other under a first tension includes tensioning the flexible member relative to the first and second attachment members.

8. The method of claim 1, wherein rotating the tensioning member such that the attachment members draw the flexible member in opposite directions applying additional tension to the flexible member to place the flexible member and the first and second bone portions under a second tension includes engaging a driver with the tensioning member and rotating the driver to rotate the tensioning member.

9. The method of claim 1, wherein engaging the flexible member with the first and second flexible member engaging members includes:
    sliding the flexible member over a first ramped surface of the flexible member engaging members; and
    engaging the flexible member against a second side surface of the flexible member engaging member;
    wherein the flexible member is bent around the second side surface of each flexible member engaging member thereby creating the non-linearity.

10. The method of claim 9, wherein the first and second flexible member engaging members include a first and second plurality of flexible member engaging members each having the first ramped surface and second side surface, each plurality of flexible member engaging members being positioned consecutively in a single row;
    wherein continued rotation of the tensioning member slides the flexible member over consecutive flexible member engaging members of each of the first and second plurality of flexible member engaging members; and
    wherein engaging the flexible member with each consecutive ramped member second side surface increases the second tension applied to the flexible member and first and second bone portions.

11. The method of claim 1, wherein tensioning the flexible member to draw the first and second bone portions toward each other under a first tension includes compressing the first and second bone portions of the same fractured bone.

12. The method of claim 1, wherein tensioning the flexible member to draw the first and second bone portions toward each other under a first tension includes drawing the first and second bone portions of a different bone toward each other.

13. The method of claim 1, wherein engaging the flexible member with the first and second flexible member engaging members and creating a non-linearity in the flexible member about each of the flexible member engaging members includes engaging a first side of the flexible member with the first engaging member and engaging a second side of the flexible member opposite the first side with the second engaging member.

14. The method of claim 1, wherein engaging the flexible member with the first and second flexible member engaging members and creating a non-linearity in the flexible member about each of the flexible member engaging members includes:
    engaging a first side of the flexible member with the first attachment member and a second opposite side of the flexible member with the first engaging member; and
    engaging the second side of the flexible member with the second attachment member and the first side of the flexible member with the second engaging member.

15. A method for applying tension to a suture, comprising:
    positioning a tensioning member relative to a first bone portion and a second bone portion, the tensioning member having first and second suture attachment members and a corresponding first and second plurality of suture engaging members extending therefrom;
    positioning an adjustable suture construct about the first and second bone portions;
    coupling first and second adjustable loops of the adjustable suture construct to the first and second attachment members;
    tensioning free ends of the adjustable suture construct to reduce a size of the first and second adjustable loops and draw the first and second bone portions toward each other under a first tension;
    rotating the tensioning member such that the first and second attachment members draw the adjustable suture construct in opposite directions applying additional tension to the suture construct to place the suture construct and the first and second bone portions under a second tension;
    engaging the first and second adjustable loops with a respective one of the plurality of first and second suture engaging members and creating a non-linearity in the adjustable loops about each of the one of the plurality of first and second suture engaging members; and
    maintaining the second tension via engagement of the first and second adjustable loops with the first and second suture attachment members and the one of the plurality of first and second suture engagement members in an absence of an external force.

16. The method of claim 15, wherein engaging the first and second adjustable loops with the respective one of the plurality of first and second suture engaging members and creating the non-linearity in the adjustable loops about each of the one of the plurality of first and second suture engaging members includes:
    sliding the first and second adjustable loops over a ramped surface of the respective one of the plurality of first and second engaging members; and
    engaging the first and second adjustable loops against a side surface of the respective one of the plurality of first and second engaging members;
    wherein the first and second adjustable loops are bent around the side surfaces thereby creating the non-linearity.

17. The method of claim 16, wherein the first and second plurality of suture engaging members are each positioned consecutively in a single row, each consecutively positioned suture engaging member after a first suture engaging member of the first and second plurality of suture engaging members providing additional tension to the adjustable suture construct upon engagement with the respective first and second adjustable loops; and wherein sliding the first and second adjustable loops over the ramped surface of the respective one of the plurality of first and second engaging members includes rotating the tensioning member to slide the first and second adjustable loops over the ramped surfaces of a respective sub-plurality of the plurality of first and second suture engaging members.

18. The method of claim 15, wherein tensioning free ends of the adjustable suture construct to reduce a size of the first and second adjustable loops and draw the first and second bone portions toward each other under a first tension includes compressing the first and second bone portions of the same fractured bone.

19. The method of claim 18, wherein tensioning free ends of the adjustable suture construct to reduce a size of the first and second adjustable loops includes compressing the first and second bone portions of a sectioned sternum.

20. The method of claim 15, wherein tensioning free ends of the adjustable suture construct to reduce a size of the first and second adjustable loops and draw the first and second bone portions toward each other under a first tension includes drawing the first and second bone portions of a different bone toward each other.

21. A method for applying tension to a flexible member, comprising:

positioning a tensioning member relative to a first bone portion and a second bone portion, the tensioning member having first and second flexible member attachment members and a corresponding set of first and second flexible member engaging members extending therefrom;

positioning the flexible member about the first and second bone portions;

coupling the flexible member to the first and second attachment members;

tensioning the flexible member to draw the first and second bone portions toward each other under a first tension;

rotating the tensioning member such that the first and second attachment members draw the flexible member in opposite directions applying additional tension to the flexible member to place the flexible member and the first and second bone portions under a second tension;

engaging the flexible member with the first and second flexible member engaging members and creating a non-linearity in the flexible member about each of the flexible member engaging members; and maintaining the second tension via engagement of the flexible member with the first and second attachment members and the first and second engagement members in an absence of an external force;

wherein rotating the tensioning member such that the attachment members draw the flexible member in opposite directions applying additional tension to the flexible member to place the flexible member and the first and second bone portions under a second tension includes engaging a driver with the tensioning member and rotating the driver to rotate the tensioning member.

22. The method of claim 21, wherein positioning the flexible member about the first and second bone portions includes wrapping the flexible member around the first and second bone portions.

23. The method of claim 21, wherein coupling the flexible member to the first and second attachment members includes coupling a first adjustable loop of an adjustable suture construct formed from a suture to a first post and coupling a second adjustable loop of the adjustable suture construct to a second post, the first and second adjustable loops extending from a passage portion of the adjustable suture construct.

24. The method of claim 21, wherein coupling the flexible member to the first and second attachment members includes coupling an adjustable suture construct formed from a suture to the first and second attachment members, the adjustable suture construct having a first end of the suture that extends through a first aperture defined by the suture into the passage portion and out a second aperture defined by the suture so that the first end is outside of the passage portion and defines a first adjustable loop, and having a second end of the suture that extends through the second aperture into the passage portion and out the first aperture so that the second end is outside of the passage portion and defines a second adjustable loop.

25. The method of claim 21, wherein engaging the flexible member with the first and second flexible member engaging members includes:

sliding the flexible member over a first ramped surface of the flexible member engaging members; and engaging the flexible member against a second side surface of the flexible member engaging member;

wherein the flexible member is bent around the second side surface of each flexible member engaging member thereby creating the non-linearity.

26. The method of claim 25, wherein the first and second flexible member engaging members include a first and second plurality of flexible member engaging members each having the first ramped surface and second side surface, each plurality of flexible member engaging members being positioned consecutively in a single row;

wherein continued rotation of the tensioning member slides the flexible member over consecutive flexible member engaging members of each of the first and second plurality of flexible member engaging members; and wherein engaging the flexible member with each consecutive ramped member second side surface increases the second tension applied to the flexible member and first and second bone portions.

27. A method for applying tension to a flexible member, comprising:

positioning a tensioning member relative to a first bone portion and a second bone portion, the tensioning member having first and second flexible member attachment members and a corresponding set of first and second flexible member engaging members extending therefrom;

positioning the flexible member about the first and second bone portions;

coupling the flexible member to the first and second attachment members;

tensioning the flexible member to draw the first and second bone portions toward each other under a first tension;

rotating the tensioning member such that the first and second attachment members draw the flexible member in opposite directions applying additional tension to the flexible member to place the flexible member and the first and second bone portions under a second tension;

engaging the flexible member with the first and second flexible member engaging members and creating a non-linearity in the flexible member about each of the flexible member engaging members; and maintaining the second tension via engagement of the flexible member with the first and second attachment members and the first and second engagement members in an absence of an external force;

wherein engaging the flexible member with the first and second flexible member engaging members includes:

sliding the flexible member over a first ramped surface of the flexible member engaging members; and engaging the flexible member against a second side surface of the flexible member engaging member;

wherein the flexible member is bent around the second side surface of each flexible member engaging member thereby creating the non-linearity; and wherein the first and second flexible member engaging members include a first and second plurality of flexible member engaging members each having the first ramped surface and second side surface, each plurality of flexible member engaging members being positioned consecutively in a single row;

wherein continued rotation of the tensioning member slides the flexible member over consecutive flexible member engaging members of each of the first and second plurality of flexible member engaging members; and wherein engaging the flexible member with each consecutive ramped member second side surface increases the second tension applied to the flexible member and first and second bone portions.

28. The method of claim 27, wherein positioning the flexible member about the first and second bone portions includes wrapping the flexible member around the first and second bone portions.

29. The method of claim 27, wherein coupling the flexible member to the first and second attachment members includes coupling a first adjustable loop of an adjustable suture construct formed from a suture to a first post and coupling a second adjustable loop of the adjustable suture construct to a second post, the first and second adjustable loops extending from a passage portion of the adjustable suture construct.

30. The method of claim 27, wherein coupling the flexible member to the first and second attachment members includes coupling an adjustable suture construct formed from a suture to the first and second attachment members, the adjustable suture construct having a first end of the suture that extends through a first aperture defined by the suture into the passage portion and out a second aperture defined by the suture so that the first end is outside of the passage portion and defines a first adjustable loop, and having a second end of the suture that extends through the second aperture into the passage portion and out the first aperture so that the second end is outside of the passage portion and defines a second adjustable loop.

31. The method of claim 27, wherein rotating the tensioning member such that the attachment members draw the flexible member in opposite directions applying additional tension to the flexible member to place the flexible member and the first and second bone portions under a second tension includes engaging a driver with the tensioning member and rotating the driver to rotate the tensioning member.

* * * * *